(12) United States Patent
Ju et al.

(10) Patent No.: US 11,421,258 B2
(45) Date of Patent: Aug. 23, 2022

(54) PRODUCTION OF FERMENTATION PRODUCTS CONTAINING RHAMNOLIPIDS

(71) Applicants: Lu-Kwang Ju, Akron, OH (US); Krutika Invally, Woburn, MA (US)

(72) Inventors: Lu-Kwang Ju, Akron, OH (US); Krutika Invally, Woburn, MA (US)

(73) Assignee: THE UNIVERSITY OF AKRON, Akron, OH (US)

( * ) Notice: Subject to any disclaimer, the term of this patent is extended or adjusted under 35 U.S.C. 154(b) by 83 days.

(21) Appl. No.: 16/536,791

(22) Filed: Aug. 9, 2019

(65) Prior Publication Data
US 2020/0048673 A1 Feb. 13, 2020

Related U.S. Application Data

(60) Provisional application No. 62/716,660, filed on Aug. 9, 2018.

(51) Int. Cl.
*C12P 19/44* (2006.01)
*C12N 1/20* (2006.01)

(52) U.S. Cl.
CPC ............. *C12P 19/44* (2013.01); *C12N 1/20* (2013.01)

(58) Field of Classification Search
CPC .................................. C12P 19/44; C12N 1/20
See application file for complete search history.

(56) References Cited

U.S. PATENT DOCUMENTS
2016/0326561 A1* 11/2016 Lohitharn ............... C12P 19/44

FOREIGN PATENT DOCUMENTS
| WO | WO-200029604 | * | 5/2000 |
| WO | WO-2014039940 A1 | * | 3/2014 |

OTHER PUBLICATIONS
Foley et al. Derivation and synthesis of renewable surfactants. Chem. Soc. Rev. 2012, 41, 1499-1518.*

* cited by examiner

*Primary Examiner* — Iqbal H Chowdhury
(74) *Attorney, Agent, or Firm* — Renner, Kenner, Greive, Bobak, Taylor & Weber

(57) ABSTRACT

In various aspects, the present invention is directed to a scalable method of producing rhamnolipids by bacterial fermentation with higher product concentrations, yields and productivities and preventing excessive foaming during the cell growth phase when the cell respiration rate is higher. It has been found that by slowing the growth rate of the bacteria by altering the ratio of the nitrogen source to the non-nitrogen source in the initial fermentation medium and supplementing the nitrogen source, excessive foaming in the growth phase can be prevented. Further, by using the non-nitrogen source as the limiting nutrient that initiates the stationary phase and then supplementing fermentation broth with the nitrogen and carbon sources, the length of the standing phase, and with it the time during which rhamnolipid production occurs can be greatly extended.

33 Claims, 8 Drawing Sheets

PRODUCTION OF FERMENTATION PRODUCTS CONTAINING RHAMNOLIPIDS

CROSS REFERENCE TO RELATED APPLICATIONS

This application claims the benefit of U.S. provisional patent application Ser. No. 62/716,660 entitled "Production of Fermentation Products Containing Rhamnolipids," filed Aug. 9, 2019, and incorporated herein by reference in its entirety.

FIELD OF THE INVENTION

One or more embodiments of the present invention relates to a method for producing rhamnolipids. In certain embodiments, methods of producing rhamnolipids using bacterial fermentation that reduce foaming and produce rhamnolipids at high concentrations.

BACKGROUND OF THE INVENTION

Rhamnolipids are a group of nontoxic, biodegradable and environmentally friendly biosurfactants. Rhamnolipid congeners produced by microbial fermentations generally have the molecular structures that include one or two rhamnose residues linked to one or two β-hydroxyl fatty acids. Accordingly, rhamnolipids are commonly classified into four groups depending on its respective numbers of rhamnose and fatty acid residues. The most representative structures of these four rhamnolipid groups are L-rhamnosyl-β-hydroxydecanoate (R-C10), L-rhamnosyl-β-hydroxydecanoyl-β-hydroxydecanoate (R-C10-C10), L-rhamnosyl-L-rhamnosyl-β-hydroxydecanoate (R-R-C10), and L-rhamnosyl-L-rhamnosyl-β-hydroxydecanoyl-β-hydroxydecanoate (R-R-C10-C10).

As will be understood by those of skill in the art, rhamnolipids may be produced by fermentation of one or more carbon containing substrate, such as vegetable oils. About 60 different rhamnolipids have been reported to be produced by fermentation using *Pseudomonas aeruginosa*, *Pseudoxanthomonas* sp., *Myxococcus* sp., *Enterobacter* sp., *Burkholderia* sp., *Nocardioides* sp., *Acinetobacter calcoaceticus*, *Renibacterium salmoninarum*, *Cellulomonas cellulans*, *Tetragenococcus koreensis* and other species of bacteria.

Rhamnolipids are known to have various attractive properties, including, without limitation, biodegradability, biocompatibility, low or no toxicity, surface-activities, detergency particularly for cleaning oil and grease from objects, emulsification, solubilization, low critical micelle concentrations, pH responsiveness, antimicrobial activities, biopesticidal properties, antifouling properties, soil remediation of insoluble substances such as hydrocarbons and of inorganic pollutants such as heavy metals, and wound healing properties. Accordingly, there have been many applications reported, patented or proposed for rhamnolipid-containing products, sometimes simply referred to as "natural biosurfactant products" or something similar. Full commercial realization of many of these properties and/or applications, however, will require acceptable process economics for the rhamnolipid production, which have not been realized using prior art production methods.

Despite these attractive properties and existing or potential applications, rhamnolipid commercialization still suffers from high production costs and less stable operation. There are multiple problems both in the upstream fermentation processes and the downstream collection and purification of the fermentation products containing rhamnolipids that contribute to these high production costs and less stable operation. As will be understood, the main issues controlling the process economics for production of fermentation products are productivity, conversion, and product concentration. As used herein, the term "productivity" refers to the production rate per unit reactor (or facility) volume, for example, in the following unit of measurement: grams (g) of product (here, rhamnolipids) per hour (h) per liter (L). For producing a desired annual amount of the product to meet market demand, the higher the productivity, the smaller the reactor and facilities size required to make it; thus, the lower the capital investment (fixed costs) and labor, utilities and management costs (operating or running costs).

The "conversion," as the term is used herein, refers to the conversion of a specific substrate to the product. In most cases described herein, the substrate considered for conversion is the carbon source. So, the higher the conversion, the lower amount of substrate required to produce a desired amount of product. Conversion thus controls the raw material costs for making the product, particularly if some of the fermentation substrates are relatively expensive and the products are of lower unit market value, as would be the case, for example, where the rhamnolipids are to be used as ingredients in laundry detergents. High product concentration means the desired amount of product is harvested from a relatively small volume of fermentation broth. Accordingly, if the product concentration is high, the downstream collection cost is lower because smaller equipment and facilities and likely shorter processing time are required to handle the smaller broth volume. Further, a smaller amount of spent or waste water is generated, which requires costs for recovery or treatment before disposal. For fermentation products, the downstream processing costs are often higher than the upstream fermentation costs.

In addition to these factors, i.e., productivity, conversion and product concentration, the stability of process operation is very important to minimize downtime and accidents, minimize additional reactor/facilities set aside to handle the instability, and ensure production efficiency and schedule. One such source of instability in the production of rhamnolipids is excessive foaming. As will be apparent, a high cell concentration is desired during the fermentation process for achieving high volumetric productivity. However, the bacteria producing the rhamnolipids in these processes need oxygen to live and particularly to grow aerobically. As the cell respiration rate is directly proportional to the cell growth rate, building up a high concentration of rapidly growing cells often leads to excessive foam formation due to the high aeration rates required to meet the cells' respiration demand. Formation of stable foam can lead to problems in operation and control of the process and potential/attempted remedies like using larger reaction vessels, adding a second overflow vessel, using lower cell concentrations, and/or adding defoaming agents are all known to increase productions costs.

Since some rhamnolipid-producing bacteria (such as the *P. aeruginosa* used in our work here) can also use nitrate and nitrite as the external oxidant in place of oxygen for respiration, attempts have been made to avoiding foaming and intensive mechanical agitation (the latter consumes energy) by relying upon nitrate and nitrite as the external oxidant in place of oxygen. These systems, however, require complex process designs to make use of the denitrification mechanism because nitrate/nitrite are inhibitory/toxic to the rhamnolipid producing bacteria at higher concentrations and the nitrate/nitrite addition rate must continuously change depending on the consumption rate by the rhamnolipid producing bacteria. Moreover, the addition and consumption of the nitrate/nitrite also cause significant pH changes of the fermentation broths. These systems have, for these and other reasons, generally been found to be unworkable for large-scale commercial rhamnolipid production.

As set forth above, another problem with the present state of rhamnolipid production is the high cost of downstream processing to recover purified rhamnolipid from the fermentation broth. These costs can be greatly reduced, however, if the product (rhamnolipid) concentration in the harvested fermentation broth is increased, as discussed above. The highest product concentrations for known processes for producing rhamnolipids by fermentation are known to be about 70 g/L.

Further, it has been found that the productivity of rhamnolipid in long fermentation runs is often inconsistent and tends to decline during late stationary phase. It is believed that the decline in rhamnolipid productivity during long fermentation runs in known systems is likely associated with the cells' long-term maintenance metabolism in the nitrogen depleted conditions. This drop in productivity results in a shortening of the fermentation run that increases overall reactor downtime and labor for cleaning and refilling the fermentation equipment and a relatively low product concentration.

Accordingly, what is needed in the art is a scalable method for production of rhamnolipids by bacterial fermentation with high conversion, productivity and product concentration, but without excessive foaming.

SUMMARY OF THE INVENTION

In one or more embodiments, the present invention provide a scalable method of producing rhamnolipids by non-nitrogen source limited bacterial fermentation with high product concentrations and with limited foaming during the cell growth phase. It has been found that by slowing the grown rate of the bacteria by altering the ratio of the nitrogen source to the non-nitrogen source in the fermentation medium, excessive foaming in the growth phase can be prevented It has also been found that by using the non-nitrogen source as the limiting nutrient that initiates the stationary phase and then supplementing fermentation broth with the nitrogen and carbon sources, the length of the stationary phase, and with it the time during which rhamnolipid production occurs can be greatly extended. This results in much higher product concentrations than were possible with prior art methods of rhamnolipid production, significantly lowering overall production costs since the lower volume of fermentation broth lowers downstream collection costs because smaller equipment and facilities can be used, shorter processing times are required to handle the smaller broth volume, and a smaller amount of spent or waste water is generated, which requires costs for recovery or treatment before disposal.

In a first aspect, the present invention is directed to a method for improving production rates, conversions and concentrations of rhamnolipids during fermentation-based rhamnolipid production comprising: growing a rhamnolipid producing bacteria in a fermentation broth comprising at least one carbon source, at least one nitrogen source and at least one non-nitrogen source; and after the growth of the rhamnolipid producing bacteria is substantially complete, adding one or more additional quantities of a nitrogen source to maintain production of the rhamnolipids. In one or more of these embodiments, each of the one or more additional quantities of the nitrogen source is added in an amount sufficient to maintain production of rhamnolipids but not sufficient to permit the rhamnolipid producing bacteria to produce non-rhamnolipid byproducts.

In one or more embodiments, the method for improving production rates, conversions and concentrations of rhamnolipids during fermentation-based rhamnolipid production of the present invention includes any one or more of the above referenced embodiments of the first aspect of the present invention wherein determining a quantity of each one of the at least one carbon source, at least one nitrogen source, and non-nitrogen source necessary to grow the rhamnolipid producing bacteria to a desired cell concentration; forming an initial fermentation medium comprising some or all of the quantity of the at least one carbon source necessary to grow the rhamnolipid producing bacteria to the desired cell concentration, some or all of the quantity of the non-nitrogen source necessary to grow the rhamnolipid producing bacteria to the desired cell concentration, and a first portion the quantity of the at least one nitrogen source necessary to grow the rhamnolipid producing bacteria to the desired cell concentration; adding the rhamnolipid producing bacteria to the initial fermentation medium to form the fermentation broth and growing the rhamnolipid producing bacteria until the first portion of the at least one nitrogen source has been substantially consumed; and adding any remaining carbon source and non-nitrogen source and gradually adding a remaining portion of the quantity of the at least one nitrogen source to the fermentation broth to continue growing the rhamnolipid producing bacteria until the remaining portion of the quantity of the at least one nitrogen source has been substantially consumed or growth of the rhamnolipid producing bacteria stops. In some of these embodiments all of the carbon source and non-nitrogen source necessary to grow the rhamnolipid producing bacteria to the desired cell concentration are added to the initial fermentation medium. In one or more of these embodiments, the fermentation medium comprises phosphorus, sulfur, potassium, sodium, calcium, magnesium, chloride, iron, manganese, zinc, boron, cobalt, copper, and molybdenum.

In one or more embodiments, the method for improving production rates, conversions and concentrations of rhamnolipids during fermentation-based rhamnolipid production of the present invention includes any one or more of the above referenced embodiments of the first aspect of the present invention wherein the limiting nutrient in the fermentation broth is the non-nitrogen source. In one or more embodiments, the method for improving production rates, conversions and concentrations of rhamnolipids during fermentation-based rhamnolipid production of the present invention includes any one or more of the above referenced embodiments of the first aspect of the present invention wherein the limiting nutrient in the fermentation broth is the nitrogen source.

In one or more embodiments, the method for improving production rates, conversions and concentrations of rhamnolipids during fermentation-based rhamnolipid production of the present invention includes any one or more of the above referenced embodiments of the first aspect of the present invention further comprising adding one or more additional quantities of a nitrogen source to the fermentation broth during the step of growing. In one or more of these embodiments, the fermentation broth comprises phosphorus, sulfur, potassium, sodium, calcium, magnesium, chloride, iron, manganese, zinc, boron, cobalt, copper, and molybdenum. In one or more embodiments, the method for improving production rates, conversions and concentrations of rhamnolipids during fermentation-based rhamnolipid production of the present invention includes any one or more of the above referenced embodiments of the first aspect of the present invention wherein the rate of foam formation of the rhamnolipid producing bacteria in the step of growing is controlled by controlling the rate at which the one or more additional quantities of a nitrogen source are added to the fermentation broth during the step of growing. In one or more embodiments, the method for improving production rates, conversions and concentrations of rhamnolipids during fermentation-based rhamnolipid production of the present invention includes any one or more of the above referenced embodiments of the first aspect of the present invention wherein the cell concentration of the rhamnolipid producing bacteria in the step of growing is controlled by controlling the rate at which the one or more additional quantities of a nitrogen source are added to the fermentation broth during the step of growing.

In one or more embodiments, the method for improving production rates, conversions and concentrations of rhamnolipids during fermentation-based rhamnolipid production of the present invention includes any one or more of the above referenced embodiments of the first aspect of the present invention wherein the additional quantity of a nitrogen source is added to the fermentation broth in batches. In one or more embodiments, the method for improving production rates, conversions and concentrations of rhamnolipids during fermentation-based rhamnolipid production of the present invention includes any one or more of the above referenced embodiments of the first aspect of the present invention wherein the additional quantity of a nitrogen source is added in batches of from about 5% to about 75% by weight of the amount of the nitrogen source in the fermentation broth, every about 12 hours to about 48 hours. In one or more embodiments, the method for improving production rates, conversions and concentrations of rhamnolipids during fermentation-based rhamnolipid production of the present invention includes any one or more of the above referenced embodiments of the first aspect of the present invention wherein the additional quantity of a nitrogen source is added substantially continuously in an amount of from about 5% to about 75% by weight of the amount of the nitrogen source in the fermentation broth, over every period of from about 12 to about 48 hours.

In one or more embodiments, the method for improving production rates, conversions and concentrations of rhamnolipids during fermentation-based rhamnolipid production of the present invention includes any one or more of the above referenced embodiments of the first aspect of the present invention wherein the additional quantity of a nitrogen source is added to the fermentation broth substantially continuously.

In one or more embodiments, the method for improving production rates, conversions and concentrations of rhamnolipids during fermentation-based rhamnolipid production of the present invention includes any one or more of the above referenced embodiments of the first aspect of the present invention wherein the rhamnolipid producing bacteria is selected from the group consisting of *Pseudomonas aeruginosa, Pseudomonas chlororaphis, Pseudomonas putida, Pseudomonas fluorescens, Pseudoxanthomonas* sp., *Myxococcus* sp., *Enterobacter* sp., *Burkholderia* sp., *Burkholderia thailandensis, Burkholderia pseudomallei, Nocardioides* sp., *Acinetobacter calcoaceticus, Renibacterium salmoninarum, Cellulomonas cellulans, Tetragenococcus koreensis*, and combinations thereof. In one or more embodiments, the method for improving production rates, conversions and concentrations of rhamnolipids during fermentation-based rhamnolipid production of the present invention includes any one or more of the above referenced embodiments of the first aspect of the present invention wherein the rhamnolipid producing bacteria is *Pseudomonas aeruginosa*. In one or more embodiments, the method for improving production rates, conversions and concentrations of rhamnolipids during fermentation-based rhamnolipid production of the present invention includes any one or more of the above referenced embodiments of the first aspect of the present invention wherein the conversion of the carbon source to rhamnolipids after the growth of the rhamnolipid producing bacteria is substantially complete is from about 50% to about 90% by weight.

In a second aspect, the present invention is directed to a process for producing rhamnolipids by bacterial fermentation comprising: preparing a bacterial seed culture comprising at least one rhamnolipid producing bacteria; preparing a fermentation medium in a suitable fermentation vessel, the fermentation medium comprising a carbon source, a nitrogen source, and a non-nitrogen source containing phosphorus, sulfur, potassium, sodium, calcium, magnesium, chloride, iron, manganese, zinc, boron, cobalt, copper, and molybdenum; adding the bacterial seed culture and at least one of air and oxygen to the fermentation medium to form a fermentation broth; growing the rhamnolipid producing bacteria in the fermentation broth; periodically adding additional quantities of the nitrogen source to allow the rhamnolipid producing bacteria to grow until the non-nitrogen source is substantially consumed, wherein rhamnolipid producing bacteria growth substantially stops and rhamnolipids are produced; periodically supplementing the nitrogen source to prolong rhamnolipid production until the rhamnolipid concentration in the fermentation broth reaches a concentration of from about 50 g/L to about 200 g/L; removing some or all of the fermentation broth and harvesting the rhamnolipids contained therein. In one or more of these embodiments, the step of removing comprises removing from about 20% to about 95% of the volume of the fermentation broth and harvesting the rhamnolipids contained therein, the method further comprising: replacing the volume of the fermentation broth removed in the step of removing with a volume of the fermentation medium; repeating these steps; and harvesting the rhamnolipids contained in the resulting fermentation broth. In one or more embodiments, the process for producing rhamnolipids by bacterial fermentation of the present invention includes any one or more of the above referenced embodiments of the second aspect of the present invention wherein the step of repeating is repeated from 1 to 100 times.

In one or more embodiments, the process for producing rhamnolipids by bacterial fermentation of the present invention includes any one or more of the above referenced embodiments of the second aspect of the present invention wherein the rhamnolipid producing bacteria is selected from the group consisting of *Pseudomonas aeruginosa, Pseudomonas chlororaphis, Pseudomonas putida, Pseudomonas fluorescens, Pseudoxanthomonas* sp., *Myxococcus* sp., *Enterobacter* sp., *Burkholderia* sp., *Burkholderia thailandensis, Burkholderia pseudomallei, Nocardioides* sp., *Acinetobacter calcoaceticus, Renibacterium salmoninarum, Cellulomonas cellulans, Tetragenococcus koreensis*, and combinations thereof. In one or more embodiments, the process for producing rhamnolipids by bacterial fermentation of the present invention includes any one or more of the above referenced embodiments of the second aspect of the present invention wherein the rhamnolipid producing bacteria is a strain of Pseudomonas aeruginosa.

In one or more embodiments, the process for producing rhamnolipids by bacterial fermentation of the present invention includes any one or more of the above referenced embodiments of the second aspect of the present invention wherein the carbon source is selected from the group consisting of vegetable oil, soybean oil, rapeseed oil, cocoa butter, olive oil, rice bran oil, palm oil, animal fat, glycerol, fatty acids, used cooking oil, waste oil, waste grease, glucose, fructose, sucrose, lactose, maltose, corn syrup, corn molasses, soy molasses, carbohydrates, materials containing carbohydrates, glycerides, fatty acids, glycerol, and combinations thereof. In one or more embodiments, the process for producing rhamnolipids by bacterial fermentation of the present invention includes any one or more of the above referenced embodiments of the second aspect of the present invention wherein the nitrogen source is selected from the group consisting of $NH_4NO_3$, $NH_4Cl$, $NH_4OH$ (ammonia water), $(NH_4)_2SO_4$, $(NH_4)_3PO_4$, $(NH_4)_2HPO_4$, $(NH_4)H_2PO_4$, ammonium salts, $NaNO_3$, $KNO_3$, $Ca(NO_3)_2$, nitrate salts, urea, yeast extract, peptone, tryptone, protein hydrolysates containing amino acids and/or peptides, soybean meal, soybean flour, soybean protein, seed proteins, animal milks, materials containing ammonium, amine, nitrate, amino acids, peptides, proteins, and combinations thereof.

In one or more embodiments, the process for producing rhamnolipids by bacterial fermentation of the present invention includes any one or more of the above referenced embodiments of the second aspect of the present invention further comprising controlling foam production in the step of periodically adding additional quantities of the nitrogen source by varying the rate at which the additional quantities of the nitrogen source are added to the fermentation broth.

In one or more embodiments, the process for producing rhamnolipids by bacterial fermentation of the present invention includes any one or more of the above referenced embodiments of the second aspect of the present invention wherein the fermentation broth in the step of growing has a dissolved oxygen content of from about 1% to 100% and an air saturation of from about 0.08 mg/L to 10 mg/L. In one or more embodiments, the process for producing rhamnolipids by bacterial fermentation of the present invention includes any one or more of the above referenced embodiments of the second aspect of the present invention wherein the fermentation broth in the step of growing has a pH of from about 5 to about 8.5. In one or more embodiments, the process for producing rhamnolipids by bacterial fermentation of the present invention includes any one or more of the above referenced embodiments of the second aspect of the present invention wherein the temperature of the fermentation broth in the step of growing is from about 15° C. to about 40° C.

In one or more embodiments, the process for producing rhamnolipids by bacterial fermentation of the present invention includes any one or more of the above referenced embodiments of the second aspect of the present invention wherein the nitrogen source in the step of periodically supplementing the nitrogen source to prolong rhamnolipids production is supplemented in batches at a rate of from about 5% to about 75% by weight of the amount of the nitrogen source used to form the fermentation medium every about 12 to about 48 hours. In one or more embodiments, the process for producing rhamnolipids by bacterial fermentation of the present invention includes any one or more of the above referenced embodiments of the second aspect of the present invention wherein the nitrogen source in the step of periodically supplementing the nitrogen source to prolong rhamnolipids production is continuously supplemented to provide from about 2.5% to about 150% by weight of the amount of the nitrogen source used to form the fermentation medium every about 24 hours.

In one or more embodiments, the process for producing rhamnolipids by bacterial fermentation of the present invention includes any one or more of the above referenced embodiments of the second aspect of the present invention wherein the nitrogen source in the step of periodically supplementing the nitrogen source and the carbon source to prolong rhamnolipids production are periodically supplemented until the rhamnolipid concentration in the fermentation broth reaches a concentration of at least 75 g/L. In one or more embodiments, the process for producing rhamnolipids by bacterial fermentation of the present invention includes any one or more of the above referenced embodiments of the second aspect of the present invention wherein from about 50% to about 90% by weight of the carbon source is converted into rhamnolipids.

In a third aspect, the present invention is directed to a process for producing a fermentation broth having a concentration of rhamnolipids of 75 g/L or more comprising: prepare a bacterial seed culture comprising a strain of Pseudomonas aeruginosa bacteria; preparing a fermentation medium in a suitable fermentation vessel equipped to agitate and aerate a fermentation broth, the fermentation medium comprising a carbon source selected from the group consisting of vegetable oil, soybean oil, rapeseed oil, cocoa butter, olive oil, rice bran oil, palm oil, animal fat, glycerol, fatty acids, used cooking oil, waste oil, waste grease, glucose, fructose, sucrose, lactose, maltose, corn syrup, corn molasses, soy molasses, carbohydrates, materials containing carbohydrates, glycerides, fatty acids, glycerol, and combinations thereof, a nitrogen source selected from the group consisting of $NH_4NO_3$, $NH_4Cl$, $NH_4OH$ (ammonia water), $(NH_4)_2SO_4$, $(NH_4)_3PO_4$, $(NH_4)_2HPO_4$, $(NH_4)H_2PO_4$, ammonium salts, $NaNO_3$, $KNO_3$, $Ca(NO_3)_2$, nitrate salts, urea, yeast extract, peptone, tryptone, protein hydrolysates containing amino acids and/or peptides, soybean meal, soybean flour, soybean protein, seed proteins, animal milks, materials containing ammonium, amine, nitrate, amino acid, peptides proteins, and combinations thereof, and a non-nitrogen source containing phosphorus, sulfur, potassium, sodium, calcium, magnesium, chloride, iron, manganese, zinc, boron, cobalt, copper, and molybdenum, wherein the non nitrogen source is the limiting nutrient; adding the bacterial seed culture to the fermentation medium to form a fermentation broth; agitating and aerating the fermentation broth at a temperature of from about 15° C. to about 40° C. to grow the Pseudomonas aeruginosa bacteria in the fermentation broth; periodically adding an additional quantity of the nitrogen source in an amount of from about 0% to about 100% by weight of the amount of the nitrogen source used to form the fermentation medium every about 1 second to about 180 minutes to allow the Pseudomonas aeruginosa bacteria to grow until the non-nitrogen source is substantially consumed, wherein the growth of the Pseudomonas aeruginosa bacteria substantially stops and the fermentation broth enters a phase wherein rhamnolipids are produced; supplementing the nitrogen source at a rate of from about 5% to about 75% by weight of the amount of the nitrogen source used to grow the Pseudomonas aeruginosa bacteria every about 12 to about 48 hours to maintain substantially non-decreasing rate of rhamnolipid production for from 24 hours to about 600 hours until the rhamnolipid concentration in the fermentation broth reaches a concentration of at least about 75 g/L; and removing some or all of the fermentation broth and harvesting the rhamnolipids contained therein. In one or more of these embodiments, the nitrogen source in the step of supplementing the nitrogen source is added continuously.

In one or more embodiments, the process for producing rhamnolipids of 75 g/L or more of the present invention includes any one or more of the above referenced embodiments of the second aspect of the present invention wherein the nitrogen source in the step of supplementing the nitrogen source is added in batches.

In one or more embodiments, the process for producing rhamnolipids of 75 g/L or more of the present invention includes any one or more of the above referenced embodiments of the second aspect of the present invention wherein the step of removing some or all of the fermentation broth comprises removing from about 20% to about 95% of the fermentation broth by volume and harvesting the rhamnolipids contained therein, the method further comprising: replacing the volume of the fermentation broth removed in the step of removing with a volume of the fermentation medium; repeating these steps; and harvesting the rhamnolipids contained in the fermentation broth. In one or more embodiments, the process for producing rhamnolipids of 75 g/L or more of the present invention includes any one or more of the above referenced embodiments of the second aspect of the present invention wherein the rhamnolipid concentration in the fermentation broth reaches a concentration of from about 75 g/L to about 200 g/L.

In a fourth aspect, the present invention is directed to a method for reducing or eliminating excessive foaming during the growth phase of fermentation-based rhamnolipid production comprising: determining a quantity of each one of the at least one carbon source, at least one nitrogen source, and non-nitrogen source necessary to grow the rhamnolipid producing bacteria to a desired cell concentration; forming an initial fermentation medium comprising some or all of the quantity of the at least one carbon source necessary to grow the rhamnolipid producing bacteria to the desired cell concentration, some or all of the quantity of the non-nitrogen source necessary to grow the rhamnolipid producing bacteria to the desired cell concentration, and a first portion the quantity of the at least one nitrogen source necessary to grow the rhamnolipid producing bacteria to the desired cell concentration, wherein the initial fermentation medium comprises phosphorus, sulfur, potassium, sodium, calcium, magnesium, chloride, iron, manganese, zinc, boron, cobalt, copper, and molybdenum; adding the rhamnolipid producing bacteria to the initial fermentation medium to form the fermentation broth and growing the rhamnolipid producing bacteria until the first portion of the at least one nitrogen source has been substantially consumed; and adding any remaining carbon source and non-nitrogen source to the fermentation broth and gradually adding a remaining portion of the quantity of the at least one nitrogen source to the fermentation broth, to continue growing the rhamnolipid producing bacteria at a rate that is slow enough to reduce or substantially eliminate excessive foaming until the remaining portion of the quantity of nitrogen source has been substantially consumed or growth of the rhamnolipid producing bacteria stops.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

Figure 1:
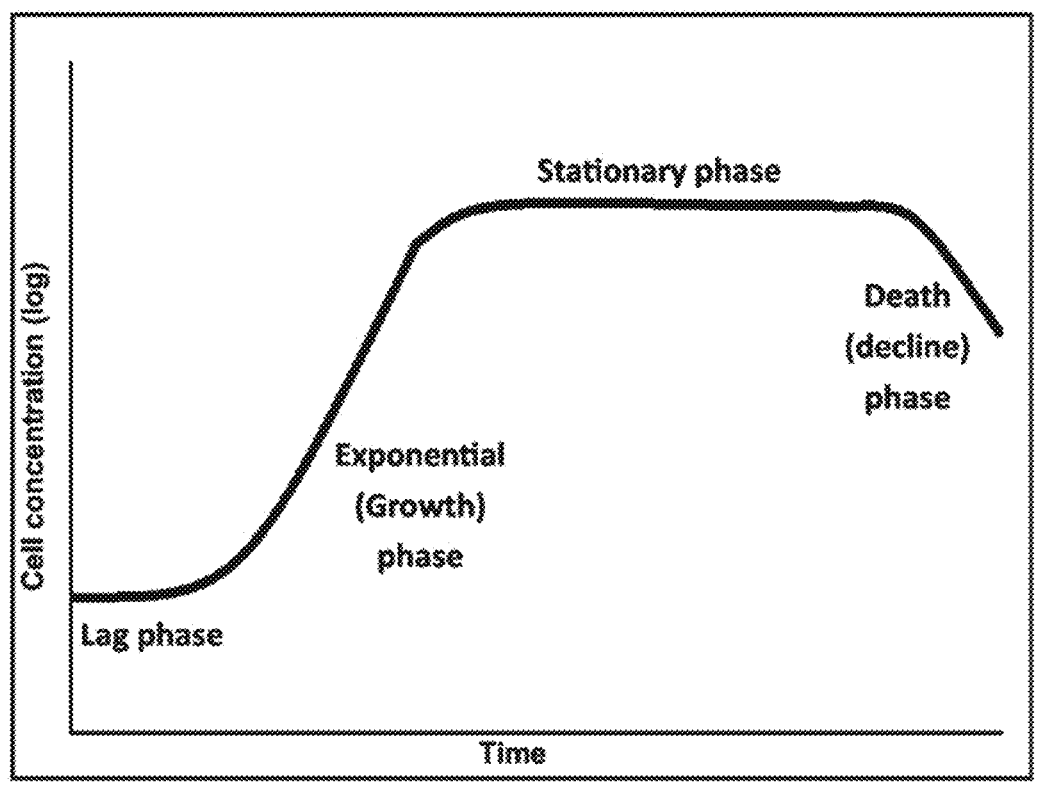
FIG. 1 is a graph showing bacterial growth in batch fermentation over time for a representative rhamnolipid producing bacteria.

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the disclosure herein is for describing particular embodiments only and is not intended to be limiting of the disclosure.

In various aspects, the present invention is directed to a scalable method of producing rhamnolipids by bacterial fermentation with high product concentrations and limited foaming during the cell growth phase when the cell respiration rate is higher. It has been found that by slowing the grown rate of the bacteria by altering the ratio of the nitrogen source to the non-nitrogen source in the initial fermentation medium and supplementing with the nitrogen source, excessive foaming in the growth phase can be prevented. It has also been found that by using the non-nitrogen source as the limiting nutrient that initiates the standing phase and then supplementing fermentation broth with the nitrogen and carbon sources, the length of the stationary phase, and with it the time during which rhamnolipid production occurs can be greatly extended. This results in much higher product concentrations than were possible with prior art methods of rhamnolipid production, significantly lowering overall production costs since the lower volume of fermentation broth lowers downstream collection costs because smaller equipment and facilities can be used, shorter processing times are required to handle the smaller broth volume, and a smaller amount of spent or waste water is generated, which requires costs for recovery or treatment before disposal.

As set forth above, rhamnolipids are biosurfactants produced by certain species of bacteria, with *Pseudomonas aeruginosa* being the most productive species, having several promising industrial applications. In various applications, rhamnolipids can be used as emulsifiers, detergents, foaming agents, dispersants, antimicrobial agents, and anti-adhesive solutions. Several environmental applications of rhamnolipids such as bioremediation, soil washing, and enhanced oil recovery have been reported. Rhamnolipids have also received attention for use as antimicrobial agents for controlling spread of infection by phytopathogenic fungi such as *Phytophthora* sp., *Pythium* sp., *Plasmopara* sp., and *Colletotrichum* sp. Full commercial realization of many of these applications requires acceptable process economics for the rhamnolipid production, which have not been possible using prior art production methods. As set forth above, high product productivity, conversion and product concentration, as well as simple and reproducible operations are important for economic feasibility of rhamnolipids.

The following terms may have meanings ascribed to them below, unless specified otherwise. As used herein, the terms "comprising", "to comprise" and the like do not exclude the presence of further elements or steps in addition to those listed in a claim. Similarly, the terms "a," "an" or "the" before an element or feature does not exclude the presence of a plurality of these elements or features, unless the context clearly dictates otherwise. Further, the term "means" used many times in a claim does not exclude the possibility that two or more of these means are actuated through a single element or component.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term "about."

It should be also understood that the ranges provided herein are a shorthand for all of the values within the range and, further, that the individual range values presented herein can be combined to form additional non-disclosed ranges. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. Further, any compositions or methods provided herein can be combined with one or more of any of the other compositions and methods provided herein. The fact that given features, elements or components are cited in different dependent claims does not exclude that at least some of these features, elements or components may be used in combination together.

As will be appreciated by those of skill in the art, rhamnolipids are a class of glycolipids known to be produced by a group of rhamnolipid producing bacteria. Rhamnolipids generally have one (mono-rhamnolipids) or two (di-rhamnolipids) rhamnose groups connected to one or two fatty acids, which vary in carbon chain length and may be branched. Rhamnolipid congeners produced by microbial fermentations generally have the molecular structures that include one or two rhamnose residues linked to one or two β-hydroxyl fatty acids, having from about 4 to about 20 (more commonly from about 8 to about 16) carbon atoms in each β-hydroxyl fatty acid chain.

As will be appreciated by those of skill in the art, rhamnolipids are commonly classified into four groups depending on its respective numbers of rhamnose and fatty acid residues. In this nomenclature system, each rambose is designated "R" (i.e. "R" for mono-rhamnolipids and "R-R" for di-rhamnolipids) and then each fatty acid residue is described by its carbon length (i.e. "C10" for one fatty acid residue of 10 carbons in length and "C10-C10" for two fatty acid residues of 10 carbons in length). A di-rhamnolipid having two fatty acid residues of 10 carbons in length (L-rhamnosyl-L-rhamnosyl-β-hydroxydecanoyl-β-hydroxydecanoate) would, therefore, be designated "R-R-C10-C10." Further, the number of unsaturations (C-C double bonds) in the fatty acid chain is shown this nomenclature system after a colon. So, a rhamnolipid identified as R-R-C10-C12:1 would be a di-rhamnolipid having a first fatty acid residue of 10 carbons in length and a second fatty acid residue of 12 carbons in length having one unsaturation.

Typical rhamnolipids produced by bacterial fermentation-based rhamnolipid production may include, without limitation, L-rhamnosyl-β-hydroxydecanoate (R-C10), L-rhamnosyl-β-hydroxydecanoyl-β-hydroxydecanoate (R-C10-C10), L-rhamnosyl-L-rhamnosyl-β-hydroxydecanoate (R-R-C10), and L-rhamnosyl-L-rhamnosyl-β-hydroxydecanoyl-β-hydroxydecanoate (R-R-C10-C10), R-C8, R-C8-C8, R-R-C8, R-R-C8-C8, R-C8-C10, R-C10-C8, R-R-C8-C10, R-R-C10-C8, R-C10, R-C10-C10, R-R-C10, R-R-C10-C10, R-C10-C12, R-C12-C10, R-R-C10-C12, R-R-C12-C10, R-C10-C12:1, R-C12:1-C10, R-R-C10-C12:1, and R-R-C12:1-C10. In one or more embodiments, rhamnolipids produced by the methods of the present invention include, without limitation, L-rhamnosyl-β-hydroxydecanoate (R-C10), L-rhamnosyl-β-hydroxydecanoyl-β-hydroxydecanoate (R-C10-C10), L-rhamnosyl-L-rhamnosyl-β-hydroxydecanoate (R-R-C10), and L-rhamnosyl-L-rhamnosyl-β-hydroxydecanoyl-β-hydroxydecanoate (R-R-C10-C10). As will be appreciated by those of skill in the art, the specific rhamnolipid or mixture of rhamnolipids produced will depend upon numerous factors including but limited to, the particular rhamnolipid producing bacteria selected, the specific carbon source and non-carbon sources used, the growth-limiting substrate employed which, when exhausted, causes the cells to enter into the stationary phase where active rhamnolipid production typically occurs, the duration of fermentation, the cell growth rate during the rhamnolipid-producing period, and the fermentation conditions including, but not limited to, temperature, pH, mixing device, agitation speed and associated shear, aeration rate, dissolved oxygen concentration, and salinity.

Numerous rhamnolipid producing bacteria are known in the art, and one of ordinary skill in the art will be able to select a suitable rhamnolipid producing bacteria without undue experimentation. Suitable rhamnolipid producing bacteria may include, without limitation, *Pseudomonas aeruginosa, Pseudomonas chlororaphis, Pseudomonas putida, Pseudomonas fluorescens, Pseudoxanthomonas* sp., *Myxococcus* sp., *Enterobacter* sp., *Burkholderia* sp., *Burkholderia thailandensis, Burkholderia pseudomallei, Nocardioides* sp., *Acinetobacter calcoaceticus, Renibacterium salmoninarum, Cellulomonas cellulans, Tetragenococcus koreensis*, and various strains and combinations thereof. In some embodiments, the rhamnolipid producing bacteria is *Pseudomonas aeruginosa*. In some embodiments, the rhamnolipid producing bacteria used in the present invention may comprise two or more species of rhamnolipid producing bacteria, although this is not preferred since it can significantly add to the complexity of the production. In some embodiments, the rhamnolipid producing bacteria used in the present invention may comprise more than one strain of a species of rhamnolipid producing bacteria.

As will be understood by those in the art, all cells need energy source to live and some, including all the bacteria used for rhamnolipid production identified above, rely on organic (carbon-based) substances, i.e., a carbon source, as their energy source. In addition to the energy source, individual cells need small amounts of a nitrogen source and a non-nitrogen, non-carbon collection of certain other nutrients and trace elements (referred to herein as the non-nitrogen source) for long-term survival. While this is not critical for short-term survival, in the long-term, bacteria cells can lose critical enzymes and other cellular materials due to inevitable degradation. While bacteria cells generally have the ability to resynthesize these materials using their degradation products, the recycling synthesis cannot be 100%. Accordingly, the presence of small amounts of critical nutrients allows the cells to make new enzymes and other critical cellular materials, making up for the incomplete recycling during long-term survival.

Moreover, all cells need an energy source, a carbon source, a nitrogen source and these non-carbon non-nitrogen sources ("non N source") to grow. For some cells (including all the bacteria used for rhamnolipid production) that rely on organic (carbon-based) substances as their energy source, the carbon source can serve as not only the energy source but also as a source of carbon (material) for synthesizing more cell biomass (i.e., to grow). All cells also need a nitrogen source and the non-N source for building more cell biomass (to grow); the amounts of these materials required for growth are much larger than the amounts for maintaining long-term survival.

As used herein, the terms "carbon source," "C-source," or "C source" are used interchangeably to refer to nutrients containing carbon that are used by the bacteria as an energy source and as a source of carbon (material) for synthesizing more cell biomass (i.e., to grow). In various embodiments, the carbon source may include, but is not limited to, vegetable oils, soybean oil, rapeseed oil, cocoa butter, olive oil, rice bran oil, palm oil, animal fat, glycerol, fatty acids, used cooking oil, waste oil, waste grease, glucose, fructose, sucrose, lactose, maltose, corn syrup, corn molasses, soy molasses, carbohydrates, and materials containing carbohydrates, glycerides, fatty acids, glycerol, or combinations thereof. In the methods of producing rhamnolipids of the present invention, the carbon source is consistently supplied to the fermentation vessel and is not used as the limiting nutrient.

As used herein, the term "substrate" refers generally to any nutrient consumed by an organism or reacted with enzymes produced by an organism. To the extent that the term is used in connection with a specific "purpose" or "functional role," it may be used to describe a particular nutrient being used or consumed, such as a "carbon substrate" or a "nitrogen substrate." Here, if the word "substrate" is used alone, it either loosely refers to all or any nutrients involved or (specifically but implicitly) the carbon-source substrate, depending upon the context.

As used herein, the terms "nitrogen source," "N-source," or "N source" are used interchangeably to refer to nutrients containing nitrogen that are used by the bacteria to synthesize enzymes, nucleic acids, and other nitrogen-containing cellular materials. In one or more embodiments, the nitrogen source may be organic, inorganic, or a combination thereof. In various embodiments, the nitrogen source may include, but is not limited to, $NH_4NO_3$, $NH_4Cl$, $NH_4OH$ (ammonia water), $(NH_4)_2SO_4$, $(NH_4)_3PO_4$, $(NH_4)_2HPO_4$, $(NH_4)H_2PO_4$, ammonium salts, $NaNO_3$, $KNO_3$, $Ca(NO_3)_2$, nitrate salts, urea, yeast extract, peptone, tryptone, protein hydrolysates containing amino acids and/or peptides, soybean meal, soybean flour, soybean protein, seed proteins, animal milks, or other materials containing ammonium, amine, nitrate, amino acids, peptides, and proteins.

As used herein, the terms "non-nitrogen source," "non nitrogen source," and "non-N source" are used interchangeably to refer to a collection of other nutrients and trace elements that are necessary for the growth of the rhamnolipid producing bacteria and contain usable sources of phosphorus, sulfur, potassium, sodium, calcium, magnesium, chloride, iron, manganese, zinc, boron, cobalt, copper, and molybdenum. As used herein, a "usable source" or "available source" of a material refers to a source for that material that is in a form where it can be taken into and used by the rhamnolipid producing bacteria. The usable sources of these materials are not particularly limited and any source known in the art may be used provided, of course, that it is not toxic to the rhamnolipid producing bacteria and does not otherwise interfere with rhamnolipid production. In some embodiments, all of the various components comprising the non-nitrogen source are direct added to the fermentation medium. In some other embodiments, however, one or more of these components, particularly the trace elements that are added in minute quantities (i.e. phosphorus, sulfur, potassium, sodium, calcium, magnesium, manganese, zinc, boron, iron, cobalt, copper) and molybdenum, may be present as components in the water or other materials used in preparing the medium.

In some embodiments, the usable source of phosphorus may include, without limitation, $KH_2PO_4$, $K_2HPO_4$, $K_3PO_4$, $NaH_2PO_4$, $Na_2HPO_4$, $Na_3PO_4$, $(NH_4)H_2PO_4$, $(NH_4)_2HPO_4$, $(NH_4)_3PO_4$, soil extract, organic P-containing materials like soybean meal, corn meal, potato infusion, corn-steep liquor, yeast extract, peptone, tryptone, autolyzed yeast, or a combination thereof. In some embodiments, the source available sulfur may include, without limitation, $MgSO_4$, $(NH_4)_2SO_4$, $CaSO_4$, $MnSO_4$, $MnSO_4.H_2O$, $CuSO_4$, $CuSO_4.5H_2O$, $ZnSO_4$, $ZnSO_4.7H_2O$, soil extract, organic S-containing materials like soybean meal, corn meal, potato infusion, corn-steep liquor, yeast extract, peptone, tryptone, autolyzed yeast, or a combination thereof. In some embodiments, the source available potassium may include, without limitation, $KH_2PO_4$, $K_2HPO_4$, $K_3PO_4$, KCl, $KNO_3$, soil extract, organic K-containing materials like soybean meal, corn meal, potato infusion, corn-steep liquor, yeast extract, peptone, tryptone, autolyzed yeast, or a combination thereof. In some embodiments, the source available sodium may include, without limitation, NaCl, $NaNO_3$, $NaH_2PO_4$, $Na_2HPO_4$, $Na_3PO_4$, soil extract, organic K-containing materials like soybean meal, corn meal, potato infusion, corn-steep liquor, yeast extract, peptone, tryptone, autolyzed yeast, or a combination thereof. In some embodiments, the source available calcium may include, without limitation, $CaCl_2$, $CaCl_2.2H_2O$, $CaSO_4$, $CaCO_3$, soil extract, organic K-containing materials like soybean meal, corn meal, potato infusion, corn-steep liquor, yeast extract, peptone, tryptone, autolyzed yeast, or a combination thereof. In some embodiments, the source available magnesium may include, without limitation, $MgSO_4$, $MgCl_2$, soil extract, organic Mg-containing materials like soybean meal, corn meal, potato infusion, corn-steep liquor, yeast extract, peptone, tryptone, autolyzed yeast, or a combination thereof. In some embodiments, the source available chloride may include, without limitation, NaCl, $MnCl_2.4H_2O$, $MnCl_2.4H_2O$, $CaCl_2$, $CaCl_2.2H_2O$, $CoCl_2.CoCl_2.6H_2O$, $FeCl_3$, $FeCl_3.6H_2O$, soil extract, organic K-containing materials like soybean meal, corn meal, potato infusion, corn-steep liquor, yeast extract, peptone, tryptone, autolyzed yeast, or a combination thereof. In some embodiments, the source available iron may include, without limitation, $FeSO_4$, $FeSO_4.7H_2O$, $FeCl_3$, $FeCl_3.6H_2O$, soil extract, organic K-containing materials like soybean meal, corn meal, potato infusion, corn-steep liquor, yeast extract, peptone, tryptone, autolyzed yeast, or a combination thereof. In some embodiments, the source available manganese may include, without limitation, $MnCl_2$, $MnCl_2.4H_2O$, $MnSO_4$, $MnSO_4.2H_2O$, soil extract, organic Mn-containing materials like soybean meal, corn meal, potato infusion, corn-steep liquor, yeast extract, peptone, tryptone, autolyzed yeast, or a combination thereof. In some embodiments, the source available zinc may include, without limitation, $ZnSO_4$, $ZnSO_4.7H_2O$, $ZnCl_2$, soil extract, organic Zn-containing materials like soybean meal, corn meal, potato infusion, corn-steep liquor, yeast extract, peptone, tryptone, autolyzed yeast, or a combination thereof. In some embodiments, the source available boron may include, without limitation, $H_3BO_3$, $Na_2B_4O_7.10H_2O$, $Na_2B_8O_{13}.4H_2O$, soil extract, organic B-containing materials like soybean meal, corn meal, potato infusion, corn-steep liquor, autolyzed yeast, or a combination thereof. In some embodiments, the source available cobalt may include, without limitation, $CoCl_2$, $CoCl_2.6H_2O$, $Co(NO_3)_2$, $CoSO_4$, soil extract, organic Co-containing materials like soybean meal, corn meal, potato infusion, corn-steep liquor, autolyzed yeast, or a combination thereof. In some embodiments, the source available copper may include, without limitation, $CuSO_4$, $CuSO_4.5H_2O$, $CuCl_2$, soil extract, organic Cu-containing materials like soybean meal, corn meal, potato infusion, corn-steep liquor, autolyzed yeast, or a combination thereof. In some embodiments, the source available molybdenum may include, without limitation, $Na_2MoO_4$, soil extract, organic Co-containing materials like soybean meal, corn meal, potato infusion, corn-steep liquor, autolyzed yeast, or a combination thereof. In some embodiments, the non-N source will comprise $KH_2PO_4$, NaCl, $MgSO_4.7H_2O$, $FeSO_4.7H_2O$, $CaCl_2.2H_2O$, $MnCl_2.4H_2O$, $MnSO_4.H_2O$, $ZnSO_4.7H_2O$, $H_3BO_3$, $FeCl_3.6H_2O$, $CoCl_2.6H_2O$, $CuSO_4.5H_2O$ and $Na_2MoO_4$.

As will be apparent to those of ordinary skill in the art, the terms nitrogen source, carbon source, and non-nitrogen source refer to the intended and primary purpose of the particular nutrients being provided, and does not mean there cannot be some overlap between the nutrient sources. For example, a nitrogen source, such as a yeast extract, will also have some carbon that will be consumed in the same way as the added carbon source. Likewise, a carbon source, such as soybean hulls or soy molasses, will also have some nitrogen that will be consumed in the same way as the added nitrogen source.

As shown in FIG. 1, bacterial growth in batch fermentation systems may be broken down into four general phases. When the rhamnolipid producing bacteria is first added to a fermentation medium containing a carbon source, a nitrogen source, and the non-nitrogen source, the culture enters a first phase or "lag phase," which involves a period of no or slow growth where the cell culture acclimatizes to the new nutrient medium and conditions by synthesizing the required enzymes and growth factors. The second phase, referred to in FIG. 1 as the "exponential (growth) phase" and more generally herein as the "growth phase," is characterized by exponential growth in the number of rhamnolipid producing bacteria in the fermentation medium. As set forth above, the rhamnolipid producing bacteria use oxygen to live, and particularly to grow aerobically and the cell respiration rate is directly proportional to the cell growth rate. Accordingly, as the cell concentration increases due to growth, the increasingly higher cell respiration rates associated with the exponential cell growth in this phase necessitates higher aeration rates, which, combined with the foaming nature of rhamnolipid fermentation broth, tends to cause excessive foaming and other operational difficulties.

As some point, the rhamnolipid producing bacteria will consume all of a nutrient needed for cell growth and enter a third phase referred to in FIG. 1 as the "standing phase" and more generally herein as the "stationary phase" or "production phase" and is characterized by a relative stabilization in the concentration of rhamnolipid producing bacteria in the fermentation medium and production of rhamnolipids. The nutrient needed for cell growth that is exhausted first is generally referred to herein as the "limiting nutrient" and, in these systems, it will be either the N-source or the non-N source. In a final phase referred to in FIG. 1 as the "death (decline) phase," the concentration of rhamnolipid producing bacteria in the fermentation medium gradually declines as the rhamnolipid producing bacteria lose activity and/or viability.

As set forth above, a major problem with prior art rhamnolipid production methods has been their low productivity. Generally, rhamnolipid producing bacteria like *P. aeruginosa* produces rhamnolipids actively in the stationary phase of fermentation, when cell growth becomes limited by the N-source or the non N source, but not the C-source. To improve rhamnolipid productivity, therefore, the present invention maintains the culture in a prolonged stationary phase. This offers several advantages. First, it allows the rhamnolipids to accumulate to high concentrations for more cost-effective downstream collection. Second, longer stationary-phase production minimizes the reactor downtime and labor for cleaning and refilling. Third, it also reduces the substrate and time spent on growing the cells. Together, these advantages can enable the process to reach higher rhamnolipid concentration, productivity and yield.

For the above strategy to work, however, it is necessary to ensure the cells are actively metabolizing and producing rhamnolipids throughout the extended stationary phase. It has been found, however, that productivity of rhamnolipid producing bacteria, including several wild and mutant strains of *Pseudomonas* sp., gradually drop to zero during the late stationary phase in N-limited media. As set forth above, the methods of the present invention address this issue by using the non-nitrogen source as the limiting nutrient that initiates the standing phase and then supplementing fermentation broth with the nitrogen and carbon sources, the length of the standing phase, and with it the time during which rhamnolipid production occurs actively (without significant declination in the production rate) can be greatly extended, resulting in much higher productivity, conversion and product concentration and significantly lower overall production costs.

It is important to note here that while the nitrogen and carbon sources are supplemented in these embodiments, the carbon source is used also as the energy source to maintain cell viability, and not just for growth. Accordingly, the carbon source should not be used as the "limiting nutrient" to initiate the standing phase, since the rhamnolipid producing bacteria will quickly begin to die when the carbon source is exhausted. Similarly, while possible, using the addition rate of the carbon source as a way to control the cell growth rate is not preferred because cells can die very quickly if the carbon source addition is slightly inaccurate and there is even a brief period of carbon source exhaustion (by faster consumption rate than addition rate). Instead, the nitrogen-source addition rate is typically used to regulate the cell growth rate in the growth phase and the rhamnolipid productivity in the subsequent production phase, since the rhamnolipid producing bacteria will not die quickly if nitrogen source runs out.

In addition, as will be appreciated, a high cell concentration is generally desired during the fermentation process for achieving high volumetric productivity. However, because the cell respiration rate is directly proportional to both cell concentration and cell growth rate, building up a high concentration of fast-growing cells requires use of high aeration rates, which can lead to excessive foaming of rhamnolipid fermentation broths. As can be seen, a staged fermentation process according to one or more embodiments of the present invention achieves high cell concentrations in the growth phase by controlled feeding of N-source and then sustains high rhamnolipid productivity in the subsequent production phase with supplemental N-source addition, thereby improving the productivity and concentration of rhamnolipids for more favorable overall process economics.

In a first aspect, the present invention is directed to a method for improving production rates, conversions and concentrations of rhamnolipids during bacterial fermentation-based rhamnolipid production comprising: growing a rhamnolipid producing bacteria in a fermentation broth comprising at least one carbon source, at least one nitrogen source and a non-nitrogen source; and after the growth of the rhamnolipid producing bacteria is substantially complete, adding one or more additional quantities of a nitrogen source to maintain production of the rhamnolipids. In these embodiments, the rhamnolipid producing bacteria to be used is selected and then cultured using known methods. In various embodiments, the rhamnolipid producing bacteria may be any of the rhamnolipid producing bacteria identified above. In some embodiments, the rhamnolipid producing bacteria is a strain of *Pseudomonas aeruginosa*.

In these embodiments, a fermentation medium comprising at least one carbon source, at least one nitrogen source and the non-nitrogen source. As set forth above, suitable carbon sources include, but are not limited to vegetable oils, soybean oil, rapeseed oil, cocoa butter, olive oil, rice bran oil, palm oil, animal fat, glycerol, fatty acids, used cooking oil, waste oil, waste grease, glucose, fructose, sucrose, lactose, maltose, corn syrup, corn molasses, soy molasses, carbohydrates, and materials containing carbohydrates, glycerides, fatty acids, glycerol, amino acids, peptides and proteins. In one or more embodiments, the carbon source in the fermentation medium is a vegetable oil. In various embodiments, suitable nitrogen sources include, but are not limited to, $NH_4NO_3$, $NH_4Cl$, $NH_4OH$ (ammonia water), $(NH_4)_2SO_4$, $(NH_4)_3PO_4$, $(NH_4)_2HPO_4$, $(NH_4)H_2PO_4$, ammonium salts, $NaNO_3$, $KNO_3$, $Ca(NO_3)_2$, nitrate salts, urea, yeast extract, peptone, tryptone, protein hydrolysates containing amino acids and/or peptides, soybean meal, soybean flour, soybean protein, seed proteins, animal milks, materials containing ammonium, amine, nitrate, amino acids, peptides, and proteins. In these embodiments, the non-nitrogen source used to for the fermentation medium will be a mixture of compounds comprising available sources of phosphorus, sulfur, potassium, sodium, calcium, magnesium, chloride, iron, manganese, zinc, boron, cobalt, copper, and molybdenum, as described above. In some embodiments, the non-nitrogen source will comprise $KH_2PO_4$, NaCl, $MgSO_4.7H_2O$, $FeSO_4.7H_2O$, $CaCl_2.2H_2O$, $MnCl_2.4H_2O$, $MnSO_4.H_2O$, $ZnSO_4.7H_2O$, $H_3BO_3$, $FeCl_3.6H_2O$, $CoCl_2.6H_2O$, $CuSO_4.5H_2O$ and $Na_2MoO_4$. In various embodiments, the limiting nutrient in the fermentation medium will be either the N-source or the non-N source.

In one or more embodiments, the quantity and composition of the fermentation medium in the growth phase is calculated to a desired maximum cell concentration to reach at the end of the growth phase. As used herein, the term "maximum cell concentration" refers to the concentration of rhamnolipid producing bacteria available for rhamnolipid production at the beginning of the stationary or production phase. While some special strains may start to produce rhamnolipids before this point, the end of the growth phase is typically also the beginning of the active-rhamnolipid-production in the stationary phase. In various embodiments, the maximum cell concentration will be from about 5 g/L to about 50 g/L, depending upon desirable rhamnolipid productivity, available oxygen transfer effectiveness of the fermenter used, the foaming control device and design of the fermenter, and antifoam addition rate and amount. In some embodiments, the maximum cell concentration will be from about 10 g/L to about 50 g/L, in other embodiments, from about 15 g/L to about 50 g/L, in other embodiments, from about 20 g/L to about 50 g/L, in other embodiments, from about 25 g/L to about 50 g/L, in other embodiments, from about 30 g/L to about 50 g/L, in other embodiments, from about 35 g/L to about 50 g/L, in other embodiments, from about 5 g/L to about 45 g/L, in other embodiments, from about 5 g/L to about 40 g/L, in other embodiments, from about 5 g/L to about 35 g/L, in other embodiments, from about 5 g/L to about 30 g/L, in other embodiments, from about 5 g/L to about 25 g/L, and in other embodiments, from about 5 g/L to about 20 g/L. In some embodiments, the "maximum cell concentration" will be from about 29 g/L to about 30 g/L.

Once a desired maximum cell concentration is arrived at, the required amount of the carbon source, nitrogen source and non-nitrogen source strength (concentrations) required to grow the cells to the desired maximum cell concentration can be determined using the respective cell yields from carbon, nitrogen, and non-nitrogen sources, which can be measured empirically using standard microbiological testing procedures. As will be understood by those of skill in the art, the cell yield measurement can involve preparing media of varying concentrations of the tested substrate, e.g., carbon source, and same concentrations of other substrates and then growing the cells to corresponding maximum cell concentrations (with frequent sampling for measurements). In the media with low concentrations of the test substrate and the test substrate is the growth-limiting substrate, the maximum cell concentrations achieved increase with increasing test substrate concentrations; in the media with high concentrations of the test substrate and another substrate (other than the test substrate) becomes the growth-limiting substrate, the maximum cell concentrations achieved remain more or less constant, i.e., no longer increase with the test substrate concentrations. In this way, the cell yield from the test substrate can be determined as the slope of the increasing maximum cell concentrations with test substrate concentrations before the increasing trend plateaus.

In some embodiments, the fermentation medium will contain all of the carbon source and non-nitrogen source necessary to reach a desired maximum cell concentration at the end of the growth phase, but this need not be the case. In some embodiments, only a portion of the total quantity of one or both of the carbon source and non-nitrogen source necessary to reach a desired maximum cell concentration at the end of the growth phase will be present in the initial fermentation medium. In these embodiments, the remaining carbon source and non-nitrogen source may be added later during the growth phase, provided that they are added at a rate sufficient to maintain cell growth.

In some embodiments, the fermentation medium will have a pH of from about 5 to about 9, in other embodiments, from about 6 to about 8, and in other embodiments, from about 7 to about 7.5. In some embodiments, the fermentation medium will be adjusted to have a pH of about 7.0, by the addition of suitable acids or bases as is well known in the art. In some embodiments, the pH of the fermentation medium may be adjusted by the addition of 1 N $H_2SO_4$ or NaOH.

As will be appreciated by those of skill in the art, steps should be taken to ensure that the fermentation medium must be free from bacterial or other contamination prior to use. In various embodiments, the fermentation medium may be sterilized by direct or indirect steam sterilization, autoclave, filter sterilization, or combinations of the above methods. In some embodiments, the pH of the fermentation medium may be adjusted to 7.0 before autoclaving.

In various embodiments, the fermentation medium may also include various non-nutrient ingredients. In some embodiments, the fermentation medium will include one or more anti-foaming agents, including, but not limited to, vegetable oils, hydrocarbons, silicone oils, and various chemicals derived from silicones, alcohols, fatty acids and glycols. In some embodiments, the fermentation medium will include one or more osmoprotectant. In these embodiments, a solution of betaine, trehalose or other osmolytes will be filter-sterilized and added to the fermentation medium as an osmoprotectant. In some of these embodiments, the osmoprotectant is betaine and the final concentration of betaine solution in the fermentation medium will be from about 0.0001 mM to about 1.0 mM. In some of these embodiments, the final concentration of the betaine solution in the fermentation medium is about 0.5 mM. In addition, in very small scale fermentation runs, the fermentation medium may also include one or more pH buffer, but these are not typically used for industrial fermentation as they are more expensive than pH control by acid/base addition, as described herein.

The fermentation medium is either formed in or added to a suitable fermentation vessel. The fermentation vessel is not particularly limited but should include means for agitating and aerating the contents of the vessel, as is well known in the art. In some embodiments, the fermentation vessel is fitted with one or more turbines for stirring and agitating the contents of the vessel. In some of these embodiments, the fermentation vessel is fitted with one or more turbines, impellers, or similar structures capable of spinning at a rate necessary to aerate the contents of the vessel. The speed of the turbines or impellers used may changes significantly with fermenter scale and the size (diameter) of the impeller used. In some embodiments, the fermentation vessel is fitted with one or more turbines, impellers, or similar structures capable of spinning at a rate of from about 150 rpm to about 1500 rpm to stir the contents of the fermentation vessel. In some other embodiments, bubble-column and air-lift fermentors that use gas sparging to mix and aerate the contents may be used, although these systems can create potentially more serious foaming concerns. In smaller more bench scale fermentation embodiments, shake or magnetically stirred flasks may be used. In some embodiments, the fermentation vessel will have one or more inlets to allow the addition of air or oxygen into the vessel to aerate the contents of the vessel. One of ordinary skill in the art will be able to select a suitable fermentation vessel without undue experimentation.

Next a culture containing the rhamnolipid producing bacteria is added to the fermentation medium in the fermentation vessel to form the fermentation broth. As set forth above, after a brief lag phase, the fermentation broth enters an exponential growth phase. In various embodiments, the fermentation vessel is kept at a temperature of from about 15° C. to about 40° C. and stirred or agitated as set forth above during both the growth phase and stationary phases. As will be apparent to those of skill in the art, the growth rate in the growth phase and the rate of rhamnolipids production in the stationary phase are temperature dependent and the fermentation temperature can also be used, if necessary, to regulate the growth rate.

In some embodiments, the fermentation temperature in the growth phase and/or stationary phase is from about 15° C. to about 37° C., in other embodiments, from about 15° C.

to about 34° C., in other embodiments, from about 15° C. to about 30° C., in other embodiments, from about 15° C. to about 25° C., in other embodiments, from about 15° C. to about 20° C., in other embodiments, from about 20° C. to about 40° C., in other embodiments, from about 25° C. to about 40° C., in other embodiments, from about 30° C. to about 40° C., and in other embodiments, from about 35° C. to about 40° C. In some embodiments, the fermentation temperature in the growth phase and/or stationary phase is about 35° C.

As set forth above, the rhamnolipid producing bacteria require air and/or oxygen to live and grow aerobically in the method of the present invention throughout fermentation. Accordingly, in various embodiments, filter-sterilized air and/or oxygen is pumped into the fermentation vessel as necessary throughout the fermentation process. In these embodiments, the fermentation broth will be agitated or stirred to allow for even distribution of filter-sterilized air/oxygen and other materials throughout the fermentation broth, as is known in the art. In some of these embodiments, the fermentation vessel is fitted with one or more turbines, impellers, or similar structures capable of agitating or stirring fermentation broth at a rate necessary for aeration. The speed of fermentation broth is stirred for aeration depends on the fermenter scale and the size (diameter) of the impeller used.

In some embodiments, the fermentation broth is agitated or stirred at a rate of from about 150 rpm to about 1500 rpm throughout the fermentation process to ensure sufficient aeration of the fermentation broth. In some embodiments, the fermentation broth is agitated or stirred at a rate of from about 200 rpm to about 1500 rpm, in other embodiments, from about 400 rpm to about 1500 rpm, in other embodiments, from about 600 rpm to about 1500 rpm, in other embodiments, from about 800 rpm to about 1500 rpm, in other embodiments, from about 1000 rpm to about 1500 rpm, in other embodiments, from about 1200 rpm to about 1500 rpm, in other embodiments, from about 150 rpm to about 1400 rpm, in other embodiments, from about 150 rpm to about 1200 rpm, in other embodiments, from about 150 rpm to about 1000 rpm, in other embodiments, from about 150 rpm to about 800 rpm, and in other embodiments, from about 150 rpm to about 600 rpm during the fermentation. In some embodiments, the fermentation broth is agitated or stirred at a rate of from about 700 rpm to about 1100 rpm during the fermentation. In some embodiments, the fermentation broth is agitated or stirred during the growth phase at from about 800 rpm to about 1000 rpm using a turbine or impeller.

In various embodiments, the dissolved oxygen concentration ("DO") is kept at from about 0.08 mg/L to about 10 mg/L throughout fermentation. In some embodiments, the DO may be from about 0.1 mg/L to about 10 mg/L, in other embodiments, from about 1 mg/L to about 10 mg/L, in other embodiments, from about 2 mg/L to about 10 mg/L, in other embodiments, from about 4 mg/L to about 10 mg/L, in other embodiments, from about 6 mg/L to about 10 mg/L, in other embodiments, from about 8 mg/L to about 10 mg/L, in other embodiments, from about 0.08 mg/L to about 9 mg/L, in other embodiments, from about 0.08 mg/L to about 7 mg/L, in other embodiments, from about 0.08 mg/L to about 5 mg/L, in other embodiments, from about 0.08 mg/L to about 3 mg/L, and in other embodiments, from about 0.08 mg/L to about 1 mg/L.

In one or more embodiments, the fermentation broth will have a "DO" of from about 1% to about 100% air saturation during the growth phase, where the 100% value corresponds to the saturation DO of the fermentation medium when the medium is in equilibrium with air at 1 atm pressure. As used herein, the term "dissolved oxygen concentration" refers to the concentration of dissolved oxygen molecules in the broth, as measured by a dissolved oxygen electrode or other oxygen sensing devices. Depending on the fermentation temperature (and to a lesser extent, the composition of the fermentation medium), the 100% DO in the fermentation medium or broth corresponds to an actual oxygen concentration of from about 7 mg/L (at 40° C.) to about 10 mg/L (at 15° C.). In some embodiments, the fermentation broth will have a dissolved oxygen concentration of from about 5% to about 100%, in other embodiments, from about 10% to about 100%, in other embodiments, from about 20% to about 100%, in other embodiments, from about 30% to about 100%, in other embodiments, from about 40% to about 100%, in other embodiments, from about 50% to about 100%, in other embodiments, from about 75% to about 100%, in other embodiments, from about 1% to about 80%, in other embodiments, from about 1% to about 60%, in other embodiments, from about 1% to about 40%, and in other embodiments, from about 1% to about 20% during the growth phase.

In some embodiments, the fermentation broth is aerated with filter-sterilized air and the initial dissolved oxygen concentration (DO) of the broth naturally starts at about 100% with no or very low concentrations of cells to exert higher consumption (respiration) rates than the oxygen transfer rates from air bubbles to the aqueous fermentation medium. As cells grow and cell concentration increases, the increasing cell respiration rates cause DO to drop gradually. When DO drops to a predetermined DO control value, one or more control mechanisms will activate to increase the aeration rate, agitation rate, vessel pressure, inject pure oxygen into the broth, add/supplement more pure oxygen into the gas used for aeration, and/or combinations of the above, to maintain DO of the broth in certain control DO range. In one or more of these embodiments, the control DO range is from about 1% to about 30%, preferably from about 3% to about 20%, and most preferably from about 5% to about 15%.

Also, as will be appreciated by those of skill in the art the pH of the fermentation broth must be kept at a level that is not toxic to the rhamnolipid producing bacteria and does not interfere with rhamnolipid production. In one or more embodiments, the fermentation broth is kept at a pH of from about 4 to about 9 throughout fermentation. In some embodiments, the fermentation broth is kept at a pH of from about 4.8 to about 8.5, in other embodiments, from about 5.3 to about 8.5, in other embodiments, from about 5.6 to about 8.5, in other embodiments, from about 5.9 to about 8.5, in other embodiments, from about 6.0 to about 8.5, in other embodiments, from about 6.3 to about 8.5, in other embodiments, from about 7.0 to about 8.5, in other embodiments, from about 7.5 to about 8.5, in other embodiments, from about 4.0 to about 8.0, in other embodiments, from about 4.0 to about 7.5, in other embodiments, from about 4.0 to about 7.0, in other embodiments, from about 4.0 to about 6.5, and in other embodiments, from about 4.0 to about 6.0, throughout fermentation.

As will be apparent to those of skill in the art, the pH of the fermentation broth can naturally change as the cells grow and carry out their metabolic activities, including consumption of nutrient compounds that are acidic (such as the fatty acids in vegetable oil) or basic (such as ammonia from the N source) in nature and release of metabolic products such as organic acids. In some embodiments, the pH of the fermentation broth is continuously or periodically monitored using a standard pH meter or sensor, as known in the art. When the pH of the fermentation broth changes from the initial medium pH value to a predetermined control value, pH control is activated and a base and/or an acid are automatically added as necessary to maintain the pH within a control range. In one or more embodiments, the predetermined control value is a value in the range of from about 5 to about 8, preferably from about 5.5 to about 7.0, and most preferably from about 5.7 to about 6.0. Further, it has been found that cell growth and rhamnolipid production are better toward the upper end of the pH range (e.g., from about 6.0 to about 7.7), it has also been found that foaming increases rapidly with the higher pH. Accordingly, in embodiments where excessive foaming is likely to be an issue, a pH control value in the range of from about 5.7 to about 6.0 is preferred to minimize foaming. In some of these embodiments, the pH control value is in the range of from about 5.7 to about 5.8.

In some embodiments, the pH is allowed to drop naturally due to cell metabolism from an initial value of about 7.0 to the control set point of 5.70±0.05 and is then subsequently controlled by addition of 1 N $H_2SO_4$ or NaOH. In one or more embodiments, the control range itself will have a width of 0.10 to 1.0 surrounding the predetermined control value. For example, for a predetermined control value of 5.70, the actual pH is controlled in the range of 5.70±0.05 for the 0.10 width case or 5.7±0.5 for the 1.0 width case. The narrower range (e.g., ±0.05) is generally preferred, but can be difficult to control in large industrial fermenter and in these embodiments, a broader range (e.g., ±0.5) may be used.

As set forth above, the concentration of rhamnolipid producing bacteria continues to increase until either the N-source or non-N source nutrient is exhausted, since the carbon source is always present in excess. In this way, the concentration of rhamnolipid producing bacteria available for rhamnolipid production at the beginning of the stationary or production phase may be controlled by adjusting the cumulative concentration of the limiting nutrient provided.

As will be apparent, a high concentration of rhamnolipid producing bacteria available for rhamnolipid production is desired for achieving high volumetric productivity in the stationary phase. All other things being equal, the more rhamnolipid producing bacteria that are available for rhamnolipid production, the more rhamnolipids will be produced over a given time interval. However, the bacteria producing the rhamnolipids need oxygen to live, but particularly to grow aerobically. As the cell respiration rate is directly proportional to the cell growth rate, building up a high cell concentration necessitates high aeration rates, which, combined with the foaming nature of rhamnolipid fermentation broth, can cause excessive foaming and other operational difficulties. Moreover, because the rhamnolipid producing bacteria cells themselves tend to have more hydrophobic surfaces and contribute to the foaming speed and stability, as the concentration of rhamnolipid producing bacteria in the fermentation broth increases, the foaming nature of fermentation broth intensifies and it becomes increasingly difficult to control the foaming problem while aerating the fermentation broth to meet the cell respiration demand. Foaming can cause overflow of fermentation broth from the fermentor, creating not only loss of productivity but also potential biohazards. Even moderate foaming can cause wetting and/or clogging of filters, gas outlet(s), O-rings and other sealing parts that help prevent contamination of the fermentation operation, leading to fermentor pressure buildup, liquid and gas leakage through various fittings and connectors, and/or contamination of the fermentation.

In addition, very low concentrations of rhamnolipids, if any, are produced during the growth phase, and from a production standpoint, time spent growing the rhamnolipid producing bacteria, is time during which rhamnolipids are not being produced. For this and other reasons, attempts have been made to achieve high growth rates to shorten the length of the growth phase. As will be understood by those of skill in the art, the rate of growth of the rhamnolipid producing bacteria will depend upon a variety of factors, including, but not limited to, fermentation temperature, pH, dissolved oxygen concentration and the concentrations of available food source. As should also be apparent, increasing the growth rate results in a corresponding increase in cell respiration rate, thereby compounding the problem of excessive foaming.

In various embodiments, the methods of the present invention substantially prevent excessive foaming in the growth phase, while still achieving relatively high cell concentration levels, by slowing the grown rate of the rhamnolipid producing bacteria by reducing the ratio of the nitrogen source to the non-nitrogen source in the initial fermentation medium and then periodically supplementing the nitrogen source during the growth phase to slow and control the growth rate. As set forth, the amount of the Nitrogen source necessary to achieve a desired cell concentration can be empirically determined for a particular system, without undue experimentation. So, in various embodiments, this total required amount of the nitrogen source is basically divided into two portions, one portion that is added to the initial fermentation medium, and a second portion that is used to supplement the nitrogen source in the initial fermentation medium until the desired cell concentration is reached. At this point, cell growth will be limited by the limiting nutrient and the fermentation will enter the stationary phase.

As set forth above, there can be multiple compounds in the N source and there are always multiple compounds in the non-N source. For evaluation purposes the relative concentration ratios of different compounds in N source and non-N source were fixed and assigned a unit concentration strength (1×) assigned for each. For the non-N source, 1× strength corresponds to certain (different) concentrations of individual compounds (with their relative concentrations at the already fixed ratios as described below). The 1× unit concentration strength for the N source is defined in the same way. Concentrations of individual compounds corresponding to the 1× strength for various embodiments of the present invention are given in the Experimental section.

In some of these embodiments, the nitrogen source is the limiting nutrient during the growth phase and the nitrogen source in the initial fermentation medium is from about 10% to about 100% of the total amount of nitrogen source necessary to reach the desired cell concentration. In some embodiments, the nitrogen source is the limiting nutrient during the growth phase and the nitrogen source in the initial fermentation medium is from about 15% to about 100%, in other embodiments from about 25% to about 100%, in other embodiments from about 50% to about 100%, in other embodiments from about 75% to about 100%, in other embodiments from about 10% to about 80%, in other embodiments from about 10% to about 70%, in other embodiments from about 10% to about 60%, in other embodiments from about 10% to about 50%, and in other embodiments from about 10% to about 40% of the total amount of nitrogen source necessary to reach the desired cell concentration.

In some other embodiments, the non-nitrogen source is the limiting nutrient during the growth phase and the nitrogen source in the initial fermentation medium is from about 10% to about 100% of the total amount of nitrogen source necessary to reach the desired cell concentration. In some embodiments, the non-nitrogen source is the limiting nutrient during the growth phase and the nitrogen source in the initial fermentation medium is from about 15% to about 100%, in other embodiments from about 25% to about 100%, in other embodiments from about 50% to about 100%, in other embodiments from about 75% to about 100%, in other embodiments from about 10% to about 80%, in other embodiments from about 10% to about 70%, in other embodiments from about 10% to about 60%, in other embodiments from about 10% to about 50%, and in other embodiments from about 10% to about 40% of the total amount of nitrogen source necessary to reach the desired cell concentration.

In both of these embodiments, the growth phase may be divided into a first exponential growth stage wherein the rhamnolipid producing bacteria are allowed to grow rapidly for a period of time until the initial quantity of the nitrogen source in the fermentation medium has been substantially, if not fully, depleted and a second growth phase wherein additional quantities of the nitrogen source are added to the fermentation broth at a rate sufficient to promote continued cell growth, but not fast enough to cause excessive foaming. As will be apparent, because of the lower concentrations of rhamnolipid producing bacteria, the risk of excessive foaming is relatively low early in the "exponential growth" phase and increases later with the increasing cell concentration. Accordingly, in various embodiments of the present invention, only a portion of the total nitrogen source concentration necessary to reach the desired maximum cell concentration is initially added to the fermentation medium. Although not essential, all of the non-nitrogen source required for the growth phase is typically in the initial fermentation medium.

The amount of the nitrogen source in the initial fermentation medium should be enough to allow for rapid growth of the rhamnolipid producing bacteria at the beginning of the growth phase, but not enough to allow the cell concentration in this high growth rate period to get so high as to create excessive foaming before entry into the second growth phase. Similarly, the nitrogen source should be supplemented at a rate sufficient to promote continued cell growth, but not fast enough to cause excessive foaming. The portion of the total nitrogen source concentration in the initial the fermentation medium can, therefore, be adjusted according to the foaming tolerance of the fermentation vessel and related facilities and/or antifoaming devices. After that initial active growth period, the remaining nitrogen source for the growth phase is added either in multiple batches or, more preferably, by continuous pumping addition over the remaining growth phase. In these embodiments, the addition rate again can be adjusted according to the foaming tolerance and available antifoaming device.

In some of these embodiments, the nitrogen source periodically supplemented by adding batches of the nitrogen source equal to from about 0.001% (or less) to about 100% by weight of the amount of nitrogen source used to form the initial fermentation medium at intervals of from about 1 minute to about 180 minutes. As will be apparent, the amount of nitrogen source added with each batch will depend upon how often the batches of N source are added. It should be understood that the quantity of N source added in each batch will be adequate to sustain cell growth until the next batch is added. The amount added per batch will be very small if the batches are added very frequently.

In some embodiments, the batch size will be from about 0.1% to about 100%, in other embodiments, from about 10% to about 100%, in other embodiments, from about 20% to about 100%, in other embodiments, from about 30% to about 100%, in other embodiments, from about 40% to about 100%, in other embodiments, from about 50% to about 100%, in other embodiments, from about 0.001% to about 90%, in other embodiments, from about 0.001% to about 80%, in other embodiments, from about 0.001% to about 70%, in other embodiments, from about 0.001% to about 60% by weight of the amount of nitrogen source used to form the initial fermentation medium until the end of the stationary phase. In some embodiments, the N source is added at intervals of from about 10 minutes to about 180 minutes, in other embodiments, from about 30 minutes to about 180 minutes, in other embodiments, from about 45 minutes to about 180 minutes, in other embodiments, from about 60 minutes to about 180 minutes, in other embodiments, from about 90 minutes to about 180 minutes, in other embodiments, from about 120 minutes to about 180 minutes, in other embodiments, from about 1 minute to about 120 minutes, in other embodiments, from about 1 minute to about 90 minutes, in other embodiments, from about 1 minute to about 60 minutes, in other embodiments, from about 1 minute to about 30 minutes until the end of the stationary phase.

In some other embodiments, the nitrogen source is supplemented substantially continuously as is known in the art, rather than in batches. The term "substantially continuously," when is used in the context of adding a substance to the fermentation vessel or fermentation broth, to refers the addition of the substance at a generally constant and predetermined rate, as opposed to adding a substance in larger periodic batches. Consistent with this definition, the material may enter the fermentation vessel in a continuous stream or as droplets or pellets and the rate may change as conditions warrant. In these embodiments, the nitrogen source may be added substantially continuously using any means known in the art for doing so, including, but not limited to a pump, gravity feed, or a combination thereof. As will be apparent, this process permits foam production in the growth phase to be controlled by varying the rate at which the nitrogen source is added to the fermentation broth.

In various embodiments, the nitrogen source is supplemented substantially continuously at a rate of from about 0.04 grams nitrogen per liter per hour ("(g N)/L-h") to about 0.70 (g N)/L-h. In some embodiments, the nitrogen source is supplemented substantially continuously at a rate of from about 0.1 (g N)/L-h to about 0.70 (g N)/L-h, in other embodiments, from about 0.20 (g N)/L-h to about 0.70 (g N)/L-h, in other embodiments, from about 0.30 (g N)/L-h to about 0.70 (g N)/L-h, in other embodiments, from about 0.40 (g N)/L-h to about 0.70 (g N)/L-h, in other embodiments, from about 0.50 (g N)/L-h to about 0.70 (g N)/L-h, in other embodiments, from about 0.04 (g N)/L-h to about 0.60 (g N)/L-h, in other embodiments, from about 0.04 (g N)/L-h to about 0.50 (g N)/L-h, in other embodiments, from about 0.04 (g N)/L-h to about 0.40 (g N)/L-h, in other embodiments, from about 0.04 (g N)/L-h to about 0.30 (g N)/L-h, and in other embodiments, from about 0.04 (g N)/L-h to about 0.20 (g N)/L-h.

In embodiments where the nitrogen source is the limiting nutrient, the cell growth will stop when the nitrogen source is depleted. In these embodiments, supplementation with the nitrogen source is stopped when the rhamnolipid producing bacteria reaches a predetermined level and when the nitrogen source remaining in the fermentation broth is exhausted, growth will stop and the fermentation broth will enter the stationary phase where the rhamnolipids are produced. In embodiments where the non-nitrogen source is the limiting nutrient, supplementation with the nitrogen source continues until the non-nitrogen source is exhausted, at which point cell growth stops and the fermentation broth enters the stationary phase where the rhamnolipids are produced. In these embodiments, the total amount of the non-nitrogen source used in the growth phase should be calculated to generate the desired cell concentration. In some embodiments, all of the non-nitrogen source will be present in the initial fermentation medium, but this need not be the case and additional quantities of non-nitrogen source may be added later during the growth phase, provided that it remains the limiting nutrient.

As set forth above, in various embodiments the concentration of rhamnolipid producing bacteria available for rhamnolipid production at the beginning of the stationary or production phase ("maximum cell concentration") will be from about 5 g/L to about 50 g/L. In some embodiments, concentration of rhamnolipid producing bacteria available for rhamnolipid production at the beginning of the stationary or production phase is from about 29 g/L to about 30 g/L.

Once the growth phase is complete, the rhamnolipid producing bacteria shift to active production of rhamnolipids. As set forth above, however, it has been found that the productivity of rhamnolipid in long fermentation runs is often inconsistent and tends to decline during late stationary phase. It has been found, for example, that productivity of rhamnolipid producing bacteria, including several wild and mutant strains of *Pseudomonas* sp., gradually drops to zero during the late stationary phase in N-limited media. While not wishing to be bound by theory, it is believed that the decline in rhamnolipid productivity during long fermentation runs in known systems is likely associated with the cells' long-term maintenance metabolism in the nitrogen depleted conditions. This drop in productivity in prior art systems results in a shortening of the fermentation run that increases overall reactor downtime and labor for cleaning and refilling the fermentation equipment and a relatively low product concentration.

To address this issue and prolong productivity of the rhamnolipid producing bacteria, the fermentation broth in various embodiments of the present invention is supplemented with a nitrogen source during the stationary phase at a rate sufficient to maintain a substantially non-decreasing rate of rhamnolipids production. As set forth above, it has been found that by using the non-nitrogen source as the limiting nutrient that initiates the standing phase and then supplementing fermentation broth with the nitrogen and carbon sources, the length of the standing phase, and with it, the time during which rhamnolipid production occurs can be greatly extended. This results in much higher product concentrations than were possible with prior art methods of rhamnolipid production, significantly lowering overall production costs since the lower volume of fermentation broth lowers downstream collection costs because smaller equipment and facilities can be used, shortening processing times required to handle the smaller broth volume, and generating a smaller amount of spent or waste water, reducing costs for recovery or treatment before disposal.

As was the case during the growth phase, the fermentation broth may be supplemented with the nitrogen source continuously or in batches. Whether the supplementation is provided continuously or in batches, however, the amount of supplementation provided should be enough to maintain a substantially non-decreasing rate of rhamnolipids production, but not so much as to permit the rhamnolipid producing bacteria to produce "non-rhamnolipid" byproducts, such as polysaccharides like alginate, pigments like pyocyanin, pyoverdine, aeruginosin and pyomelanin, and extracellular enzymes like elastase, lipase and protease. Overproduction of any of these byproducts diverts the available carbon source from rhamnolipid production, causing lower rhamnolipid conversion and productivity, and complicates the downstream rhamnolipid separation and purification. Polysaccharide production can substantially increase broth viscosity, causing poor mixing and seriously compromised oxygen supply effectiveness to cells. Some metabolites can accumulate to inhibitory levels to the rhamnolipid producing bacteria and to the users and/or environment for the intended applications of rhamnolipid products, requiring more extensive purification to reduce or remove these metabolites.

While not required, it is strongly preferred that the limiting nutrient during the stationary phase is the non N source. As will be appreciated, if the nitrogen source is the limiting nutrient, addition of additional nitrogen source will cause the fermentation broth to, at least temporarily, re-enter a growth phase, during which time few, if any, rhamnolipids are produced. When the non N Source is used as the limiting nutrient, however, the fermentation broth will remain in the stationary phase and nitrogen source supplementation will not interrupt the rhamnolipid production.

Unless otherwise indicated, fermentation conditions (temperature, pH, stirring speed, DO, air saturation, aeration etc.) during the stationary phase are within the ranges set forth above to the growth phase.

As set forth above, by supplementing the fermentation broth with a nitrogen source (as well as the carbon source) during the stationary phase, various embodiments of the present invention permit long fermentation runs, since problems with declining rhamnolipid productivity, likely due to the rhamnolipid producing bacteria cells' long-term maintenance metabolism in the nitrogen depleted conditions, are avoided. In various embodiments, the nitrogen source may be added in batches or in a substantially continuous manner. In some embodiments, the nitrogen source is added to the fermentation broth in batches of from about 5% to about 75% by weight of the amount of the nitrogen source used in the growth phase, every about 12 hours to about 48 hours after the fermentation broth enters the stationary phase. In some embodiments, each batch added to the fermentation broth will contain from about 5% to about 75%, in other embodiments, from about 10% to about 75%, in other embodiments, from about 20% to about 75%, in other embodiments, from about 40% to about 75%, in other embodiments, from about 60% to about 75%, in other embodiments, from about 5% to about 65%, in other embodiments, from about 5% to about 55%, in other embodiments, from about 5% to about 45%, in other embodiments, from about 5% to about 35%, and in other embodiments, from about 5% to about 25% by weight of the amount of the nitrogen source used in the growth phase. In some embodiments, a batch is added every about 15 hours to about 48 hours, in other embodiments, from about 24 hours to about 48 hours, in other embodiments, from about 30 hours to about 48 hours, in other embodiments, from about 36 hours to about 48 hours, in other embodiments, from about 42 hours to about 48 hours, in other embodiments, from about 12 hours to about 40 hours, in other embodiments, from about 12 hours to about 30 hours, and in other embodiments, from about 12 hours to about 20 hours, after the fermentation broth enters the stationary phase.

In one or more embodiments, the nitrogen source is added to the fermentation broth substantially continuously so as to provide from about 2.5% to about 150% by weight of the amount of the nitrogen source used to form the fermentation medium every about 24 hours after the fermentation broth enters the stationary phase. In some of these embodiments, nitrogen source is added to the fermentation broth at a rate of from about 5.0% to about 150%, in other embodiments, from about 15.0% to about 150%, in other embodiments, from about 25% to about 150%, in other embodiments, from about 50% to about 150%, in other embodiments, from about 75% to about 150%, in other embodiments, from about 2.5% to about 125%, in other embodiments, from about 2.5% to about 100%, in other embodiments, from about 2.5% to about 75%, in other embodiments, from about 2.5% to about 50%, by weight of the amount of the nitrogen source used to form the fermentation medium every about 24 hours after the fermentation broth enters the stationary phase.

As set forth above, by supplementing the fermentation broth with a nitrogen source (as well as the carbon source) during the stationary phase, it becomes possible to have long fermentation runs, since problems with declining rhamnolipid productivity likely due to the rhamnolipid producing bacteria cells' long-term maintenance metabolism in the nitrogen depleted conditions are avoided. In some embodiments, a substantially non-decreasing rate of rhamnolipids production can be maintained for from 24 hours to about 600 hours. In some of these embodiments, a substantially non-decreasing rate of rhamnolipids production can be maintained for from 30 hours to about 600 hours, in other embodiments, from about 50 hours to about 600 hours, in other embodiments, from about 100 hours to about 600 hours, in other embodiments, from about 200 hours to about 600 hours, in other embodiments, from about 300 hours to about 600 hours, in other embodiments, from about 400 hours to about 600 hours, in other embodiments, from about 24 hours to about 500 hours, in other embodiments, from about 24 hours to about 400 hours, in other embodiments, from about 24 hours to about 300 hours, and in other embodiments, from about 24 hours to about 200 hours.

There is, in theory, essentially no limit to the amount of rhamnolipids that can be produced in this manner provided. However, as the rhamnolipid concentration increases, the fermentation broth becomes increasingly viscous and stirring and aeration of the fermentation broth becomes impractical, if not impossible, and some or all of the rhamnolipids in the fermentation broth must be harvested. In some embodiments, the rhamnolipid concentration in the fermentation broth will reach from about 50 g/L to about 200 g/L, before some or all of the rhamnolipids in the fermentation broth are harvested. In some of these embodiments, the rhamnolipid concentration in the fermentation broth will reach from about 60 g/L to about 200 g/L, in other embodiments, from about 70 g/L to about 200 g/L, in other embodiments, from about 80 g/L to about 200 g/L, in other embodiments, from about 90 g/L to about 200 g/L, in other embodiments, from about 100 g/L to about 200 g/L, in other embodiments, from about 150 g/L to about 200 g/L, in other embodiments, from about 50 g/L to about 150 g/L, in other embodiments, from about 50 g/L to about 100 g/L, in other embodiments, from about 50 g/L to about 90 g/L, and in other embodiments, from about 50 g/L to about 80 g/L before some or all of the rhamnolipids in the fermentation broth are harvested. In various embodiments, the rhamnolipid concentration in the fermentation broth will be at least 75 g/L before some or all of the rhamnolipids in the fermentation broth are harvested. In some embodiments, the rhamnolipid concentration in the fermentation broth will reach from about 90 g/L to about 100 g/L, before some or all of the rhamnolipids in the fermentation broth are harvested.

In one or more embodiments, the conversion of the carbon source to rhamnolipids during the stationary phase is from about 50% to about 90% by weight. In some embodiments, the conversion of the carbon source to rhamnolipids during the stationary phase is from about 55% to about 90%, in other embodiments, from about 65% to about 90%, in other embodiments, from about 70% to about 90%, in other embodiments, from about 80% to about 90%, in other embodiments, from about 85% to about 90%, in other embodiments, from about 50% to about 85%, in other embodiments, from about 50% to about 80%, in other embodiments, from about 50% to about 75%, in other embodiments, from about 50% to about 70%, and in other embodiments, from about 50% to about 60%, by weight.

The rhamnolipids may be harvested (i.e. recovered) from the fermentation broth using any method known in the art for that purpose. In some embodiments, the broth is added with a 2-3 fold volume of ethanol to cause biopolymers to come out of solution. In these embodiments, the broth is then centrifuged to remove the cells and the precipitated biopolymers. The ethanol is then vaporized for removal and recovery from the supernatant. The supernatant is next acidified to a pH below 3, typically at a pH of about 2.5, to convert the soluble anionic rhamnolipids to insoluble protonated rhamnolipids. In some of these embodiments, the acidified supernatant is centrifuged again to collect the precipitated rhamnolipids. In some other embodiments, the acidified supernatant may be contacted with solvent like ethyl acetate to extract rhamnolipids into the solvent phase and collected after solvent vaporization. In embodiments where further purification of the rhamnolipids is desired or necessary for their intended uses, it can be done by any method known in the art for that purpose, including, without limitation, chromatographic methods or other more selective separation methods such as sequential extraction, adsorption, and/or crystallization.

In a second aspect, the present invention relates to processes for producing a fermentation broth having a concentration of rhamnolipids of 75 g/L or more comprising: preparing a bacterial seed culture comprising Pseudomonas aeruginosa bacteria; preparing a fermentation medium in a suitable fermentation vessel equipped to agitate and aerate a fermentation broth, the fermentation medium comprising a carbon source selected from the group consisting of vegetable oil, soybean oil, rapeseed oil, cocoa butter, olive oil, rice bran oil, palm oil, animal fat, glycerol, fatty acids, used cooking oil, waste oil, waste grease, glucose, fructose, sucrose, lactose, maltose, corn syrup, corn molasses, soy molasses, carbohydrates, materials containing carbohydrates, glycerides, fatty acids, glycerol, and combinations thereof, a nitrogen source selected from the group consisting of $NH_4NO_3$, $NH_4Cl$, $NH_4OH$ (ammonia water), $(NH_4)_2SO_4$, $(NH_4)_3PO_4$, $(NH_4)_2HPO_4$, $(NH_4)H_2PO_4$, ammonium salts, $NaNO_3$, $KNO_3$, $Ca(NO_3)_2$, nitrate salts, urea, yeast extract, peptone, tryptone, protein hydrolysates containing amino acids and/or peptides, soybean meal, soybean flour, soybean protein, seed proteins, animal milks, materials containing ammonium, amine, nitrate, amino acid, peptides proteins, and combinations thereof, and a non-nitrogen source containing phosphorus, sulfur, potassium, sodium, calcium, magnesium, chloride, iron, manganese, zinc, boron, cobalt, copper, and molybdenum, wherein the non-nitrogen source is the limiting nutrient; adding the bacterial seed culture to the fermentation medium to form a fermentation broth; agitating and aerating the fermentation broth at a temperature of from about 15° C. to about 40° C. to grow the *Pseudomonas aeruginosa* bacteria in the fermentation broth; periodically adding an additional quantity of the nitrogen source in an amount of from about 0% to about 100% by weight of the amount of the nitrogen source used to form the fermentation medium every about 1 second to about 180 minutes to allow the *Pseudomonas aeruginosa* bacteria to grow until the non-nitrogen source is substantially consumed, wherein the growth of the *Pseudomonas aeruginosa* bacteria substantially stops and the fermentation broth enters a phase wherein rhamnolipids are produced; supplementing the nitrogen source at a rate of from about 5% to about 75% by weight of the amount of the nitrogen source used to grow the *Pseudomonas aeruginosa* bacteria every about 12 to about 48 hours to maintain substantially non-decreasing rate of rhamnolipids production for from 24 hours to about 600 hours until the rhamnolipid concentration in the fermentation broth reaches a concentration of at least about 75 g/L; and removing some or all of the fermentation broth and harvesting the rhamnolipids contained therein.

In a third aspect, the present invention is directed to a continuous process for producing rhamnolipids by bacterial fermentation using one or more of the methods set forth above. In these embodiments, the rhamnolipids are produced by fermentation using rhamnolipid producing bacteria as set forth above, until a desired rhamnolipid concentration is reached. In some of these embodiments, the rhamnolipids are produced until the rhamnolipid concentration reaches a desired level. In some embodiments, the rhamnolipids are produced until the rhamnolipid concentration reaches from about 50 g/L to about 200 g/L, as set forth above. At this point, a quantity of the fermentation broth is removed for rhamnolipid harvesting and replaced with a quantity of fresh fermentation medium, as described above.

In some embodiments, from about 20% to about 95% of the volume of the fermentation broth is removed and the rhamnolipids contained therein are harvested. At the low end, if 20% of the volume of the fermentation broth is removed, the cell concentration is only 20% diluted by the fresh medium for growth phase, e.g., drops from 30 g/L to 24 g/L (due to dilution) and will quickly regrow (maybe 1 h) back to 30 g/L and starts to produce rhamnolipid again. So, production interruption by the intermittent growth phase is minimal. However, this also means rhamnolipids and other byproducts are only 20% diluted by each cycle and the fermentation broth remains relatively viscous all the time (fluctuating between, say, 80 g/L (after dilution) and 100 g/L) and, few (unknown) inhibitory compounds (if any) are removed by each cycle to slow down their accumulation in the operation. On the other hand, taking 95% of the volume of the fermentation broth or more has the opposite effect. It lengthens the repeated growth phase. Further, taking 95% of the volume of the fermentation broth in each cycle results in what is essentially a repeat fresh batch fermentation.

In addition, determining how much of the fermentation broth to harvest in each cycle will also depends on the coupling with the downstream processing. If downstream processing is quick and almost continuous in nature, harvesting small amount frequently couples well without a need of additional broth storage vessel with refrigeration to prevent further biological reactions and minimize contamination during storage. If downstream processing is done in large batches, however, then harvesting a larger volume in less frequent batches couples better.

In some embodiments, from about 30% to about 95%, in other embodiments, from about 50% to about 95%, in other embodiments, from about 70% to about 95%, in other embodiments, from about 80% to about 95%, in other embodiments, from about 90% to about 95%, in other embodiments, from about 20% to about 85%, in other embodiments, from about 20% to about 75%, in other embodiments, from about 20% to about 60%, in other embodiments, from about 20% to about 50%, and in other embodiments, from about 20% to about 30% of the volume of the fermentation broth is removed and the rhamnolipids contained therein are harvested.

In various embodiments, the volume of fresh fermentation medium added to the fermentation broth will be approximately the same as the volume of the fermentation broth removed for rhamnolipid harvesting, but this need not be the case and depending upon the capacity of the fermentation vessel, any amount of fresh fermentation medium may be added. If, for example, many samples were taken for testing during the process or the air/oxygen used for aeration is not humidified and thus strips water from the fermenter by vaporization, the volume of fluid in the fermentation broth may be significantly reduced and it may be desirable to add more fresh medium than was removed for harvesting to restore the original volume. On the other hand, if substantial volumes of acid/base were added to the fermentation for pH control, it may be desirable to add less fresh medium than was removed for harvesting, so that the broth volume does not exceed the optimal operation level (or overflow or allowing foam layer to get too close to the top plate of fermenter).

In these embodiments, the fermentation is then allowed to continue as described above until the rhamnolipid concentration again reaches a desired level and the process of removing a quantity of the fermentation broth for rhamnolipid harvesting and replacing it with a quantity of fresh fermentation medium, as described above, is repeated. In various embodiments, this process may be repeated any number of times to create what amounts to a continuous process for rhamnolipid production. In some embodiments, these steps are repeated from about 1 to about 100 times. When the fermentation run is to be ended, all of the fermentation broth is collected and the rhamnolipids contained therein harvested.

In some embodiments, the process for producing rhamnolipids by bacterial fermentation according to the present invention comprises: preparing a bacterial seed culture comprising at least one rhamnolipid producing bacteria; preparing a fermentation medium in a suitable fermentation vessel, the fermentation medium comprising a carbon source, a nitrogen source, and a non-nitrogen source containing phosphorus, sulfur, potassium, sodium, calcium, magnesium, chloride, iron, manganese, zinc, boron, cobalt, copper, and molybdenum; adding the bacterial seed culture and at least one of air and oxygen to the fermentation medium to form a fermentation broth; growing the rhamnolipid producing bacteria in the fermentation broth; periodically adding additional quantities of the nitrogen source to allow the rhamnolipid producing bacteria to grow until the non-nitrogen source is substantially consumed, wherein rhamnolipid producing bacteria growth substantially stops and rhamnolipids are produced; periodically supplementing the nitrogen source to prolong rhamnolipid production until the rhamnolipid concentration in the fermentation broth reaches a concentration of from about 50 g/L to about 200 g/L;

removing some or all of the fermentation broth and harvesting the rhamnolipids contained therein.

In some of these embodiments, from about 20% to about 95% of the volume of the fermentation broth is removed for rhamnolipid harvesting and replaced with a comparable volume of fresh fermentation medium. In these embodiments, the fermentation is then continued as before by periodically supplementing the nitrogen source to prolong rhamnolipid production until the rhamnolipid concentration in the fermentation broth reaches a concentration of from about 50 g/L to about 200 g/L, at which time, from about 20% to about 95% of the volume of the fermentation broth is removed for rhamnolipid harvesting and replaced with a comparable volume of fresh fermentation medium, as described above. In these embodiments, this process may be repeated from about 1 to about 100 times, until the fermentation run is termination and all of the fermentation broth is collected and the rhamnolipids harvested.

All publications, patent applications, patents, and other references mentioned herein are expressly incorporated by reference in their entirety, which means that they should be read and considered by the reader as part of this text. That the document, reference, patent application, or patent cited in this text is not repeated in this text is merely for reasons of conciseness. In the case of conflict, the present disclosure, including definitions, will control. All technical and scientific terms used herein have the same meaning.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is average molecular weight, temperature is in degrees Centigrade, and pressure is at or near atmospheric.

Example 1

Evaluation of Rhamnolipids Production Under Varied Production Conditions

In order to better illustrate and further reduce embodiments of the present invention to practice, *P. aeruginosa* was used to produce rhamnolipids under varied production conditions. In these experiments, rhamnolipids were first made using the commonly employed nitrogen-limited stationary phase, but with different N-source supplementation rates and their long-term rhamnolipid production were evaluated and their specific productivity ($q_p$) calculated and evaluated. In this first set of experiments, it was found that the intermittent cell growth due to N-source addition led to lower $q_p$, particularly apparent at the highest addition rate. In a second set of experiments, four fermentations were made using a non-N-limited stationary phase without and with N-source supplementation and it was found that $q_p$ could be much higher. In a third set of experiments, three fermentations were designed to build a maximum cell concentration to 29-30 g/L in two growth phases where growth rate in the second phase was regulated by N-addition to avoid excessive foaming. These cultures then entered non-N-limited stationary phase and were N-supplemented at different rates. At the optimal rate of 15% growth-N per 24 h to maintain cell activity, a highest rhamnolipid concentration of 105 g/L was obtained after 144 h with an overall (0-144 h) productivity of 731 mg/L·h. It was found that beyond this rhamnolipid concentration, the broth turned too viscous to allow suitable oxygen transfer. In another set of experiments, repeated cycles of growth-production-partial harvesting and medium replacement were demonstrated to produce high rhamnolipid concentrations at high productivity.

1. Materials and Methods 1.1 Bacterial Culture Preparation

The bacterium *Pseudomonas aeruginosa* used in this study is a rhamnolipid-producing strain screened from soil samples. (See, Pinzon N M, Ju L-K. "Improved detection of rhamnolipid production using agar plates containing methylene blue and cetyl trimethylammonium bromide." *Biotechnol Lett.* 2009. doi:10.1007/s10529-009-0049-7, the disclosure of which is incorporated herein by reference in its entirety). The seed culture of *Pseudomonas aeruginosa* used in these experiments was activated in 5 mL of sterile 30 g/L Tryptic Soy Broth (TSB) for 12 h at 32° C. under 250 rpm shaking. It was then added to 50 mL of 30 g/L TSB, grown under similar conditions for 20 h, and used as the inoculum for the studies carried out in the fermentors.

1.2 Fermenter Studies

The experiments were carried out in 2-L fermentors (BIOFLO 110, New Brunswick Scientific) containing 1 L fresh medium which was agitated at 800 rpm with two 6-blade turbines. The temperature was maintained at 32° C. Dissolved oxygen concentration (DO) was set at 10% (air saturation) with automatic adjustment of the flow rate of pure oxygen; nonetheless, DO could fluctuate up to a range of 5%-50% during periods of faster metabolic changes. The pH was allowed to drop naturally due to cell metabolism from the initial value of 7.0 to the control set point of 5.70±0.05 and was subsequently controlled by addition of 1 N $H_2SO_4$ or NaOH.

The medium used contained 100 g/L vegetable oil as the carbon source; 5.76 g/L $NH_4Cl$, 5 g/L yeast extract, and 5 g/L peptone as the nitrogen source; and 6 g/L $KH_2PO_4$, 1.5 g/L NaCl, 0.9 g/L $MgSO_4 \cdot 7H_2O$, 0.1 g/L $FeSO_4 \cdot 7H_2O$, 0.03 g/L $CaCl_2 \cdot 2H_2O$, 0.03 g/L $MnCl_2 \cdot 4H_2O$, and 2 mL of a trace element solution comprising 0.75 g/L $MnSO_4 \cdot H_2O$, 0.75 g/L $ZnSO_4 \cdot 7H_2O$, 0.15 g/L $H_3BO_3$, 0.08 g/L $FeCl_3 \cdot 6H_2O$, 0.08 g/L $CoCl_2 \cdot 6H_2O$, 0.075 g/L $CuSO_4 \cdot 5H_2O$ and 0.05 g/L $Na_2MoO_4$ as the non-nitrogen source. The concentrations of the above-mentioned components (excluding the vegetable oil) were considered as 1×. The medium pH was adjusted to 7.0 before autoclaving. Additionally, a 10 g/L betaine solution was filter-sterilized and added as an osmoprotectant, at a final concentration of 0.5 mM in the medium.

Soybean oil was used as the carbon source in all the fermentation runs at a concentration of 100 g/L in the initial media. It was also added periodically to provide 20 g/L additional soybean oil per day to the cells. The concentrations of the above-mentioned components (excluding the vegetable oil) were considered as 1×. Nitrogen was the limiting component in the initial medium for fermentation runs F1-F3. The fermentation runs F4-F10 were conducted using different proportions of nitrogen and non-nitrogen (also non-C) components in the initial medium, as shown in Table 1. Rationales of the experimental design for making fermentations under these different schemes are described in the later Section 2.5 Experimental Design.

TABLE 1

The proportion of nitrogen and non-nitrogen source components in the initial medium for different fermentation runs

| Fermentation run | N-source | Non-N source* |
|---|---|---|
| F1 | 1X | 1X |
| F2 | 0.5X | 0.5X |
| F3 | 0.5X | 0.5X |
| F4 | 1X | 0.5X |
| F5 | 1X | 0.5X |
| F6 | 1.5X | 1X |
| F7 | 1.5X | 1X |
| F8 | 1.5X | 1.25X |
| F9 | 1.5X | 1.25X |
| F10 | 1.5X | 1.25X |

*The non-N source medium components given here did not include the C-source vegetable oil which was fed separately as described in the text.

1.3 Analytical Techniques

Intracellular protein concentrations, measured by the standard Bradford method, were converted to cell dry-weight concentrations using a pre-established calibration. Briefly, the fermentation broth sample was centrifuged, the supernatant carefully decanted, the settled cell pellet resuspended in distilled water and centrifuged again. The water was carefully removed and the washed cells were lysed with a 0.2 N NaOH solution under heating at 95° C. for 20 min. The released intracellular protein was then quantified using a diagnostic kit (Bio-Rad Protein Assay kit II, Bio-Rad Laboratories) with measurement of absorbance at 595 nm using a Shimadzu UV/Vis spectrophotometer (Model 1601). The protein concentration was then converted to the cell dry-weight concentration according to a calibration curve developed for this purpose. For the determination of dry cell weight, the washed cells collected by centrifugation were dried to constant weight at 90° C. for 24 h. Glycerol analysis was done by high performance liquid chromatography (HPLC, Model LC1100, Agilent Technologies, Santa Clara, Calif.) with the eluate being monitored using a refractive index detector (RID-10A). The ammonium concentrations in samples taken along fermentation were measured using an ammonia electrode (High Performance Ammonia Ion Selective Electrode, Thermo Scientific, Beverly, Mass.). Rhamnolipid analysis was done by the standard anthrone method and by using the HPLC with an evaporative light scattering detector (ELSD, Model 300, SofTa Corporation, Thornton, Colo.). For the anthrone analysis, the measured rhamnose concentrations were multiplied by 2.38 to estimate the rhamnolipid concentrations. This value of 2.38 was based on the composition of the rhamnolipid mixture produced, determined by High-Performance Liquid Chromatography interfaced to Evaporative Light-Scattering Detectors (HPLC-ELSD). The extracellular components of the fermentation broth were analyzed by gel permeation chromatography (GPC) using a Pb aquagel-OH 5 μm column (Agilent Technologies, Lanarkshire, UK) with a refractive index detector (RID-10A). The standard calibration curve obtained by using polyethylene glycol/oxide standards (EasiVial PS-H, Agilent Technologies, Santa Clara, Calif.) was used to assess the molecular weights of the extracellular components in the broth.

Fatty acid (FA) analysis was done after converting FAs present in the fermentation broth to fatty acid methyl esters (FAMEs) as given in the standard method (TP-5100-60958) by National Renewable Energy Laboratory (NREL) (2013). (See, Van Wychen S, Laurens L (2013) "Determination of total lipids as fatty acid methyl esters (FAME) by in situ transesterification: laboratory analytical procedure (LAP)." *National Renewable Energy Laboratory* (NREL), Golden, Colo., the disclosure of which is incorporated herein by reference in its entirety.) The FAME analysis was done using gas chromatography (GC-17A, Shimadzu Corp., Columbia, USA) with flame ionization detector (FID). Famewax column (Restek Corporation, Bellefont, Pa., USA) was utilized and a column temperature of 130° C. and detector temperature of 230° C. were used for this analysis. FAME mix, C4-C24 (Sigma-Aldrich, St. Louis, Mo., USA) was used as a calibration standard for GC-FID.

1.4 Calculations

There was a continuous change in the volume of broth during the fed-batch fermentation due to addition of acid, base, antifoam agents, and nutrients as well as sample removal from the fermentor. The volume changes were considered and adjusted while computing different concentration profiles, to determine the intrinsic culture properties. The effective broth volume at every sampling time was recorded; and average specific cell growth rate ($\mu$) and specific product formation rate ($q_p$), and the time-averaged cell biomass ($X_{t,avg}$) were calculated for every interval between two consecutive sampling times using the following equations, where subscripts 0 and 1 denote the respective samples at t and (t+$\Delta$t):

$$\mu = \frac{\ln\left(\frac{X_1}{X_0}\right)}{\Delta t} \quad \text{(Eq. 1)}$$

$$X_{t,avg} = \frac{\int_0^{\Delta t} X_0 e^{\mu t} dt}{\Delta t} = \frac{X_0}{\mu \Delta t}(e^{\mu \Delta t} - 1) \quad \text{(Eq. 2)}$$

$$q_p = \frac{(P_1 - P_0)}{X_{t,avg} \Delta t} = \frac{\mu(P_1 - P_0)}{X_0[e^{\mu(\Delta t)} - 1]} = \frac{\mu(P_1 - P_0)}{(X_1 - X_0)} \quad \text{(Eq. 3)}$$

In the above equations, X and P refer to the weights of cell biomass and rhamnolipid product (X=x V and P=p V, where x, p and V are respectively the cell and rhamnolipid concentrations and broth volume determined at each sampling time). During the interval between two sampling points, X changed only by cell growth and P by production while x and p would also be affected by the continuously changing broth volume. The time averaged cell concentration in a specific interval was obtained by considering the exponential cell growth during the interval, with the average specific growth rate $\mu$. All the concentration profiles described in this experiment were adjusted for the volume change during the fermentation runs.

1.5 Experimental Design

As set forth above, in the first set of experiments, three fermentation runs (F1-F3 in Table 1) were carried out in a fed-batch mode at different addition rates of an N source, $NH_4NO_3$. The N-source was the limiting nutrient in the initial media for inducing the stationary phase. The average cell concentrations and volumetric and specific productivity of rhamnolipid obtained in these runs were determined. Specific oxygen uptake rate (SOUR) by the cells was calculated from the dissolved oxygen profile within every on-off cycle of oxygen addition used for DO control. This SOUR was used as an index to track the change of metabolic rate during the different stages and time of fermentation.

In the next set of experiments, fermentation runs (F4-F7 in Table 1) were conducted in batch and fed-batch modes at two different proportions of nitrogen to non-nitrogen components in the initial medium (1X N:0.5 X non-N for F4 and F5, and 1.5X N:1X non-N for F6 and F7). These were done to determine the ratio which would enable stationary phase to be induced by non-nitrogen component in the initial medium. And they enabled evaluation of the effect of N-source supplementation on volumetric and specific productivities of rhamnolipid, with and without causing further cell growth.

Based on the data obtained from the above four fermentation runs (F4-F7), a two-stage fermentation design was further developed by using controlled feeding of N-source to achieve sustained high cell and rhamnolipid concentration profiles while avoiding the problem of excessive foaming associated with aeration to meet the high respiration demands from high concentrations of fast-growing cells. This design was evaluated in three fermentation runs (F8-F10) with different N supplementation rates during the stationary phase (highest in F9 and lowest in F10, details given in the Results and Discussion (Section 2, below) for clearer correlation). (See, Table 1) In addition, the good performance established in F8 was verified for reproducibility and evaluated in F10 with two cycles of fed-batch operation. In F10, after the rhamnolipid production almost reached its maximum achievable in the first fed-batch cycle, 85% broth with product was harvested and the controlled N-source feeding repeated for the second cycle of regulated cell growth and subsequent rhamnolipid production. This fermentation F10 was done to investigate the feasibility of using this design/control scheme for repeated-cycle fed-batch process to achieve the highest rhamnolipid productivity in a very long fermentation run.

1.6 Composition of Rhamnolipids Congeners in Fermentation Broth

For rhamnolipids quantification, the broth supernatants collected by centrifugation were diluted and adjusted to pH 2-3 and then extracted with ethyl acetate. After drying for solvent removal, the extracted materials were redissolved in 0.05 M $NaHCO_3$ and analyzed by the standard Anthrone method, with pure rhamnose solutions (1-50 mg/L) as calibration standards. The rhamnolipid concentrations in samples were then estimated by multiplying the measured rhamnose concentrations by 2.38. This value of 2.38 was based on the composition of rhamnolipid mixture produced, determined by HPLC-ELSD as shown in Table 2.

TABLE 2

Percent composition of different congeners present in a mixture of rhamnolipids produced using vegetable oil as substrate

| Sr. No. | Congeners | Molecular Weight | Number of rhamnose rings | % Composition |
|---|---|---|---|---|
| 1 | RRC8C10 | 622.7 | 2 | 4.4 |
| 2 | RC8C10 | 476.6 | 1 | 7.5 |
| 3 | RRC10C10 | 650.8 | 2 | 39.3 |
| 4 | RRC10C12:1 | 676 | 2 | 4.7 |
| 5 | RC10C10 | 504.7 | 1 | 35.3 |
| 6 | RRC10C12 | 678 | 2 | 5.0 |
| 7 | RC10C12:1 | 530.7 | 1 | 2.4 |
| 8 | RC10C12 | 532.7 | 1 | 1.4 |
| | Average molecular weight (g/gmol) | | | 582.97 |
| | Rhamnose to rhamnolipid conversion factor | | | 2.38 |

1.7 Determination of Fatty Acid Concentration in the Fermentation Broth.

To determine the fatty acid concentration of the fermentation broth, 1 mL of the broth was taken in a glass vial and was dried using a vacuum oven at 50° C. 50 μL of C13 standard was added to this dried sample along with 200 μL of $CHCl_3:CH_3OH$ (2:1 v/v) using a gas-tight syringe, and 300 μL of 0.6 M HCl (prepared in $CH_3OH$) using a plastic pipette. The vials were then tightly sealed with silicone seal cap and vortexed for 30 seconds to allow proper mixing of its contents. The sealed vials were then placed in a preheated block (Thermomixer C, Eppendorf, Hauppauge, N.Y., USA) for 1 h at 85° C. to carry out the transesterification reaction. The vials were then cooled and 1 mL of HPLC grade hexane was added and the mixture was allowed to stand for 1 h. 500 μL of the hexane phase was withdrawn into a clean HPLC vial and used for analysis using gas chromatography. Famewax column (Restek Corporation, Bellefont, Pa., USA) was used for the gas chromatography (GC-17A, Shimadzu Corp., Columbia, Md.) using a flame ionization detector (FID). A column temperature of 130° C. and detector temperature of 230° C. were used for this analysis. FAME mix, C4-C24 (Sigma-Aldrich, St. Louis, Mo., USA) was used as a calibration standard for GC-FID.

1.8 Cell Yield and Product Yield

The cell yield and product yield for the fermentation run F8 were determined to understand the substrate utilization toward biomass production and product synthesis. The cell yield was calculated towards the end of the second growth phase while the product yield was calculated at the end of the fermentation run at 144 h.

Vegetable oil was used as the carbon substrate in all the fermentation runs. The lipase produced by the bacteria hydrolyzes the vegetable oil to form free fatty acids (FA) and glycerol. The amount of vegetable oil consumed by the bacteria in a given interval was calculated by determining the residual vegetable oil left in the fermentation broth. The residual oil content was determined in terms of glycerol and free fatty acid content. For simplicity, it was assumed that the residual oil in the broth remains completely hydrolyzed at any given time. The other products of fatty acid metabolism (C14, C20, etc.) were neglected. The following equations were used to calculate the cell yield.

$$\text{Cell yield } (\%) = \frac{\text{Cell concentration}}{\text{Vegetable oil } (VO) \text{ consumed by bacteria}} \quad \text{(Eq. 4)}$$

$$VO \text{ consumed} = (VO \text{ added}) - (Gly \text{ remaining} + FA \text{ remaning}) \quad \text{(Eq. 5)}$$

The cell yield was calculated for the interval of 0 h-32 h. The percent composition of fatty acids in the fermentation broth sample taken at 32 h is given in Table 3. The percent composition of fatty acids was compared to that in initial vegetable oil. This strain of bacteria showed no preference towards any fatty acids as seen in Table 3. The cell yield ($Y_{X/S}$) was calculated to be 35.96%. This means about 36% of the total carbon substrate consumed during the period of active growth was converted to cell biomass. The calculations for cell yield were adjusted to account for the dilution factor due to sampling and nutrient addition. Determination of residual vegetable oil in the fermentation broth for cell yield calculations is shown in Table 3.

TABLE 3

The composition of fatty acids in the original vegetable oil and residual fatty acids in the fermentation broth at t = 32 h

| Sr. No. | FA | % Composition Original | % Composition Residual | Weight (g) Original | Weight (g) Residual | % Consumed |
|---|---|---|---|---|---|---|
| 1 | Palmitic | 11.91 | 7.54 | 14.81 | 1.84 | 87.59 |
| 2 | Stearic and Oleic | 29.49 | 36.70 | 36.68 | 8.95 | 75.60 |
| 3 | Linoleic | 51.94 | 50.85 | 64.60 | 12.40 | 80.80 |
| 4 | Linolenic | 6.66 | 4.91 | 8.28 | 1.20 | 85.54 |
|   | Total |   |   | 124.37 | 24.39 |   |

The product yield was calculated for the interval between 32 h-144 h in the fermentation run F8. The cells were in active stationary phase during this period and minimal cell growth occurred during this period as verified from the cell concentration profile. The composition of fatty acids in the fermentation broth at t=144 h is given in Table 4. The percent composition of the fatty acids in the fermentation broth at t=144 h was significantly different from that of the broth at t=32 h. The fermentation broth at t=144 h showed a significantly higher concentration of linoleic acid and lower concentration of stearic/oleic acid as compared to the broth at t=32 h. The product yield ($Y_{P/S}$) was calculated to be 85.88%, which means that about 86% of the consumed carbon substrate was being converted to rhamnolipids during the stationary phase. Determination of residual vegetable oil in the fermentation broth for product yield calculations is shown in Table 4, below.

TABLE 4

The percent composition of fatty acids in the fermentation broth at t = 144 h

| Sr. No. | Fatty acid | Residual (g) | % Composition |
|---|---|---|---|
| 1 | Palmitic | 0.64 | 8.32 |
| 2 | Stearic and oleic | 4.02 | 52.28 |
| 3 | Linoleic | 2.46 | 31.99 |
| 4 | Linolenic | 0.57 | 7.41 |
|   | Total | 7.69 |   |

Figure 2:
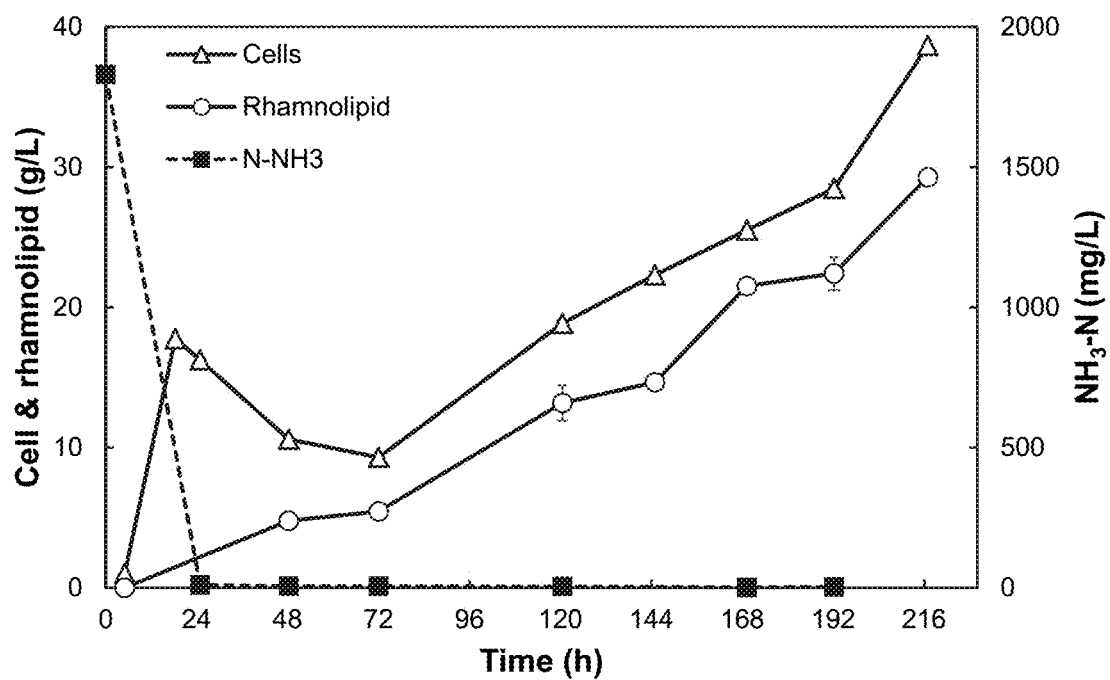
FIG. 2 is a graph showing cell, rhamnolipid and ammonium ($NH_3$—N) concentrations measured in samples taken along fermentation run F1 where, starting from 48 h, a batch of the N-source $NH_4NO_3$ which contained the equivalent of 75% of the total N amount in the initial medium, was added every 48 h.

2. Results and Discussion 2.1 Rhamnolipid Production Under Periodic N-Source Supplementation in Long Fermentations with N-Limited Initial Media The first fermentation (F1) was carried out by supplementing the N-source $NH_4NO_3$ to the broth at 75% of the total N amount in the initial medium every 48 h. The first supplementation was made at 48 h. The cell, ammonium and rhamnolipid concentration profiles measured in the periodical samples taken along the fermentation are shown in FIG. 2. Cell concentration, converted from measured intracellular protein concentration, peaked at about 18 g/L by 18 h presumably due to exhaustion of the limiting N-source in the initial medium. The N content of bacterial cells is usually in the range of 11-16% of the cell dry weight (CDW). Our preliminary experiments done in shake tubes (data not shown) gave an average cell yield from N ($Y_{X/N}$) of 6.2-6.7 (g CDW)/(g N provided) at the end of active growth phase of this P. aeruginosa culture. If all of the N sources provided were assimilated into cell mass, this cell yield corresponded to a cellular N content of 15-16% which is at the higher end of the range reported in the literature.

After reaching the maximum by 18 h, the intracellular protein concentration started to decline. The decline trend was not immediately averted by the first addition of 75% initial N-source at 48 h, but cell growth resumed by 72 h and reached almost 40 g/L at 216 h, responding to the N-source supplementation at this level. The high cell respiration rates associated with this rather active cell growth necessitated high aeration rates, which, combined with the foaming nature of rhamnolipid fermentation broth, caused excessive foaming and operational difficulties beyond 200 h. All added ammonium was consumed by the cells. Rhamnolipid production roughly paralleled the cell growth during the period of N-source supplementation (48 h-216 h), giving an average volumetric productivity of 144.7±11.9 mg/L-h. Overall, this level of N-source supplementation was found to be higher than the level required for just maintaining rhamnolipid-producing activity of non-growing cells.

The subsequent fermentations F2 and F3 were made with two lower rates of $NH_4NO_3$ supplementation to determine how different N supplementation rates would affect the rhamnolipid productivity. Results obtained in F1, F2 and F3 are summarized and compared in Table 5, below. The respective rates of N supplementation in F2 and F3 were, per 48 h, 9% and 30% of the total N in the initial medium. Because excessive foaming occurred in F1, these two fermentations were made with a lower initial total-N concentration of 1.2 g/L, instead of the 2.4 g/L used in F1, to restrict the cell concentration and required oxygen supply rates. The controlled foaming enabled longer fermentation runs, up to 500 h in F2. The average cell concentrations during the periods of N supplementation in F2 and F3 were 7.2±1.2 g/L and 9.7±1.2 g/L, respectively. During these periods, the cell concentration in F2 (with only 9% N supplementation per 48 h) remained almost constant in the long-term trend (with only small changes during the 48-h interval between two consecutive N supplementations) while the cell concentration in F3 (with 30% N supplementation per 48 h) increased moderately after the first batch of N supplementation and then plateaued (unlike the continuous, faster increase in F1). The average volumetric rhamnolipid productivity $Q_p$ in F3 was 110.1±8.2 mg/L-h, higher than that in F2 (75.9±5.5 mg/L-h); however, there was no significant difference in the specific rhamnolipid productivity $q_p$ between the two runs (11.4±0.9 versus 10.5±0.8 mg/g-h, p=0.45). The higher $Q_p$ in F3 was therefore due to its higher average cell concentration during the N supplementation period. Most importantly, the values of specific productivity $q_p$ in F2 and F3 were significantly higher than $q_p$ in F1 (8.3±0.7 mg/g-h) where the high N supplementation rate (75% per 48 h) sustained a continuous trend of slow cell growth, p=0.038 (F1 vs. F2) and 0.006 (F1 vs. F3). The results suggest that the rate of rhamnolipid production was lower when the cells were in the slow growing phase.

TABLE 5

Average cell concentration (X) and volumetric and specific rhamnolipid productivity ($Q_p$ and $q_p$) in fermentations made with different rates of N-source supplementation

| Run No. | Initial N (g/L) | Dura-tion (h) | N supplementation Rate (%/ 48 h)* | Avg. X** (g/L) | $Q_p$ (mg/L-h) | $q_p$ (mg/g-h) |
|---|---|---|---|---|---|---|
| F1 | 2.4 | 48-192 | 75 | 17.4 ± 6.4 | 144.7 ± 11.9 | 8.3 ± 0.7 |
| F2 | 1.2 | 48-505 | 9 | 7.2 ± 1.2 | 75.9 ± 5.5 | 10.5 ± 0.8 |
| F3 | 1.2 | 48-264 | 30 | 9.7 ± 1.2 | 110.1 ± 8.2 | 11.4 ± 0.9 |

*A batch of $NH_4NO_3$ solution was added every 48 h, starting at 48 h; the N amount in each batch was equivalent to the given "Rate" % of the total N in the initial medium.
**Average cell concentration was calculated for the duration of N supplementation. The large standard deviation value for F1 reflected the significant cell growth under the high rate of N supplementation.

Figure 3:
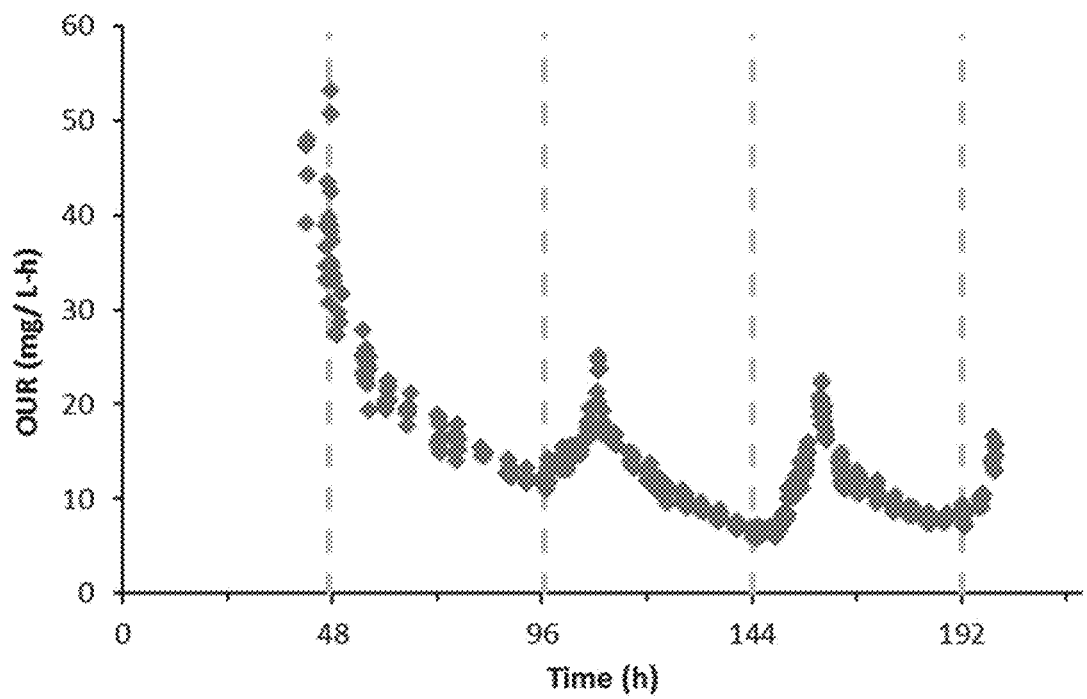
FIG. 3 is an oxygen uptake rate (OUR) profile observed in fermentation F2 where the culture was originally grown in an N-limited medium and then, starting at 48 h, was supplemented with $NH_4NO_3$ as an N source at a rate of 9% of the initial N every 48 h. The points of N supplementation were indicated by dashed vertical lines. After each N supplementation, OUR increased significantly for a short period before declining again, suggesting the occurrence of cyclic cell growth-then-decline in this fermentation.

The results obtained in F1-F3 confirmed that adequate periodic N-source addition to the *P. aeruginosa* culture originally grown on an N-limited medium can maintain rhamnolipid production in extended fermentation. However, further analysis of the oxygen uptake rate (OUR, mg/L-h) data determined along the fermentations suggested that even for F3, with the lowest N supplementation rate of 9% per 48 h, the culture went through a growth-then-decline cycle during the 48 h interval following each fed-batch N-source addition, as shown in FIG. 3. The phenomenon is not too surprising as cell growth could be supported by the freshly added N source and the decline occurred after the N source was again depleted. The extent and length of growth could depend on the amount of N source added in each fed-batch. It is possible that no or much reduced rhamnolipid production occurred during these intermittent periods of growth, resulting in suboptimal overall productivity of rhamnolipid in these fermentations. It is desirable to develop even better process designs as described in the following sections.

2.2 Rhamnolipid Production Under Periodic N-Source Supplementation in Fermentations with Non N-Limited Initial Media Because N supplementation to the cultures grown on N-limited initial media would either be too low to maintain long-term cell activity or too high to achieve high $q_p$ (specific rhamnolipid productivity) due to the triggered cell growth, it was found that the rhamnolipid production can be further improved by (1) modifying the initial medium so that the stationary phase would be induced by a nutrient component other than the N-source and (2) properly supplementing N source as required to maintain the activities of cells and enzymes essential for rhamnolipid production. To demonstrate and evaluate this approach, four fermentations (F4-F7) were conducted in two sets of batch and fed-batch (for N supplementation) fermentations, as summarized in Table 6. Compared to the earlier F2 and F3, the initial medium used for F4 (batch) and F5 (fed-batch) contained the same 0.5× of all non-N-source ingredients but doubled (1×) N-source ingredients, corresponding to a "strength" ratio of N to non-N components of 2 (higher than the N/non-N strength ratio of 1 used in F1-F3). This doubled "strength" ratio of N to non-N components was used with the assumption that the non-N source (at least one of its ingredients) would be limiting, instead of the N source. This assumption was proven correct by the observed cell concentration profile in the fed-batch F5 where a batch of N-source $NH_4NO_3$ was added daily to supply the equivalent of 75% of total N in the initial medium. This N supplementation rate was purposefully made high, twice that of F1 (75% per 48 h). If the non-N source was not limiting, one would expect to see even more cell growth than in F1 during the N supplementation period of F5. However, as given in Table 6, the cell concentrations of F5 remained essentially constant at 11.5±0.5 g/L during this period. For comparison, the cell concentrations in the batch fermentation F4 (without N supplementation) also remained relatively constant during 24-97 h (with a slight decreasing trend after about 72 h) but at a much lower level of 7.6±1.3 g/L. As the cell concentrations reported here were converted from the measured intracellular protein concentrations (using a fixed proportionality constant throughout the fermentations), the difference likely reflected the much higher protein content of cells in F5 (attained with N supplementation) than in F4 (without N supplementation). This did not affect their specific rhamnolipid productivities $q_p$ significantly; they were 23.8±1.7 and 24.4±2.6 mg/g-h, respectively, for F4 and F5 (Table 6). Nonetheless, with a significantly higher cell (protein) concentration, F5 achieved a much higher volumetric productivity $Q_p$ of 280.4±29.5 mg/L-h than did F4 ($Q_p$=180.9±13.2 mg/L-h). Most importantly, the $q_p$ values obtained in F4 and F5 with cell growth limited by the non-N source were much higher than those (ranging from 8.3 to 11.4 mg/g-h) obtained in F1-F3, where varying extent of cell growth occurred with the periodical N supplementation. Without the cell growth associated with N supplementation, the foaming was also found to be lower in F4 and F5 than that in the previous F1-F3.

In the subsequent set of fermentations F6 (batch) and F7 (fed-batch), the concentrations of non-N medium components were doubled (to 1×) in an attempt to increase cell concentrations and, correspondingly, volumetric rhamnolipid productivities. The concentrations of N-source components were also raised but only to 1.5×, giving a "strength" ratio of N to non-N components of 1.5, which was the midpoint between the strength ratios of 1 in F1-F3 and 2 in F4 and F5. The objective of choosing this midpoint strength ratio was to help us narrow down the critical strength ratio that corresponds to the switch of growth-limiting source between the N source and non-N source. Consistent with the results in F4, the stationary-phase cell concentrations in F6 during 24-96 h remained relatively constant, also with a slight decreasing trend after about 48 h; furthermore, the cell concentrations in F6 (13.5±1.5 g/L) were nearly twice that of F4 (7.6±1.3 g/L) (Table 6). The specific productivity in F6, $q_p$=25.8±0.9 mg/g-h, was also not statistically different from those in F4 and F5 (p=0.30 and 0.61, respectively).

In F7 the N-source $NH_4NO_3$ was added daily to provide the equivalent of 15% of total N in the initial medium, comparable to the 30% addition every 48 h used in F3. According to the cell growth profile observed in F3, this level of N supplementation in F7 was more than sufficient for maintaining cell activities. A trend of slight growth was observed responding to the daily N supplementation in F7, increasing from about 18 g/L at 24 h to 25 g/L at 96 h, averaging at 21.2±3.4 g/L. Corresponding to this very slight growth (with an average μ of only $4.6 \times 10^{-3}$ h$^{-1}$), the specific productivity obtained was 18.5±1.8 mg/g-h, about 25% lower than those in F4-F6 (23.8-25.8 mg/g-h) but still much higher than those in F1-F3 (ca. 8.3-11.4 mg/g-h).

Overall, the results of these two sets of fermentations F4-F7 indicated that the critical strength ratio of N to non-N components was close to but higher than 1.5. Specific rhamnolipid productivity $q_p$ by this *P. aeruginosa* strain was confirmed to be reduced even by very slow cell growth (as in F7). $q_p$ was much larger (>2-fold) from the cultures limited by the yet-to-identify non-N source component than the $q_p$ from N-limited cultures. Adequate N supplementation to maintain cell/enzyme activities in such non-N source limited stationary-phase cultures (e.g., F5) could give particularly high volumetric productivity of rhamnolipids. These 4 fermentations were only conducted for short durations of 144 h. More studies to achieve long fermentation runs with sustained productivity are described in the following sections.

TABLE 6

Volumetric and specific rhamnolipid productivity in fermentation runs with different initial N/non-N strength ratios and daily rates of N-source supplementation

| Run No. | Initial N:non-N strength | N-source added (%/24 h)* | Avg. X** (g/L) | $Q_P$ (mg/L-h) | $q_p$ (mg/g-h) |
|---|---|---|---|---|---|
| F4 | 1X:0.5X | 0 | 7.6 ± 1.3 | 180.9 ± 13.2 | 23.8 ± 1.7 |
| F5 | 1X:0.5X | 75 | 11.5 ± 0.5 | 280.4 ± 29.5 | 24.4 ± 2.6 |
| F6 | 1.5X:1X | 0 | 13.5 ± 1.5 | 348.2 ± 11.8 | 25.8 ± 0.9 |
| F7 | 1.5X:1X | 15 | 21.2 ± 3.4 | 393.0 ± 37.5 | 18.5 ± 1.8 |

*A batch of $NH_4NO_3$ solution was added every 24 h, starting at 48 h; the N amount in each batch was equivalent to the given % of the total N in the initial medium.
**Average cell concentration was calculated for the duration of N supplementation. The larger standard deviation value for F7 reflected a low extent of cell growth supported by the N source supplementation to the slightly N-limited medium.

2.3 Formation of Non-Rhamnolipid Extracellular Metabolites Under N-Source Supplementation During the above fermentations with N supplementation, both $NH_4^+$—N and $NO_3^-$—N concentrations were also measured. Even in the fermentation F5 where the N supplementation rate was the highest (75% initial total N per 24 h), the relatively large amount of added $NH_4NO_3$ (~26 g/L in 144 h) was found to be consumed practically completely by the cells without long-term accumulation of nitrate or ammonium in the broth (data not shown). The consumed N amount could not be accounted for by only assimilation into intracellular N content. We hypothesized that the supplemented N-source can result in the formation of other N-containing extracellular metabolites. The analyses of the broth using gel permeation chromatography (GPC) showed the formation of two major compounds having molecular weights of approximately 300 Da and 3000 Da, respectively. These compounds were assumed to be the characteristic N-containing phenazine pigments that *P. aeruginosa* was known to produce. They were tentatively identified as the red aeruginosin (300 Da) and the brown pyomelanin (3000 Da) based on their molecular weights. Two other commonly produced pigments by *P. aeruginosa* are pyocyanin (blue color, MW 210) and pyoverdine (yellow color, MW 1332). Pigment formation in the fermentations made in these experiments was evident and the broth color could change significantly with time and different fermentation conditions. For example, the broth at the end of F4 (batch fermentation) was in beige color while for F5 (fed-batch), the red color intensified with time and the broth appeared orange to mustard-yellow at the end. The concentrations of these two pigment compounds were significantly higher in the fed-batch fermentation F5 as compared to the batch fermentation F4 (FIG. 4), particularly the smaller compound (MW ~300, presumably red aeruginosin) which was continuously produced during the period of N supplementation. The finding supported that the provided N-source was utilized for syntheses of other extracellular metabolites. This formation of by-products under high-rate N supplementation can negatively affect the rhamnolipid yield and complicate the downstream processing for purification. On the other hand, this phenomenon may be exploited further for potentially effective production of biological pigments.

Figure 5A:
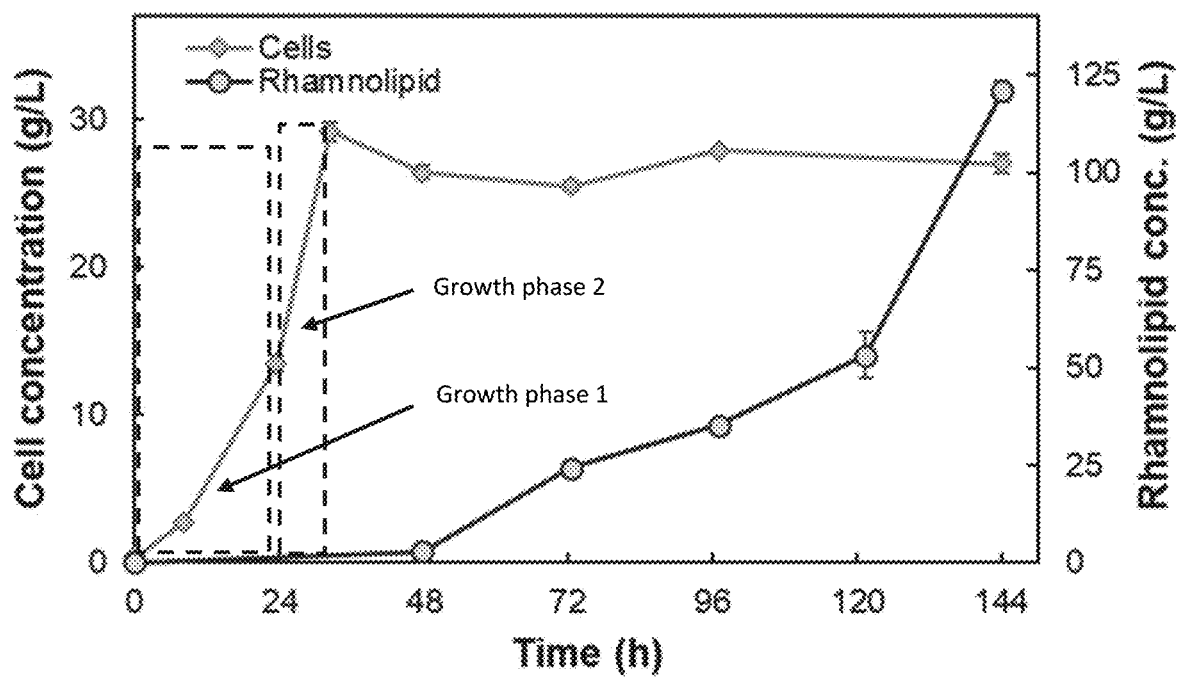
FIGS. 5A-B are graphs showing cell and rhamnolipid concentration profiles (FIG. 5A) and specific oxygen uptake rate (SOUR) profile (FIG. 5B) observed during 74-144 h, where cell concentration was built up in two growth phases and rhamnolipid was produced in the non-N limited stationary phase with continuous $NH_4NO_3$ supplementation after 74 h, to deliver a daily equivalent of 15% of the total N used in the growth phases.

2.4 Fed-Batch Fermentation Design to Achieve High Cell Concentration and Rhamnolipid Productivity According to the results obtained in previous fermentations, a new fermentation design was proposed with the objective of achieving a high cell concentration and sustained rhamnolipid productivity during prolonged stationary phase. In the earlier fermentation runs, operational difficulties associated with excess foaming occurred when cells in a culture of relatively high cell concentration (>~20 g/L) were growing actively. Actively growing cells can have almost two orders of magnitude higher specific oxygen uptake rate than the cells at the stationary phase and a high aeration rate is required to meet their high oxygen demand. This high aeration rate along with the intrinsic hydrophobic nature of the *P. aeruginosa* cells used in these experiments can cause excessive foaming and disrupt the process control. Thus, for the new fermentation F8, we designed to achieve a high cell concentration in two distinct growth phases as shown in FIG. 5A. In the first phase, cells were allowed to grow rapidly with the nutrients provided in the initial medium (N-limiting, 1.5× N source and 1.25× non-N source). The second phase started at 23.5 h with continuous, slow addition of a 300 g/L $NH_4NO_3$ solution to provide an additional 0.75× N in 9 h (ending at 32.5 h). Cell growth in this second phase was slower, regulated by the N feeding, to reduce the aeration rate required and keep the foaming manageable. By the end of the second growth phase, the total strength ratio of N source to non-N source provided was 1.8, which was high enough to ensure non-N source limitation when the culture reached the stationary phase. Starting from 74 h, the $NH_4NO_3$ solution was again continuously added to provide a daily equivalent of 15% of the total N used in the growth phases, to maintain a high rhamnolipid productivity during the extended stationary phase. As shown in FIG. 5A, this fermentation run F8 reached a highest cell concentration of 29.2 g/L by 32.5 h without creating excessive foaming and it produced 105.4 g/L rhamnolipids at 144 h with a high average volumetric productivity of 731 mg/L-h over the entire run (0-144 h). The average cell yield ($Y_{X/S}$) determined at the end of the second growth phase (32 h) was 36.0% (w/w). The rhamnolipid yield ($Y_{P/S}$) during the stationary phase (32-144 h) was determined to be 85.9% (w/w). The concentrations of glycerol and fatty acids (palmitic, stearic, oleic, linoleic and linolenic) remaining unconsumed from the substrate (vegetable oil) added were measured and used for the above yield determination. See, Tables 5 and 6.

Figure 5B:
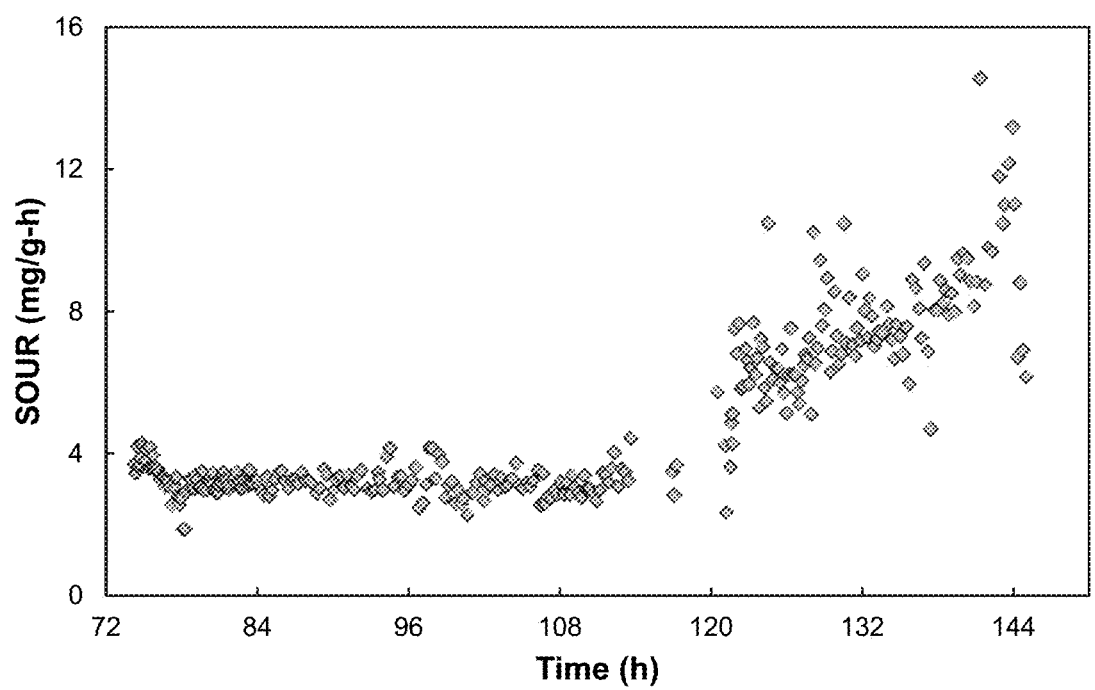

The rhamnolipid production profile appeared to have an almost constant production rate during 48-120 h and then a significantly increased production rate during 120-144 h; the former specific productivity was 26.9±2.2 mg/g-h, similar to those (24-26 mg/g-h) found in F4-F6 (Table 6), and the latter productivity was 110.6±10.6 mg/g-h. For more insights into this change of productivity, the profile of specific oxygen uptake rate (SOUR) is shown in FIG. 5B for the period after the continuous N-supplementation started, i.e., 74-144 h. Clearly the SOUR and thus activity of cells increased after about 110 h, correlating well with the increasing rhamnolipid productivity. The cells depleted the N-source provided at the end of the growth phase 2 (32.5 h) and started to experience declining (enzyme) activity due to the N-starvation, till 74 h when the continuous N supplementation began again. This declining activity could be seen in FIG. 5A as the slow decrease of cell (intracellular protein) concentration, from 29.2 g/L to 25.5 g/L in this period. It was thought that, following the onset of continuous N supplementation, it took the cells a relatively long time (110−74=36 h) to recover their activities from the previous low-activity state due to N starvation for 41.5 h (=74−32.5). This long delay in OUR response to N addition was not seen in F2, as shown FIG. 3. There were at least two differences between F2 and F8: (1) N supplementation was done in multiple batch additions in F2 but as continuous addition in F8; therefore, cells would be responding to a stimulus of high N concentration immediately after each addition in F2 but to a very low N concentration continuously added in F8; and (2) in F2 cells were under N-limitation in presence of all other nutrients while in F8, during the N-starvation period, cells were also under the limitation of at least one other growth-essential nutrient.

Figure 4:
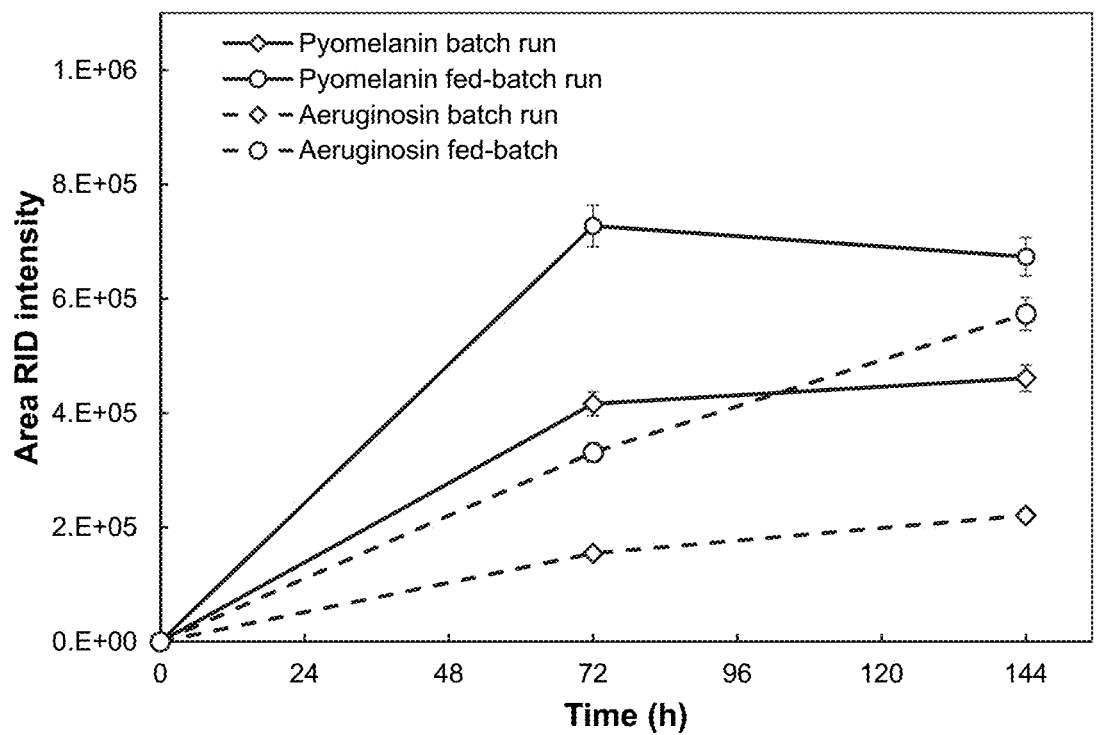
FIG. 4 is a graph showing formation of extracellular metabolites in batch fermentation F4 and in fed-batch fermentation F5 with nitrogen supplementation. The metabolites which were determined using gel permeation chromatography (GPC) with a refractive index detector (RID) had molecular weights of 300 Da and 3000 Da, tentatively identified as aeruginosin and pyomelanin respectively

Because of the above observations and considerations, we designed a subsequent fermentation F9 with same operations as in F8 except for two changes: (1) the continuous N supplementation started at 32.5 h, i.e., right after the end of the growth phase 2, and (2) the continuous N supplementation was at a 3-fold higher daily rate of 45% of total N in growth phases. These changes were made to avoid cell activity decline due to N starvation and to investigate the effect of a higher N supplementation rate. As expected, the cell concentration maxed at 29.3 g/L, essentially the same as the 29.2 g/L in F8 (data not shown). However, the cell concentration, OUR and rhamnolipid productivity all started to decline significantly after about 72 h. The cell activity never recovered till the end of fermentation at 120 h. Concurrently, the $NH_3$—N concentrations in samples were also found to jump from 5.6 mg/L at 72 h to 184.6 mg/L at 96 h. Presumably, the $NO_3^-$—N concentration accumulated to an even higher concentration as $NH_3$ was preferentially assimilated as N source before $NO_3^-$ (which was confirmed with $NO_3^-$—N and $NO_2^-$—N measurements in another fermentation showing similar phenomena). High nitrate and, particularly, nitrite concentrations can negatively affect the growth and aerobic respiration of *P. aeruginosa*. The findings in F9 suggested that a too high N-source supplementation rate might cause its accumulation to inhibitory levels and negatively affect cell activity and rhamnolipid productivity, in addition to the lower rhamnolipid yield due to excessive production of extracellular metabolites like pigments as shown in FIG. 4.

It should also be noted that fermentation F8 was carried out for longer than 144 h but the broth became increasingly too viscous and shear-thinning, eventually causing inability to disperse bubbles outside the pocket surrounding the impeller. Oxygen transfer became impaired and the broth DO later dropped to practically zero despite the increase of agitation to 1000 rpm (from the regular 800 rpm) and the continuous sparging of pure oxygen at 1 L/min. It is well known that high viscosity and shear-thinning property can negatively affect the oxygen transfer efficiency in fermentation. These observations in F8 suggested that rhamnolipid production would face a process barrier of severe oxygen transfer limitation when the rhamnolipid concentration reached beyond about 100 g/L. To avoid this barrier and further raise the rhamnolipid productivity, the fed-batch fermentation design was modified to include partial harvest and replacement of broth with fresh medium, as described in the next section.

Figure 6:
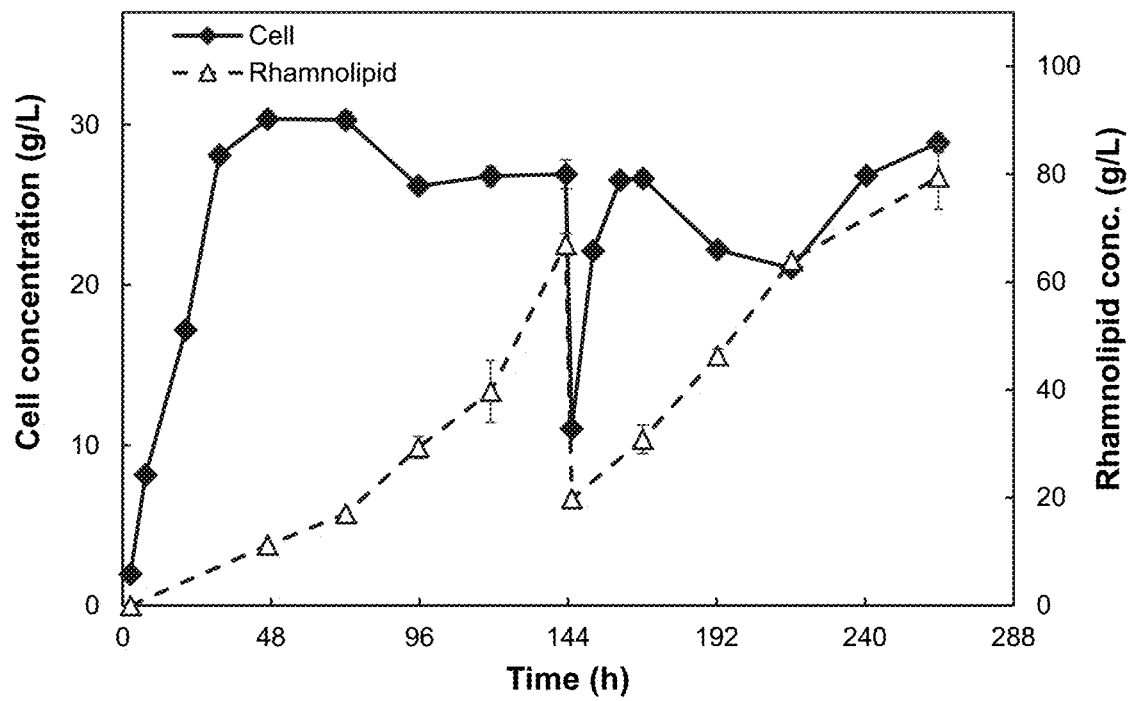
FIG. 6 is a graph showing cell and rhamnolipid concentration profiles for a two-cycle fed-batch fermentation run (F10). At the end of the first cycle (144 h), 85% of the fermentation broth volume was replaced with fresh medium containing all nutrients except for C- and N-sources which were continuously added separately.

2.5 Two Cycles of Fed-Batch Fermentation with Partial Broth Harvest to Achieve High Rhamnolipid Productivity Fermentation F10 was made to avoid the limitation in oxygen transfer efficiency associated with high broth viscosity and shear-thinning rheology due to high (>100 g/L) rhamnolipid concentrations. The initial medium and the two-growth-phase design were exactly the same as those used in the above F8 and F9, and the maximum cell concentration achieved at the end of the second growth phase was 30.3 g/L, practically reproducing the concentrations (29.2 and 29.3 g/L) attained in F8 and F9. Because of the negative results obtained in F9, the stationary-phase $NH_4NO_3$ supplementation was started after 74 h (same as in F8) and tested at a lower continuous rate, to deliver a daily equivalent of 10% total N in the growth phases, which was lower than the rate (15% N per 24 h) used in F8. The purpose was to investigate if the lower N supplementation rate could reduce the broth viscosity increase. The cell and rhamnolipid concentration profiles obtained are shown in FIG. 6. At 144 h 85% of the fermentation broth was harvested and replaced with a fresh medium containing all non-N sources at the same concentrations as those in the initial culture medium (the C-source vegetable oil was separately added as in all fermentations reported here). N-source $NH_4NO_3$ was again continuously added during 145-160 h to deliver the equivalent of 85% total N used in the two growth phases in the first cycle (0-32.5 h). Cell concentration increased back to 27 g/L at 161 h. The stationary-phase N-source supplementation continued at the same rate (10% total N per 24 h) for the next 120 h. The volumetric productivities in the two production cycles were comparable at 559.6±91.8 and 522.6±45.5 mg/L-h, respectively; the specific productivities were also comparable at 19.9±3.3 and 21.0±1.8 mg/g-h for the two cycles. The specific productivities were slightly lower than that (26.9±2.2 mg/g-h) found in F8 during 48-120 h (p=0.038), perhaps due to the lower N supplementation rate used here (10% per 24 h) than in F8 (15% per 24 h). According to the results obtained in F8-F10 with different N supplementation rates during the non-N limited stationary phase, we recommend to start adding N-source continuously without a long period of N starvation (to avoid decline in cell activity) and to use an addition rate that delivers 15% (or slightly higher) of the total N used for the growth phase(s).

More importantly, the comparable productivities obtained between the two repeated cycles in F10 supported the feasibility of achieving long-term high-productivity rhamnolipid production by using repeated fed-batch cycles. Each cycle consists of (1) a cell-growth phase, with growth rates regulated by the N-source addition rates to avoid excess foaming, (2) a rhamnolipid-production phase, with proper N-supplementation rates (15% growth-phase N per 24 h) to the non-N source limited culture, and (3) a harvest and medium-replacement phase, when the rhamnolipid concentration reaches about 100 g/L to avoid oxygen transfer limitation due to very high viscosity and shear-thinning broth rheology. The optimal decisions on the maximum cell concentration and N-addition rate in the cell-growth phase would depend on the oxygen transfer capacity of the fermentor used.

3. Conclusions

These experiments demonstrate that in one or more embodiments, the method of the present invention successfully removes the limitation of stopped or significantly decreased rhamnolipid production after certain period into the N-limited stationary phase in batch fermentation of *P. aeruginosa* in prior art methods. In fermentations with N-limited initial media, long-term rhamnolipid production, up to 505 hours tested, could be maintained with periodical N-source $NH_4NO_3$ supplementation. Optimizing the N-supplementation rate was however challenging; the rate either was lower than required for maintaining cell activity or negatively affected the specific rhamnolipid productivity $q_p$ by the intermittent cell growth created. In three such fermentations reported here with addition of 9%, 30%, and 75% of total N in the initial media every 48 h, the $q_p$ values obtained were 11.4±0.9, 10.5±0.8 and 8.3±0.7 mg/g-h, respectively. Without the negative effect on $q_p$ due to cell growth induced by N-source supplementation, fermentations made with non-N-source limited initial media and then with N-source supplementation during the stationary phase could give much higher $q_p$ of 24-26 mg/g-h. Adequate N-supplementation rates were still important and N-supplementation could stimulate production of non-rhamnolipid metabolites particularly the extracellular pigments aeruginosin and pyomelanin. According to the culture characteristics determined in the above fermentations, a new fermentation design for high rhamnolipid productivity was demonstrated. The design achieved a high cell concentration of 29-30 g/L in 32 h with two growth phases where the growth rate in the second phase was controlled by N-addition to avoid excessive foaming. The subsequent non-N-limited stationary-phase rhamnolipid production was evaluated at different N-supplementation rates: 10%, 15%, and 45% per 24 h. A highest rhamnolipid concentration of 105 g/L was achieved after 144 h at the optimal continuous addition of 15% growth-N per 24 h, corresponding to an overall (0-144 h) productivity of 731 mg/L-h. At this high rhamnolipid concentration, the broth became too viscous which impeded the oxygen transfer capacity to maintain suitable DO. The final optimal fermentation design demonstrated in these experiments was to use repeated cycles that include the following periods in each cycle: (1) 2-phase growth to high cell concentration limited by non-N substrates, (2) active production to about 100 g/L rhamnolipids, with continuous addition of 15% growth-N per 24 h, and (3) harvesting of part (85%) of the broth and replacement with fresh medium to start the next cycle of cell growth.

Example 2

Evaluation of Rhamnolipid Productivity in Long Fermentation Runs

The effects of different ways of periodic N-source addition on the sustainability of long-term rhamnolipid production and the yield and productivities obtained, both volumetric (g/L-h) and specific (g/gCDW-h, where CDW stands for cell dry weight) were evaluated. The objective was to improve rhamnolipid productivity in long fermentation runs and improve understanding of the bacterial metabolic processes involved in rhamnolipid production to design and devise techniques to improve the product concentrations and yields which can improve the overall process economics.
Materials and Methods
Bacterial Culture Preparation The *Pseudomonas aeruginosa* bacterium used in this study was the same rhamnolipid-producing bacterium used in Example one above. The seed culture was activated and grown as set forth above in Example 1.
Fermentor Study As in Example 1, these experiments were carried out in 2-L fermentors (BIOFLO 110, New Brunswick Scientific) containing 1 L fresh medium which was agitated at 800 rpm with two 6-blade turbines. The temperature was maintained at 32° C. Dissolved oxygen concentration (DO) was set at 10% (air saturation) with automatic adjustment of the flow rate of pure oxygen; nonetheless, DO could fluctuate up to a range of 5%-50% during periods of faster metabolic changes. The pH was allowed to drop naturally due to cell metabolism from the initial value of 7.0 to the control set point of 5.70±0.05 and was subsequently controlled by addition of 1 N $H_2SO_4$ or NaOH.

The composition and component concentrations of the nitrogen source, carbon source, and non-nitrogen source used for the fermentation medium were as set forth above in Example 1. The concentrations of these components (excluding the vegetable oil) were considered as 1×. The medium pH was adjusted to 7.0 before autoclaving. Additionally, a 10 g/L betaine solution was filter-sterilized and added as an osmoprotectant, at a final concentration of 0.5 mM in the medium. Nitrogen was the limiting nutrient in the initial medium for all fermentation runs.
Shake Tube Study The shake tube study was conducted in a Thermo Scientific MaxQ 5000 shaker. Shake tube (or flask) experiments were often plagued with substantial side effects of uncontrollable pH and/or DO limitations. To avoid/minimize these, 50 g/L glycerol was used as the sole C source in these experiments, instead of vegetable oil. This change was made according to preliminary experiments that showed much lower pH-decreasing extent with glycerol as C source than with vegetable oil. Further, the N-source components in the medium were 0.25 g/L yeast extract, 0.25 g/L peptone and 0.21 g/L $NH_4NO_3$, corresponding to only 5% of the total N in the 1× medium used in the fermentor study. The low total N-source concentration used here was designed to support growth to much lower cell concentrations, thus minimizing the concern of DO limitation. The use of $NH_4NO_3$ instead of $NH_4Cl$ was to avoid the significant pH drop caused by $NH_3$ consumption in the latter case; *P. aeruginosa* assimilated both $NH_4^+$ and $NO_3^-$ as N-source in the former case, giving a slight pH-increasing potential to partially offset the pH decrease associated with release of acidic metabolites. All other medium components were also 20 times diluted as compared to the 1× medium used for the fermentor study.

The glass tubes used in this study had diameter of 2.2 cm and length of 15 cm, with an effective headspace of 10.5 cm. The tubes were covered with sterile cheesecloth and laid slanted at a 30° angle to improve oxygen transfer. The bacterial culture was inoculated at 2% v/v at the start of experiments. The final broth volume in the tubes was measured at every sampling point to account for the water loss by vaporization and the cell and rhamnolipid concentrations were accordingly normalized. Experiments were conducted in triplicates with three different tubes for each system.
Analytical Techniques The analytical methods used in this work are briefly described here. Intracellular protein concentrations, measured by the standard Bradford method, were converted to cell dry-weight concentrations using a pre-established calibration. Glycerol analysis was done by high performance liquid chromatography (HPLC, Model LC1100, Agilent Technologies, Santa Clara, Calif.) equipped with a refractive index detector (RID-10A). The ammonium concentrations in samples taken along fermentation were measured using an ammonia electrode (High Performance Ammonia Ion Selective Electrode, Thermo Scientific, Beverly, Mass.). This probe allowed accurate measurement in the range of 1-1000 mg/L $NH_4^+$—N. Rhamnolipid analysis was done by the standard anthrone method and by using HPLC with an evaporative light scattering detector (ELSD, Model 300, SofTa Corporation, Thornton, Colo.). For the anthrone analysis, the measured rhamnose concentrations were multiplied by 2.38 to estimate the rhamnolipid concentrations.

This value of 2.38 was based on the composition of rhamnolipid mixture produced, determined by HPLC-ELSD.

Calculations

There was a continuous change in the volume of broth during the fed-batch fermentation due to addition of acid, base, antifoam agents, and nutrients as well as sample removal from the fermenter. The volume changes were considered and adjusted while computing different concentration profiles, to determine the intrinsic culture properties. The effective broth volume at every sampling time was recorded; and average specific cell growth rate ($\mu$) and specific product formation rate ($q_p$), and the time-averaged cell biomass ($X_{t,avg}$) were calculated for every interval between two consecutive sampling times using the following equations using Equations 1-3, as set forth above, where subscripts 0 and 1 denote the respective samples at t and (t+$\Delta$t). In these equations, X and P refer to the weights of cell biomass and rhamnolipid product (X=x V and P=p V, where x, p and V are respectively the cell and rhamnolipid concentrations and broth volume determined at each sampling time). During the interval between two sampling points, X changed only by cell growth and P by production while x and p would also be affected by the continuously changing broth volume. The time averaged cell concentration in a specific interval was obtained by considering the exponential cell growth during the interval, with the average specific growth rate $\mu$. All the concentration profiles described in this experiment were adjusted for the volume change during the fermentation runs.

Experimental Design

The current study was conducted to optimize the rate of N-source supplementation to obtain high and sustained rhamnolipid productivity. The shake tube study was first conducted at different rates of periodic N-source addition. The objective was to identify/narrow the range of supplementation rates that gave higher final rhamnolipid concentrations. Nitrogen was used as the limiting component in the initial medium. The supplemented N-source was the inorganic ammonium nitrate in these experiments. Subsequently, three fermentation runs were carried out in a fed-batch mode at different rates of N-source addition. The average cell concentrations and volumetric and specific productivities of rhamnolipids during these runs were calculated. As an index to reflect how active the cells' metabolism was at different stages of fermentation, specific oxygen uptake rates (SOUR) were determined from the online monitored DO profiles. This was possible because DO was maintained by short alternating on/off periods of oxygenation. During the periods of no oxygenation (or aeration), DO dropped essentially linearly with time and the decreasing slope was taken as the oxygen uptake rates (OUR, mg $O_2$/L-min). Then, SOUR (mg $O_2$/gCDW-min) can be calculated as OUR divided by the cell concentration (X, g/L) during that period.

Results and Discussions

Optimization of N-Source Supplementation Rate

Figure 7A:
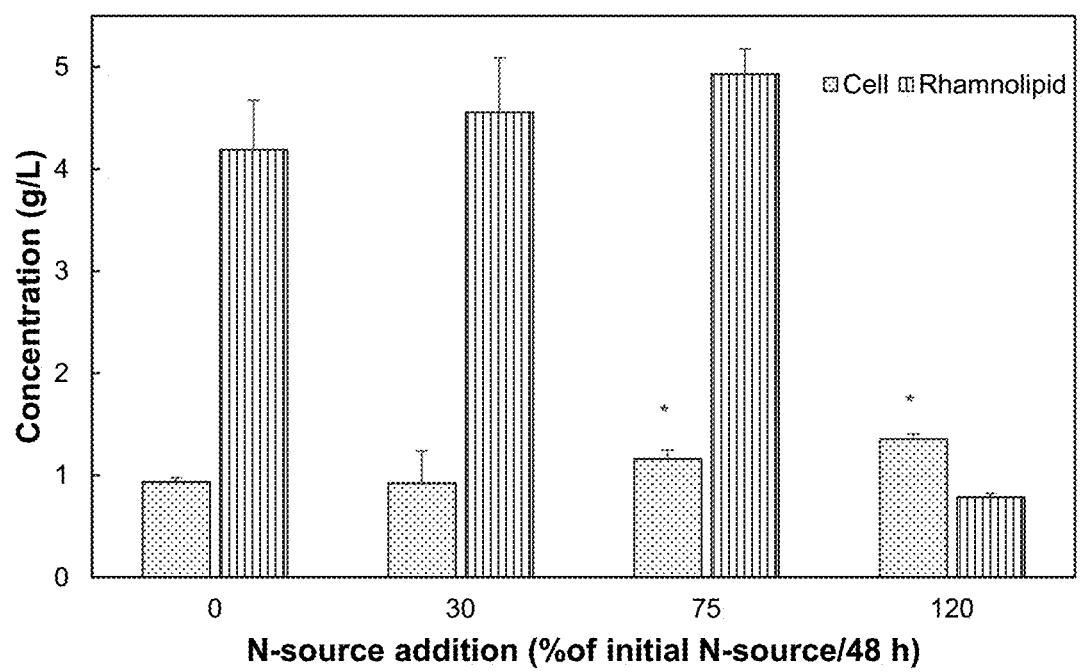
FIGS. 7A-B are graphs showing final cell and rhamnolipid concentrations in shake tube study conducted with different rates of periodic N-source addition (FIG. 7A) and glycerol consumption in corresponding systems (FIG. 7B). The study was conducted in triplicates. * indicates p-value <0.05 as compared to control
Figure 7B:
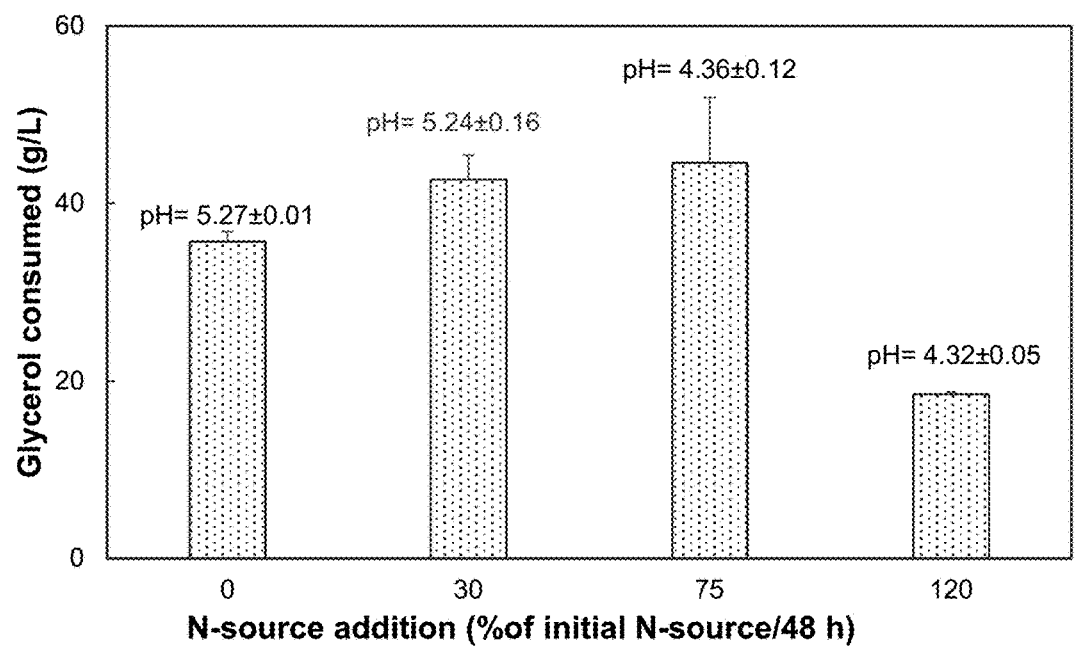

The shake tube study was conducted for 12 days with periodic N-source addition in form of ammonium nitrate. The study was conducted to provide N-source supplementation at different rates of 30%, 75%, and 120% of the initial N-source every 48 hours. The final cell and rhamnolipid concentrations in all systems were measured (See, FIGS. 7A-B). The cell concentration in systems with 75% and 120% of N-source addition was significantly higher that the control system (no supplementation). Higher periodic N-source addition to a nitrogen-limited medium resulted in controlled growth phase leading to a substantially higher final cell concentration. However, no significant increase in final rhamnolipid concentration was seen with increasing rate of supplementation. Although it was clear that a high N-source supplementation rate led to significantly higher cell concentration, the optimal rate of supplementation for maximizing rhamnolipid productivity could not be evaluated from this study. As poor pH control is one of the major limitations in shake flask studies, it is likely that uncontrollable pH affected cell growth and rhamnolipid productivity in systems with higher rates of N-source supplementation (See, FIGS. 7A-B).

Periodic N-Source Supplementation in Fed-Batch Mode in Long Fermentation Runs

As the results from shake tube studies were inconclusive for optimization of N-source supplementation rate to obtain sustained and high rhamnolipid productivity, fermentor studies were conducted. A fed-batch fermentation run was first carried out by supplementing 75% of the initial N-source to the medium every 48 hours (FA1). The cell and rhamnolipid concentration profiles are shown in FIG. 2. The N-source supplementation in this run resulted in a period of active growth in the later stages of fermentation. The high cell respiration during the active growth phase resulted in increased oxygen demand leading to high aeration rate. This high aeration rate combined with foaming behavior of rhamnolipids led to formation of stable foam in the fermentor, thereby causing operational difficulties beyond 200 h. The volumetric productivity in this run was 144.7±11.9 mg/L-h during the period of N-source supplementation (48 h-216 h). This productivity was significantly lower than the volumetric productivity of 220 mg/L-h obtained in batch fermentation run in our previous study.

Two fermentation runs (FA2 and FA3) with different rates of N-source supplementation were conducted to understand the effect of periodic N-source addition on rhamnolipid productivity. These runs were conducted using initial nitrogen concentration of 1.2 g/L, instead of 2.4 g/L as used in run FA1. It should be noted that in these fermentation runs, nitrogen was the limiting component in the initial medium, which was responsible for inducing the stationary phase. Thus, the highest cell concentration attainable by the culture at the end of the exponential growth phase would be determined by the initial nitrogen concentration. The nitrogen content of a bacterial cell usually ranges between 11-16% of the total cell dry weight. For example, our shake tube study showed that *P. aeruginosa* contains about 15-16% nitrogen per unit dry weight at the end of active growth phase. The maximum cell concentration attainable in runs FA2 and FA3 was half of that in FA1. This allowed controlled foaming and thereby facilitating longer fermentation runs. The rate of N-source supplementation in FA3 was three times that of run FA2 (Table. 7). The average cell concentrations after the initial growth phase in runs FA2 and FA3 were 7.2±1.2 g/L and 9.7±1.2 g/L respectively. The reason for this difference in average cell concentrations in the two runs was slow-growing phase induced by N-source supplementation to the nitrogen-limited culture medium. The growth rate in this slow-growing phase was directly proportional to the rate of N-source supplementation. The average volumetric productivity $Q_{pv}$ in FA3 (110.1±8.2 mg/L-h) was higher than that in FA2 (75.9±5.5 mg/L-h); however, there was no significant difference in the specific rhamnolipid productivity between the two runs (11.4±0.9 versus 10.5±0.8 mg/g-h). The higher volumetric productivity in FA3 was therefore due to its higher average cell concentration during the run. This suggests that the rate of rhamnolipid production was lowered during the interval when the cells were in a slow growing phase.

TABLE 7

Average cell concentration, volumetric and specific rhamnolipid productivity in fermentation runs with different rates of N-source supplementation

| Run No. | Initial nitrogen (g/L) | Type of N-source addition | N-source added (%/48 h) | Avg. X* (g/L) | $Q_{p V}$** (mg/L-h) | $q_p$** (mg/g-h) |
|---|---|---|---|---|---|---|
| FA2 | 1.2 | Inorganic | 9 | 7.2 ± 1.2 | 75.9 ± 5.5 | 10.5 ± 0.8 |
| FA3 | 1.2 | Inorganic | 30 | 9.7 ± 1.2 | 110.1 ± 8.2 | 11.4 ± 0.9 |

*Average cell concentration during the stationary phase;
**The volumetric and specific productivities were calculated for the interval from the end of active growth phase to the end of the fermentation run.

It can be inferred from these observations that the rhamnolipid productivity of an individual bacterial cell decreases even when it is in a phase of slow growth.

Measurement of Specific Oxygen Uptake Rate as an Index of Metabolic Activity

It was seen that the periodic addition of N-source to *P. aeruginosa* cells in stationary phase during fermentation can induce a brief growth period. This is because the initial stationary phase was induced using nitrogen as the limiting component in the medium, while other components were in excess. Thus, any small addition of N-source during the stationary phase resulted in a brief period of growth in which cell biomass corresponding to the added N-source was produced. It is believed that this short period of controlled growth increases the metabolic activity of the culture and results in higher oxygen demand. The metabolic activity of a microbial culture can be described by using an index called specific oxygen uptake rate (SOUR), which is an indicator of cell response to the changing medium conditions. SOUR is essentially the amount of oxygen utilized by a unit mass of bacteria during a given time interval. The SOUR can be calculated using the equations given below.

The governing equation of oxygen mass balance in a well-mixed liquid phase is given as follows:

$$\frac{dC_{O2}}{dt} = k_L a(C_{O2}^* - C_{O2}) - q_{O2} \cdot C_x \quad \text{(Eq. 6)}$$

$$\frac{-1}{C_x} \cdot \frac{dC_{O2}}{dt} = q_{O2} = \text{SOUR} \quad \text{(Eq. 7)}$$

The first equation describes the rate of accumulation of oxygen in the fermentation broth. The first term on right hand side of the second equation refers to the rate of transfer of oxygen from gas phase to liquid phase while second term denotes the oxygen consumption rate of the microbial culture. The term $q_{O2} \cdot C_x$ represents the oxygen uptake rate (OUR) by the microorganisms, with $q_{O2}$ being the specific oxygen uptake rate (SOUR) and $C_x$ is the concentration of microorganisms in the reactor. The forth equation is obtained by assuming that no interchange of oxygen occurs between the gas phase and the liquid phase during the test period. Thus, SOUR can be easily calculated using the dissolved oxygen profile obtained during the fermentation run to quantify the metabolic state of the bacterial culture.

Figure 8:
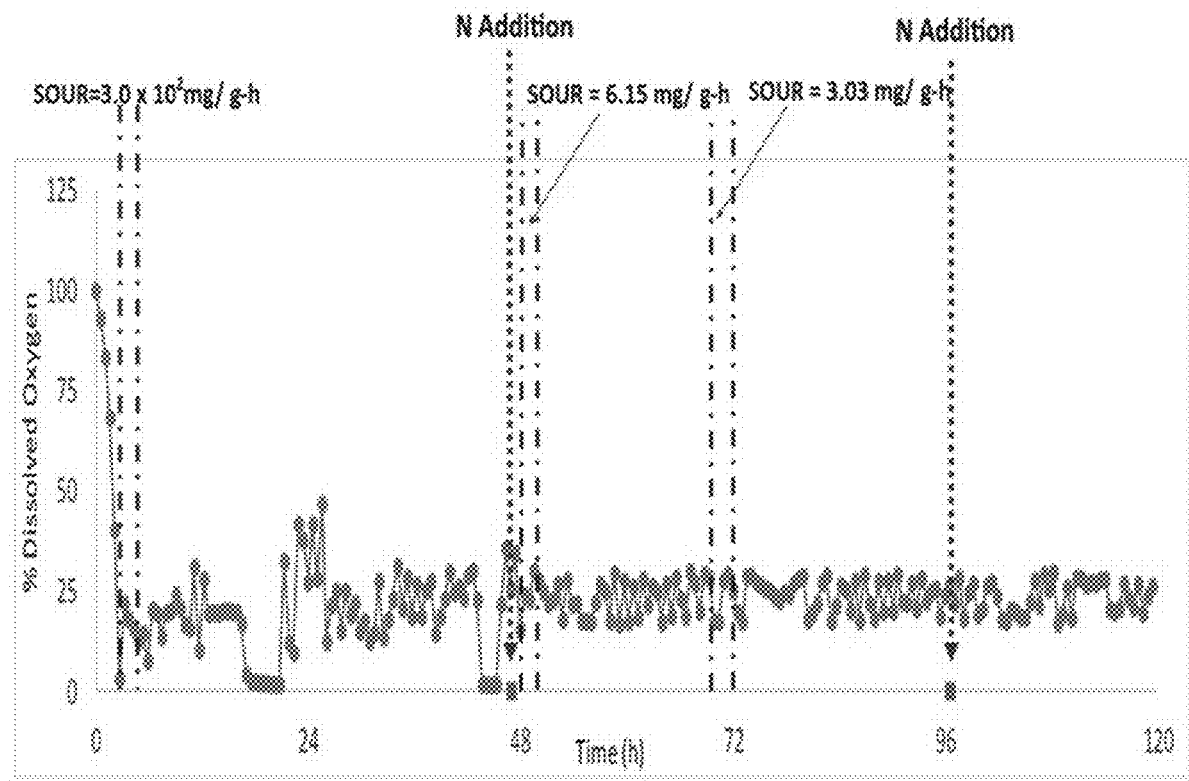
FIG. 8 is graph showing a dissolved oxygen profile and values of specific oxygen uptake rate (SOUR) during the different stages of a fed-batch fermentation run. N-source was supplemented periodically at a rate of 9% of the initial after every 48 hours.

Oxygen is an important substrate in aerobic fermentations, which is required for growth, maintenance, and product syntheses. Oxygen uptake rate is an important physiological characteristic of the culture, which is used for predicting culture viability and for optimization of fermentation processes. The dissolved oxygen profile of fermentation run FA2 with periodic N-source supplementation (9% of initial N-source every 48 hours) is shown in FIG. 8. The SOUR was calculated for this fermentation run at different stages of the bacterial growth cycle as depicted in Table. 8. The reported values for SOUR were an average of 25 values during the given time interval. The SOUR values were 299.95 mg/g-h and 3.70 mg/g-h during exponential phase and stationary phase respectively. The oxygen consumption was up to two orders of magnitude higher during the active growth phase as compared to the stationary phase. This high oxygen demand during the active growth phase can be attributed to rapid consumption of carbon substrate and production of biomass during the active growth phase. The addition of N-source to resting cells can induce a "regulated growth phase", where there is a momentary surge in metabolic activity of the bacterial culture. The SOUR value during the regulated growth phase was twice of that during the stationary phase, which indicates an increased metabolic activity when N-source is supplemented to a resting cell culture.

TABLE 8

Average values of specific oxygen uptake rates (SOUR) in different stages of the fermentation run

| Sr. No. | Time interval (h) | Period of growth cycle | SOUR (mg/g-h) | OUR (mg/L-h) |
|---|---|---|---|---|
| 1 | 2.8-3.6 | Exponential phase | 299.95 | 77.65 |
| 2 | 47.2-48.9 | Regulated growth phase | 6.16 | 32.81 |
| 3 | 52.7-53.8 | Stationary phase | 3.70 | 19.69 |
| 4 | 70.8-72.8 | Stationary phase | 3.03 | 16.02 |

Figure 9:
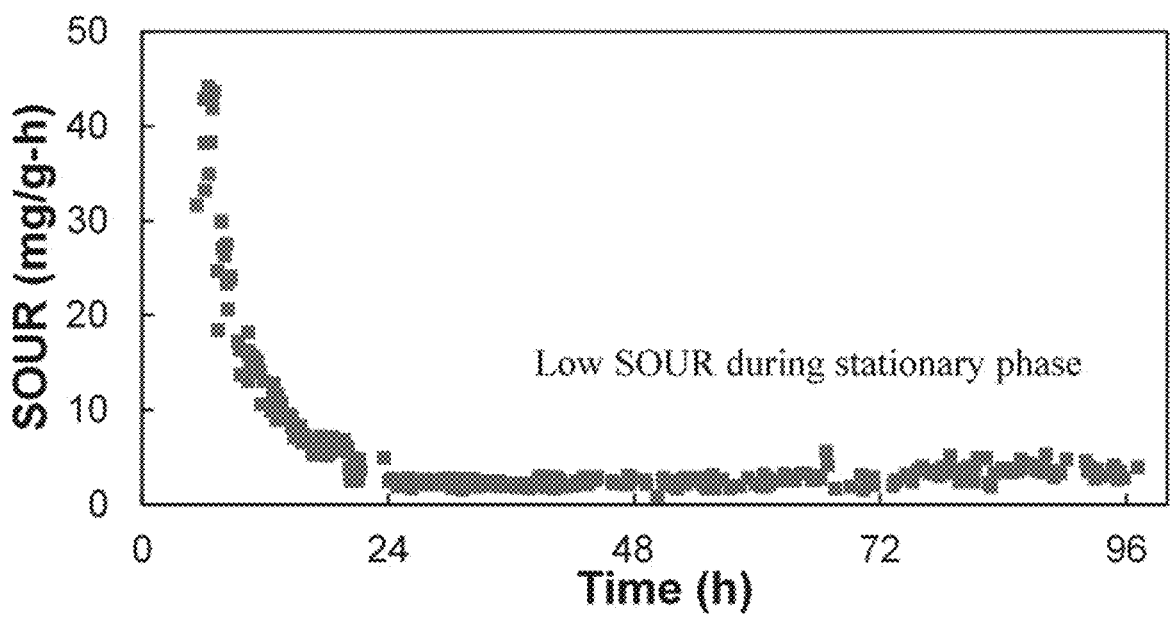
FIG. 9 is a graph showing the specific oxygen uptake rate (SOUR) during a batch fermentation run.

The SOUR profile for a typical batch fermentation is shown in FIG. 9. When nitrogen source was periodically supplemented to the nitrogen deficient culture in a fed-batch mode of fermentation, there was a transitory increase in metabolic activity, as seen from the SOUR profile in FIG. 3. It was observed that addition of N-source in one-shot causes instantaneous growth phase which resulted in a sudden increase in the oxygen uptake rate of the bacterial cells. This sudden rise in SOUR increases the demand for oxygen requiring higher aeration rates, which can subsequently lead to operational problems such as foaming. One approach to avoid excessive foaming is to add very small amount of N-source continuously over relatively short time instead of supplying it all in a single shot. This way, the cells grow progressively with the added N-source but only for short period before entering the stationary phase, which will translate to lower "time averaged" respiration rate. The period of high oxygen demand in this case will be shorter leading to lower aeration requirement which would translate to lesser and controllable foaming.

Example 3

Evaluation of Excessive Foam Formation

In these experiments, different feeding strategies were evaluated to achieve a final rhamnolipid concentration of 105 g/L and overall volumetric productivity of 731 mg/L-h. A high cell concentration is desired during the fermentation process for achieving high volumetric productivity. However, as the cell respiration rate is directly proportional to the cell growth rate, building up a high cell concentration often leads to excessive foam formation due to high aeration rates. Thus, a two-stage fermentation design was developed in this study by using controlled feeding of N-source to achieve sustained high cell and rhamnolipid concentration profiles.
Materials an Methods
Bacterial Culture Preparation The Pseudomonas aeruginosa bacterium used in this study was the same rhamnolipid-producing bacterium used in Example 1 above. The seed culture was activated and grown as set forth above in Example 1.
Fermenter Study As in Examples 1 and 2, these experiments were carried out in 2-L fermenters (BIOFLO 110, New Brunswick Scientific) containing 1 L fresh medium which was agitated at 800 rpm with two 6-blade turbines. The temperature was maintained at 32° C. Dissolved oxygen concentration (DO) was set at 10% (air saturation) with automatic adjustment of the flow rate of pure oxygen; nonetheless, DO could fluctuate up to a range of 5%-50% during periods of faster metabolic changes. The pH was allowed to drop naturally due to cell metabolism from the initial value of 7.0 to the control set point of 5.70±0.05 and was subsequently controlled by addition of 1 N $H_2SO_4$ or NaOH.

The composition and component concentrations of the nitrogen source, carbon source, and non-nitrogen source used for the fermentation medium were as set forth above in Example 1. The medium pH was adjusted to 7.0 before autoclaving. Additionally, a 10 g/L betaine solution was filter-sterilized and added as an osmoprotectant, at a final concentration of 0.5 mM in the medium.

Fermentation runs were conducted using different proportions of nitrogen and non-nitrogen components in the initial medium, as shown in Table. 9, below.

TABLE 9

The proportion of nitrogen and non-nitrogen source components in the initial medium for different fermentation runs

| Fermentation run | N-source | Non-N source |
|---|---|---|
| FB1 | 1X | 0.5X |
| FB2 | 1X | 0.5X |
| FB3 | 1.5X | 1X |
| FB4 | 1.5X | 1X |
| FB5 | 1.5X | 1.25X |
| FB6 | 1.5X | 1.25X |
| FB7 | 1.5X | 1.25X |

Analytical Techniques

Figure 10:
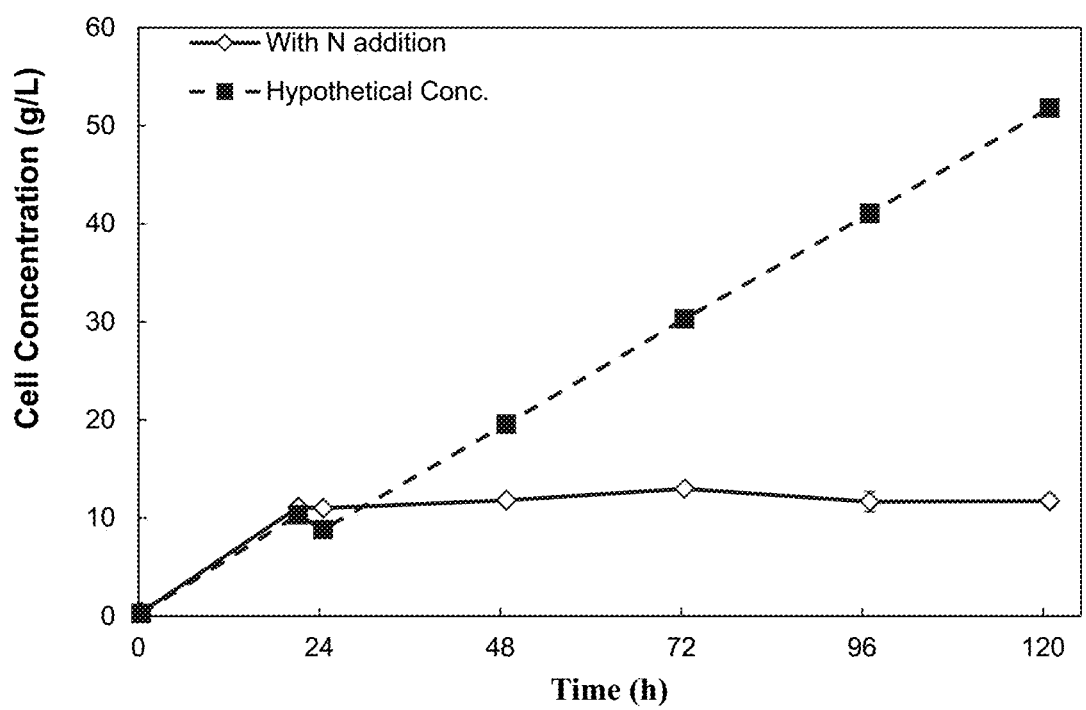
FIG. 10 is a graph showing cell concentration in fed-batch fermentation run (F5) with N-source supplementation. The stationary phase was induced by non-nitrogen component of the medium. The dashed line shows hypothetical cell concentration if all the supplemented N-source was converted into biomass
Figure 11:
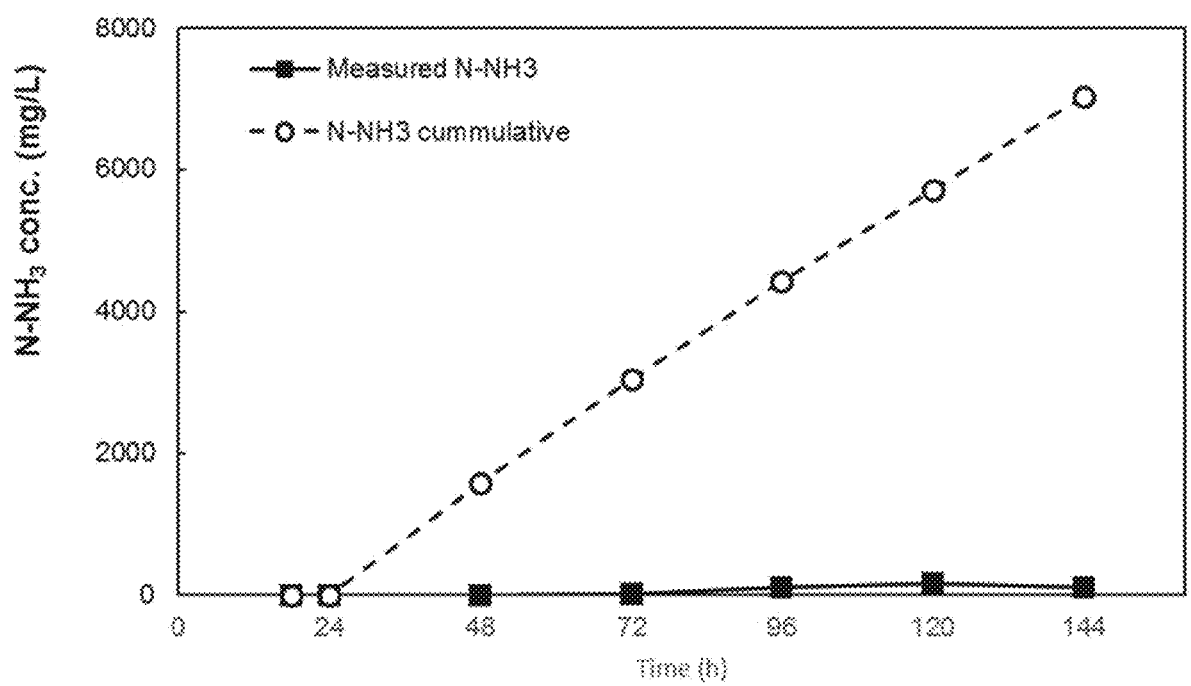
FIG. 11 is a graph showing a concentration profile of nitrogen in terms of N—NH3 in fermentation run FB2. FB2 was a fed-batch fermentation run with N-source supplementation at rate of 75% of initial nitrogen after every 24 hours. The N-source addition was started at 24 hours.
Figure 12:
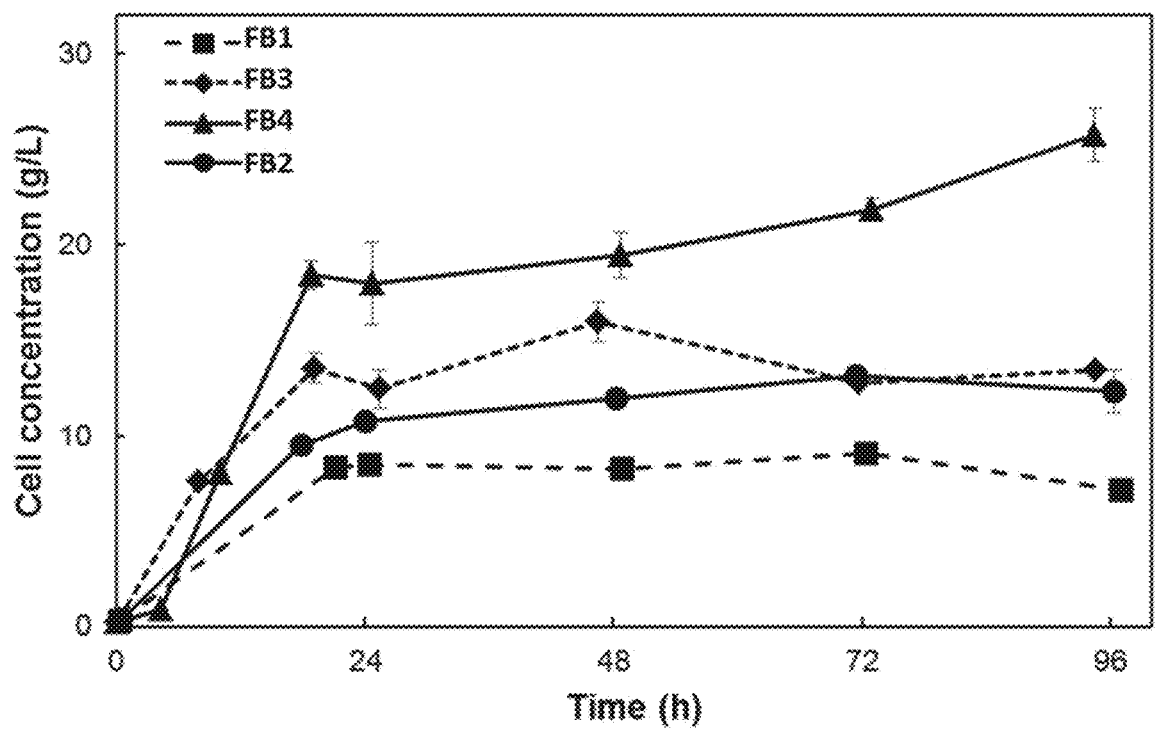
FIG. 12 is a graph showing cell concentration profiles in fermentation runs FB1-FB4. FB1 and FB3 were batch fermentation runs while FB2 an FB4 were fed-batch runs with N-source supplementation at rate of 75% and 15% of initial nitrogen every 24 hours.

The analytical methods used in these experiments are briefly described here. Intracellular protein concentrations, measured by the standard Bradford method, were converted to cell dry-weight concentrations using a pre-established calibration. Glycerol analysis was done by high performance liquid chromatography (HPLC, Model LC1100, Agilent Technologies, Santa Clara, Calif.) equipped with a refractive index detector (RID-10A). The ammonium concentrations in samples taken along fermentation were measured using an ammonia electrode (High Performance Ammonia Ion Selective Electrode, Thermo Scientific, Beverly, Mass.). This probe allowed accurate measurement in the range of 1-1000 mg/L $NH_4^+$—N. Rhamnolipid analysis was done by the standard anthrone method. For the anthrone analysis, the measured rhamnose concentrations were multiplied by 2.38 to estimate the rhamnolipid concentrations. This value of 2.38 was based on the composition of rhamnolipid mixture produced, determined by HPLC-ELSD. The extracellular components of the fermentation broth were analyzed by gel permeation chromatography (GPC) using Pb aquagel-OH 5 µm column (Agilent Technologies, Lanarkshire, UK). The standard calibration curve obtained by using polyethylene glycol/oxide standards (EasiVial PS-H, Agilent Technologies, Santa Clara, Calif.) was used to determine the molecular weights of the extracellular components in the broth.
Experimental Design In this study, fermentation runs were conducted in batch and fed-batch modes at two different proportions of nitrogen to non-nitrogen components in the initial medium. This was done to obtain the ratio which would enable stationary phase to be induced by non-nitrogen component in the initial medium. The effect of N-source supplementation on volumetric and specific productivities of rhamnolipid was inspected. Based on the data obtained from the first four fermentation runs, a two-stage fermentation design was developed by using controlled feeding of N-source to achieve sustained high cell and rhamnolipid concentration profiles. Finally, a sequentially-fed batch fermentation was conducted to obtain high rhamnolipid productivity in a long fermentation run.
Results and Discussions
Fed-Batch Fermentation Using Non-N Source Limitation Periodic N-source addition to a nitrogen limited medium can help in sustaining high rhamnolipid productivity in long fermentation runs. However, this N-source supplementation also triggered the cells to grow proportionally to the added nitrogen. This induction of growth phase to the cells during the stationary phase was negatively affecting the rhamnolipid productivity. Thus, to overcome the negative impact of a controlled growth phase, it is desirable to maintain the cell culture in a stationary phase throughout the fermentation run, without any loss in its metabolic activity. To accomplish this, the concentration of the components in the initial medium was modified so that the stationary phase would be induced by a component other than nitrogen. In the fermentation runs FB1 and FB2, the ratio of non-nitrogen components to nitrogen was adjusted to 2 in the initial medium. This ensured that some non-nitrogen component was completely depleted before nitrogen, thereby initiating the onset of the stationary phase. This induction of the stationary phase by non-nitrogen component ensured that there was no cell growth when N-source was supplemented after the end of the initial exponential growth phase. FIG. 10 shows cell concentration profile of fermentation run FB2 where the stationary phase was induced by non-nitrogen component. In this run, N-source was added in form of ammonium nitrate at a rate of 75% of initial nitrogen content after every 24 hours but the cells continued to remain in the stationary phase. The hypothetical cell concentration profile is also depicted in FIG. 10, which shows the increase in the cell biomass if the supplemented N-source was converted to biomass without any restriction from other medium components. The concentration profile of nitrogen in terms of N—$NH_3$ for the fermentation run FB2, is depicted in FIG. 11. Likewise, the concentration profile of nitrogen in terms of N—$NO_3^-$ showed similar trend (data not shown). Thus, the N-source supplemented during the run FB2, was completely consumed by the bacteria, without manifesting as increase in the biomass.
Effect of N-Source on Rhamnolipid Productivity To understand the effect of N-source supplementation on rhamnolipid productivity, two sets of batch and fed-batch fermentations were conducted. In the fermentation runs FB1 and FB2, the ratio of nitrogen to non-nitrogen components was 2; while this ratio was 1.5 for runs FB3 and FB4. FB1 and FB3 were batch fermentation runs while FB2 and FB4 were operated in fed-batch mode with N-source supplementation. The first objective of this experiment was to identify the proportion of nitrogen to non-nitrogen components in the initial medium which would result in induction of stationary phase by the non-nitrogen component. The second objective was to understand the effect of N-source supplementation on volumetric and specific productivity in these runs. It is important to determine whether N-source supplementation has any significant benefits on rhamnolipid productivity in fermentation runs in this design. The cell concentration profile for the four runs FB1-FB4 is shown in FIG. 12. It was observed that there was no controlled growth phase after the end of initial growth phase in runs FB1, FB2, and FB3; however, a slow-growing behavior was observed in run F4. This indicated that the stationary phase in runs FB3 and FB4 was induced by nitrogen, which explains the controlled cell growth in run FB4 on supplementation of N-source. It can be concluded that a nitrogen to non-nitrogen component ratio of 1.5 was not capable of inducing the stationary phase by the non-nitrogen component.

The volumetric productivities of FB1 and FB2 were 180.9±13.2 mg/L-h and 280.4±29.5 mg/L-h respectively (See, Table 10). Thus, the higher volumetric productivity of the fed-batch run as compared to the batch run indicated higher metabolic activity of culture under N-source supplemented conditions. However, the volumetric productivity of run FB4 was not significantly higher than FB3, presumably due to presence of controlled growth phase which was triggered by N-source addition in FB4. The specific productivity in FB1, FB2, and FB3 was comparable but was reduced significantly in run FB4. It should be noted that all 4 runs were only conducted for short durations of 144 h. This was done with an objective of understanding the initial cell growth behavior and the effect of N-source addition on rhamnolipid productivity. More studies to achieve long fermentation runs with sustained productivity are described in the following sections.

TABLE 10

Volumetric and specific rhamnolipid productivity in fed-batch fermentation runs with different rates of N-source supplementation with the stationary phase induced by non-nitrogen component

| Run No. | Initial ratio N/non-N | N-source added (%/48 h) | $Q_{PV}$ (mg/L-h) | $q_p$ (mg/g-h) |
|---|---|---|---|---|
| FB1 | 2 | 0 | 180.9 ± 13.2 | 23.8 ± 1.7 |
| FB2 | 2 | 150 | 280.4 ± 29.5 | 24.4 ± 2.6 |
| FB3 | 1.5 | 0 | 348.2 ± 11.8 | 25.8 ± 0.9 |
| FB4 | 1.5 | 30 | 393.0 ±3 7.5 | 18.5 ± 1.8 |

Note:
The productivity terms were calculated for time interval of active rhamnolipid production and does not include period initial growth phase.

Production of Extracellular Metabolites Under N-Source Supplementation

As the N-source added in the fed-batch run FB2 was completely consumed by the bacteria with no accumulation of nitrate/ammonium in the broth (FIG. 11), it was important to inspect whether this ingested N-source resulted in production of other extracellular metabolites. It was likely that the supplemented N-source would result in the formation of other metabolites, presumably aromatic pigment compounds. The analyses of the broth using gel permeation chromatography (GPC) showed the formation of two distinct compounds having molecular weights of 300 Da and 3000 Da. These compounds were assumed to be characteristic pigments produced by P. aeruginosa. They were identified as aeruginosin (300 Da) and pyomelanin (3000 Da) based on their molecular weights. Some of the other commonly produced pigments by P. aeruginosa are pyocyanin (blue color and molecular weight of 210), pyorubrin (red color), and pyoverdine (yellow color and molecular weight of 1332). The formation of pigments by P. aeruginosa in the fermentation broth was also evident from the change in color of the samples taken at different times of the run. The concentrations of these compounds were higher in the fed-batch run as compared to the batch run, which implies that some of the provided N-source was utilized for syntheses of other extracellular metabolites. This formation of by-products in the fed-batch mode can affect the rhamnolipid specificity and yield as well as complicate the downstream processing and purification process.

Design of New Fermentation Run with High Cell Concentration and Rhamnolipid Productivity The above mentioned results were then combined to predict a fermentation run in which high cell concentration as well as rhamnolipid productivity can be achieved. The maximum cell concentration attained at different concentrations of nitrogen and non-nitrogen components in the initial medium was determined (See, Table. 11). It is desirable to obtain a high cell concentration with controllable foaming because high cell population would translate to a higher rhamnolipid volumetric productivity. It can be seen from Table. 11 that 0.5× of both nitrogen and non-nitrogen source concentration resulted in a maximum cell concentration of 7.5 g/L in approximately 11.01 h. This time was calculated using the maximum specific growth rate reported for this bacterial strain. Similarly, 1× of both nitrogen and non-nitrogen concentration resulted in 15 g/L cell concentration in about 13.23 h.

TABLE 11

Predicted values of highest cell concentration achieved and corresponding time required to reach the highest cell concentration at different concentrations of nitrogen and non-nitrogen components in the initial medium

| N-source | Non-N source | Maximum cell concentration (g/L) | Time taken to reach highest cell concentration (h) | Limiting component |
|---|---|---|---|---|
| 0.5X | 0.5X | 7.5 | 11.01 | Nitrogen |
| 1X | 1X | 15 | 13.23 | Nitrogen |
| 1X | 0.5X | 10 | NA | Non-Nitrogen |
| 1.5X | 1X | 19 | NA | Non-Nitrogen |

A new fermentation run was designed with the objective of achieving a high cell concentration and sustained rhamnolipid productivity during prolonged stationary phase. In the earlier fermentation runs, it was observed that there were operational difficulties associated with the fermentation process during the active growth period when the culture was grown to high cell concentrations over 20 g/L. These operational difficulties were caused mainly due to formation of stable foam during the period of active growth. The specific oxygen uptake rate during the active growth rate is typically about two orders of magnitude higher than during the stationary phase. Therefore, a high rate of aeration is required to meet the high oxygen demand during the active growth phase. This high aeration rate along with the intrinsic hydrophobic nature of the growing cells can cause formation of stable foam during the active growth phase, which can disrupt the process control. Thus, to achieve a high cell concentration in a short time interval in the current fermentation run, the period of active growth was divided into two distinct growth phases as shown in Table. 12. The first growth phase was designed to reach a maximum cell concentration of about 20 g/L with growth occurring at the maximum growth rate of 0.31 h$^{-1}$. This was achieved by providing suitable amount of nitrogen source in the initial medium which will support cell growth to 20 g/L in the first growth phase. In the second growth phase, nitrogen source was provided in a slow continuous mode to achieve a final cell concentration of about 31 g/L in about 8.4 hours. The addition of nitrogen source at a low flowrate in the second growth phase ensures that cells grow at a slow controlled rate which helps in maintaining lower time averaged respiration rate to avoid high oxygen demand and concomitant foaming. Thus, the total duration of the growth phase was about 28 hours and maximum cell concentration achievable at the end of this growth phase was 31 g/L. 15% of the total nitrogen added during the growth phase was supplemented every 24 hours to maintain a high rhamnolipid productivity during the stationary phase. It was assumed that a very high rate of N-source supplementation in the fed-batch fermentation would result in production of extracellular metabolites (such as pigments) in addition to rhamnolipids, which would negatively affect rhamnolipid productivity and yield.

The cell concentration profile during the active growth phase for this run is shown in FIG. 5A. The final cell concentration at the end of first growth phase was 13.48 g/L, which was lower than the predicted concentration in Table 12. This difference between the predicted and the actual cell concentration may have resulted due to the lag phase after inoculation of the culture in the fermenter. As set forth above, the lag phase involves a period of slow growth where the cell culture acclimatizes to the new nutrient medium and conditions by synthesizing the required enzymes and growth factors. The presence of this lag phase was neglected while designing the fermentation run. This fermentation run F5 gave a highest cell concentration of 29.2 g/L and final rhamnolipid concentration and overall productivity of 105.4 g/L and 731 mg/L-h respectively (See, FIG. 5A).

TABLE 12

Design for two-phase growth phase for fermentation run FB1

| | N-source (g/L) | Start time (h) | End time (h) | Expected final X (g/L) |
|---|---|---|---|---|
| Growth phase I | 3.6 | 0 | 19.20 | 19.61 |
| Growth phase II | 1.8 | 19.20 | 27.61 | 30.96 |

Effect of High Viscosity of the Fermentation Broth on Liquid Side Oxygen Transfer In the fermentation run FB1, there were problems associated with the transfer of oxygen from gaseous phase to the liquid phase during the later stages of fermentation. It was observed at 270 hours of fermentation time that the dissolved oxygen concentration of the broth remained close to zero, despite purging pure gaseous oxygen continuously at a flowrate of 1 L/min. The transfer of oxygen from gaseous phase to the liquid phase appeared to be restricted due to the high viscosity of the fermentation broth. The gaseous oxygen was being purged out without transferring into the liquid phase due to the high pressure of the incoming oxygen gas in the fermenter. This phenomenon can be explained using the overall mass transfer coefficient for the bioreactor, which is denoted by $k_La$. The volumetric mass transfer coefficients depends on several factors such as rate of agitation, air flow rate, air pressure, temperature, geometry of the vessel, and fluid characteristics such as density, viscosity, and surface tension. At a given agitation rate, there is a decrease in $k_La$ as the viscosity of the liquid medium increases. This phenomenon has previously been demonstrated by measuring the $k_La$ of the bioreactor at different liquid viscosities. Their results show that the $k_La$ value at 50% glycerol is significantly lower than that at 10% glycerol. 50% glycerol solution has a dynamic viscosity of 6.86 cP, while 10% glycerol solution has a dynamic viscosity of 1.22 cP.

It is clear that a highly viscous fermentation broth has a negative impact on the oxygen transfer efficiency in a fermenter, which can obstruct the availability of oxygen to cell culture in the fermentation broth. In rhamnolipid fermentations, there is an increase in viscosity of the broth with time. Thus, the sequential fed-batch fermentation mode can be used to overcome the negative effects of high viscosity on oxygen transfer in the fermentation broth.

Sequential Fed-Batch Fermentation for Achieving High Rhamnolipid Productivity

The high viscosity of the fermentation broth during longer fermentation runs prevents efficient transfer of oxygen from the gas phase to the liquid phase. This prevents cellular respiration which may lead the cells to transition into denitrification conditions. To maintain the fermentation runs for longer time durations, a sequential fed-batch run was developed. This design ensured that the cells were actively metabolizing and producing rhamnolipids throughout the fermentation run. In the run F6, a ratio of nitrogen to non-nitrogen components of 1.2 was used in the initial media. A second growth phase was induced at the end of the initial exponential growth phase by slow continuous addition of N-source. A highest cell concentration of 30.3 g/L was obtained in this run. N-source was supplemented at rate of 10% of the initial nitrogen every 48 h up to 144 h. The cell and rhamnolipid concentration profiles for this run are given in FIG. 6. About 85% of the fermentation broth volume was replaced with fresh medium at 144 h. N-source was once again supplemented in slow continuous manner to increase the cell concentration back to 27 g/L. Once the cells reached the stationary phase, N-source supplementation at similar rate of 10% of initial every 48 h, was continued for next 144 h. The volumetric productivities in the two production cycles were 559.6±91.8 mg/L-h and 522.6±45.5 mg/L-h.

Figure 13:
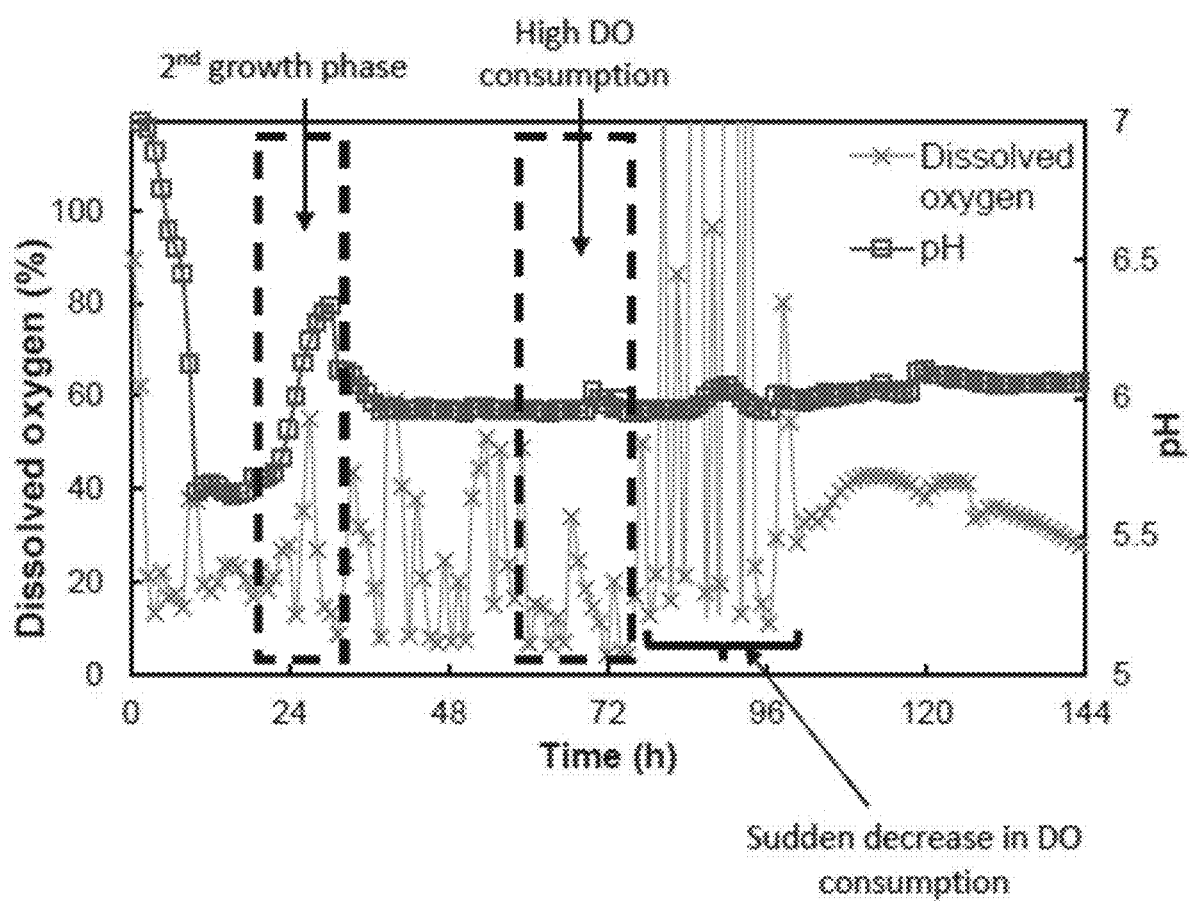
FIG. 13 is a graph showing dissolved oxygen and pH profiles in fermentation run FB7. N-source was supplemented at a rate of 45% of initial nitrogen after every 48. There was rapid decline in oxygen consumption rate beyond 72 hours.

It should be noted that a very high N-source supplementation would not prove to be beneficial in terms of cell growth and rhamnolipid productivity. A fermentation run (FB7) was conducted in similar process design as FB5 and FB6, but with N-source supplementation of 45% of initial nitrogen every 48 h. This was equivalent to supplying about 2.43 g/L of nitrogen in terms of ammonium nitrate, which corresponds to 5.4 g/L of $NO_3^-$. The dissolved oxygen (DO) and pH profile for this run is shown in FIG. 13. There was an abrupt decline in oxygen uptake rate beyond 72 h, which was presumably due to high nitrate concentration in the medium. It has been demonstrated that high nitrate concentration can hamper aerobic respiration by negatively affecting the enzymes involved in the electron transfer cycle during the oxidative phosphorylation process.

Example 4

Prolonged High Productivity Low-Growth or Stationary-Phase Rhamnolipid Production As set forth above, to increase productivity and product concentration, rhamnolipid production should be done with long stationary phase to extend the productive phase. The long stationary-phase production could also increase conversion because during this phase no substrate would be consumed for cell growth, i.e., making more cell biomass. For fermentations with stationary phase, the most common way is to design the fermentation media with nitrogen (N) source as the growth-limiting nutrient. It has been found that with proper design and operation to avoid other growth-limiting conditions, cells can grow until exhaustion of the nitrogen source when enzymes and nucleic acids essential for growth can no longer be formed.

It has also been found, however, that in rhamnolipid fermentation with such N-limiting media, the cells would slow rhamnolipid production after entering the stationary phase for about 100 h and almost stop the production after about 150-200 h into the stationary phase in presence of ample carbon source. If rhamnolipids are produced by typical batch fermentations, one would stop a batch after this productive period ends, and start a next batch of cleaning, medium filling and sterilization, seed inoculation, cell growth, and then 100-200 h of stationary-phase rhamnolipid production. It is clear to see the downtime (not producing rhamnolipids), labor, utilities and medium involved in the repeated short batches.

There are several possible causes for the declining rhamnolipid productivity. Through a series of experiments, we have sorted possible causes out and concluded that incomplete recycling of nitrogen source, presumably for maintaining adequate levels of certain key enzymes relevant to rhamnolipid synthesis, is responsible for the declining rhamnolipid productivity. In additional experiments, the effects of different modes and levels of supplementation of different types of nitrogen sources were studied.

The *Pseudomonas aeruginosa* bacterium and seed culture used in these experiments were as described Example 1, above. The composition and component concentrations of the carbon and non-nitrogen sources used for the fermentation medium were likewise as set forth above in Example 1. The concentration of the non-nitrogen sources described therein was considered to be 1×. The nitrogen source used for these experiments were ammonium chloride (inorganic), yeast extract, peptone (organic) or both (inorganic+organic) and were used in the concentrations set forth in Table 13. The medium pH was adjusted to 7.0 before autoclaving. Additionally, a 10 g/L betaine solution was filter-sterilized and added as an osmoprotectant, at a final concentration of 0.5 mM in the medium.

The (volumetric) productivity $Q_p$ (mg/L-h) and specific productivity $q_p$ (mg/g-h, i.e., mg rhamnolipids per g cells by dry weight per h) obtained during the active production period are compared in Table 13 for some experiments, FC1 to FC5, with cell growth limited by N-source availability. Note that $Q_p = q_p X$, where X is the average cell concentration (g/L) during the rhamnolipid producing period.

TABLE 13

Cell concentrations and rhamnolipid productivities in fermentations with N-limiting initial growth media, which were supplemented with no or different levels of N sources after reaching stationary phase

| Run No. | Initial N-source | Non-N substrate | N-source added (% initial N per day) | X (g/L) | $q_p$ (mg/g-h) | Normalized $Q_p$ (mg/L-h), per 1X initial N |
|---|---|---|---|---|---|---|
| FC1 | 2X | 2X | 0 (Control batch) | 9.5 | 26.7 | 127 |
| FC2 | 1X | 1X | 4.5 (Inorganic N) | 7.3 | 12.0 | 88.2 |
| FC3 | 1X | 1X | 4.5 (Inorganic + organic N) | 7.3 | 15.5 | 113 |
| FC4 | 1X | 1X | 15 (Inorganic N) | 9.7 | 10.5 | 102 |
| FC5 | 2X | 2X | 37.5 (Inorganic N) | 20.6 | 8.4 | 87 |

It should be noted that the cell concentrations given in the table were all converted from intracellular protein concentrations measured. So, different cell concentrations here actually reflected the different intracellular protein (enzyme) concentrations in the bacterial cultures, i.e., declining cell concentrations meant loss of active enzymes. FC1 was a typical batch fermentation without any N-source supplementation. The cell concentration in FC1 declined after peaking at the end of growth phase; as a result, the average cell concentration during the rhamnolipid producing period in FC1 was only about 30% higher than the average cell concentrations in FC2 and FC3 while the initial N source concentration in FC1 was 100% higher than that in FC2 and FC3. In FC2 and FC3, the cell concentrations maintained around the peak levels (without significant increase or decrease). The cell concentrations would increase at even higher levels of N-source supplementation as shown in FC4 and FC5. In FC5, the higher N supplementation caused cells to grow slowly to a much higher cell concentration, which had high respiration demand that needed high aeration to meet and caused too much foaming. The high N supplementation could not be maintained further. However, N supplementation even at the low level of 4.5% per day caused the specific productivity $q_p$ to drop; and, the higher the N supplementation level, the lower the $q_p$. N supplementation thus had a positive effect on maintaining or increasing cell concentration but a negative effect on cells' effectiveness in rhamnolipid synthesis. The combined effects may be compared by the normalized $Q_p$ values per 1× initial N source (last column in Table 13, above). So higher N supplementation was not beneficial for $Q_p$ when compared during the rhamnolipid productive periods in these fermentations. However, as mentioned earlier, without N supplementation, rhamnolipid production would slow and then stop after about 100-200 h; on the other hand, in FC2-FC4, rhamnolipid production continued for more than 400 to 600 h when we terminated the fermentations. Therefore, the low-level N supplementation can be more economical by enabling prolonged rhamnolipid production.

Most surprisingly, we found that nitrogen source would become limiting even in media originally designed with non-nitrogen nutrients as the limiting substrate. We found that in the latter case of using supposedly non-nitrogen-limiting media, the stationary-phase cells originally limited by the exhaustion of non-nitrogen substrate would overproduce N-containing metabolites along with rhamnolipids and cause the nitrogen source to become limiting too, which would again negatively affect the rhamnolipid production.

To show these effects, rhamnolipid production was compared in three fermentation runs in Table 14, below.

TABLE 14

Cell concentrations and rhamnolipid productivities in fermentations with N-source (FC1) or non-N substrate (FC6 and FC7) as limiting nutrient in initial growth media, which were supplemented without or with N sources after reaching stationary phase

| Run No. | Initial N-source | Non-N substrate | N-source added (% initial N per day) | X (g/L) | $q_p$ (mg/g-h) | $Q_p$ (mg/L-h) |
|---|---|---|---|---|---|---|
| FC1 | 2X | 2X | 0 | 9.5 | 26.7 | 254 |
| FC6 | 2X | 1X | 0 | 8.1 | 19.7 | 160 |
| FC7 | 2X | 1X | 75 | 12.9 | 26.8 | 347 |

FC1 was the same typical batch fermentation without N-source supplementation as shown in the previous table. In FC6 and FC7, the non-N substrates were halved which caused the medium to first become limited by certain non-N substrate. $NH_3$—N concentration was monitored in FC6. It was found that N also became depleted later and had some negative effect on cell (intracellular protein) concentration and rhamnolipid productivities $q_p$ and $Q_p$. N supplementation in FC7 prevented the N-source exhaustion. Consequently, the specific rhamnolipid productivity $q_p$ achieved in FC7 was equivalent to that in FC1 and substantially higher than those in FC2-FC5 (shown in Table 13) where N supplementation stimulated temporary cell growth and apparently suppressed rhamnolipid productivity. The $Q_p$ achieved in FC7 was substantially higher than that in FC1, because unlike in FC1, there was no declining cell concentration in FC7 where cell growth was limited by a non-N substrate and N supplementation was presumably only to avoid the negative effects associated with N-source exhaustion. $Q_p$ in FC7 was the highest among all of the experiments shown in Tables 13 and 14.

Rhamnolipid production can therefore be improved by prolonged high-productivity minimum-growth, e.g., with 15% initial N supplemented per day as in FC4, or no-growth, e.g., with 4.5% initial N supplementation in FC2 and FC3 or with adequate N supplementation while cell growth limited by a non-N substrate as in FC7.

Note that rhamnolipid fermentation broths are very foaming under gas bubbling and high agitation. The foam can rise very rapidly, wet the gas outlet and other potential points of contact to increase chance of contamination, and even spill the broth out of the fermenter. Foaming in fermentation can normally be controlled by addition of chemical antifoams. Rhamnolipid fermentation is however too foaming; so, solving the problem this way would require addition of large amounts of chemical antifoams, which are expensive and can complicate the downstream product collection and purification. Therefore, high rhamnolipid productivity cannot be simply achieved by growing cells to high cell concentrations in the exponential growth phase.

Continuous culture, termed also as chemostat, is another possible fermentation process. It is also not effective for rhamnolipid production because in continuous culture, cells are growing at a specific growth rate equal to the dilution rate used in the process: dilution rate=(flow rate)/(broth volume in the reactor). As described above, rhamnolipids are overproduced when cells are not growing or in minimal growth phase. Other drawbacks associated with continuous culture can include the waste of unconsumed substrates flowing in and out of the reactor and lower product concentration because product is continuously washed out of the reactor, unlike the allowed product accumulation in the batch reactor with N supplementation.

One more invention disclosed here is to improve rhamnolipid productivity by the following operation in sequential phases: In Phase 1, the cells are grown with a properly designed starting medium which would allow cells to grow very actively (e.g., exponentially) to a first chosen concentration at which the cell respiration rate can still be met by aeration/oxygenation without uncontrollable foaming. Phase 2 starts shortly before the growth-limiting substrate becomes exhausted. In Phase 2, the cell culture is fed or supplemented with a second medium at rates or frequencies that allow the cells to grow at slower rates and to a second chosen cell concentration. Phase 2 allows building up the cell concentration to a level not achievable by exponential growth as in a conventional batch fermentation so as to increase (volumetric) productivity in this phase and in the later Phase 3. The growth rates in Phase 2 need to be designed so that despite the increasing cell concentration, the overall respiration demand (=cell concentration×specific cell respiration rate, the latter being proportional to specific cell growth rate) remains manageable without excess foaming. Phase 3 is then the prolonged stationary phase with stable high cell concentration and high productivity for rhamnolipid production sustained by proper N supplementation. The feeding/supplementation in Phases 2 and 3 would cause broth volume to increase slowly. At some point, a portion of the broth can be harvested and Phases 2 and 3 repeated for continual rhamnolipid production.

The Phase 2 design is important because in our fermentation studies, we have found that the oxygen uptake rate is up to 2 orders of magnitude higher during the exponential phase than the stationary phase. This increased aeration requirement leads to uncontrolled foaming and causes operational difficulties. Phase 2 is to circumvent this problem, by having a regulated growth phase in Phase 2 after the initial growth phase (Phase 1) to achieve higher cell concentrations.

Actual design of the phased operation and media would depend on the fermenter configuration and aeration and agitation setups used in the production. As an example, the starting medium for Phase 1 can contain 1.5× N-source and 2× non-N substrates. (C source would be always properly provided to prevent C-source depletion and the resulting cell death and termination of rhamnolipid production.) N source is the growth-limiting nutrient in this medium. Phase 2 can be carried out at an N supplementation rate of 37.5% initial N per day. This would push the culture to a high cell concentration eventually limited by the non-N substrates. Phase 3 can then be carried out with N supplementation at a rate of 10% initial N per day.

In light of the foregoing, it should be appreciated that the present invention significantly advances the art by providing a method for making rhamnolipids that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A method for improving production rates, conversions and concentrations of rhamnolipids during fermentation-based rhamnolipid production under aerobic conditions comprising:

A) growing a rhamnolipid producing bacteria in a fermentation broth under aerobic conditions, said fermentation broth comprising at least one carbon source, at least one nitrogen source and a non-nitrogen source; and B) after the growth of said rhamnolipid producing bacteria is substantially complete, adding one or more additional quantities of a nutrient consisting of a nitrogen source to the fermentation broth to maintain a substantially non-decreasing rate of rhamnolipids production under aerobic conditions.

2. The method of claim 1 wherein the rhamnolipid producing bacteria is *Pseudomonas aeruginosa*.

3. The method of claim 1 wherein the step of growing (step A) further comprises:
1) determining a quantity of each one of said at least one carbon source, at least one nitrogen source, and non-nitrogen source necessary to grow said rhamnolipid producing bacteria to a desired cell concentration;
2) forming an initial fermentation medium comprising some or all of said quantity of the at least one carbon source necessary to grow said rhamnolipid producing bacteria to the desired cell concentration, some or all of said quantity of said non-nitrogen source necessary to grow said rhamnolipid producing bacteria to the desired cell concentration, and a first portion said quantity of the at least one nitrogen source necessary to grow said rhamnolipid producing bacteria to the desired cell concentration;
3) adding said rhamnolipid producing bacteria to said initial fermentation medium to form said fermentation broth and growing said rhamnolipid producing bacteria until the first portion of said at least one nitrogen source has been substantially consumed; and
4) adding any remaining carbon source and non-nitrogen source and gradually adding a remaining portion of said quantity of said at least one nitrogen source to said fermentation broth to continue growing said rhamnolipid producing bacteria until said remaining portion of said quantity of said at least one nitrogen source has been substantially consumed or growth of said rhamnolipid producing bacteria stops.

4. The method of claim 1 wherein said fermentation medium comprises phosphorus, sulfur, potassium, sodium, calcium, magnesium, chloride, iron, manganese, zinc, boron, cobalt, copper, and molybdenum.

5. The method of claim 3 wherein the initial fermentation medium comprises all of said quantity of the at least one carbon source necessary to grow said rhamnolipid producing bacteria to the desired cell concentration.

6. The method of claim 3 wherein a limiting nutrient in the fermentation broth of step 3 is the non-nitrogen source and the amount of said non-nitrogen source in said initial fermentation medium is equal to the quantity of said non-nitrogen source necessary to grow the rhamnolipid producing bacteria to the desired cell concentration.

7. The method of claim 3 wherein a limiting nutrient in the fermentation broth of step 3 is said nitrogen source.

8. The method of claim 3 wherein the step of gradually adding the remaining portion of said quantity of said at least one nitrogen source to said fermentation broth (step 4) comprises addition of said remaining portion of the quantity of said at least one nitrogen source to said fermentation broth in two or more batches.

9. The method of claim 3 wherein the step of gradually adding the remaining quantity of said at least one nitrogen source to said fermentation broth (step 4) comprises the substantially continuous addition of said remaining portion of said quantity of said at least one nitrogen source to said fermentation broth.

10. The method of claim 3 wherein a rate of foam formation in said the fermentation broth is controlled by controlling the rate at which the remaining portion of said quantity of the at least one nitrogen source is added to the fermentation broth (Step 4).

11. The method of claim 3 wherein the remaining portion of said quantity of the at least one nitrogen source in step 4 is added at a rate which limits foam formation.

12. The method of claim 1 wherein each of said one or more additional quantities of the nitrogen source in the step of adding of step B is added in an amount sufficient to maintain production of rhamnolipids at a substantially non-decreasing rate but not sufficient to permit the rhamnolipid producing bacteria to produce non-rhamnolipid byproducts.

13. The method of claim 1 wherein the additional quantity of a nitrogen source is added to the fermentation broth of step B in batches.

14. The method of claim 1 wherein the additional quantity of a nitrogen source is added to the fermentation broth of step B substantially continuously.

15. The method of claim 1 wherein the additional quantity of a nitrogen source in step B is added in batches of from 5% to 75% by weight of the amount of the nitrogen source in the fermentation broth of step A, every 12 hours to 48 hours.

16. The method of claim 1 wherein the additional quantity of a nitrogen source in step B is added substantially continuously in an amount of from 5% to 75% by weight of the amount of the nitrogen source in the fermentation broth of step A over every period of from 12 to 48 hours.

17. The method of claim 1 wherein the conversion of said carbon source to rhamnolipids after the growth of said rhamnolipid producing bacteria is substantially complete (step B) is from 50% to 90% by weight.

18. The method of claim 1 further comprising:
C) removing some or all of the fermentation broth and harvesting the rhamnolipids contained therein.

19. The method of claim 18 wherein the step of removing (Step C) comprises removing from 20% to 95% of the volume of the fermentation broth and harvesting the rhamnolipids contained therein, the method further comprising:
a) replacing the volume of the fermentation broth removed in the step of removing with a volume of said fermentation medium;
b) repeating steps B, C, and D; and
c) harvesting the rhamnolipids contained in the resulting fermentation broth.

20. The method of claim 19 wherein the step of repeating (Step b) is repeated from 1 to 100 times.

21. The method of claim 1 wherein said step of adding one or more additional quantities of a nitrogen source (step B) further comprises supplementing the nitrogen source in batches at a rate of from 5% to 75% by weight of an amount of said nitrogen source used to grow said rhamnolipid producing bacteria every 12 to 48 hours for from 24 hours to 600 hours until the rhamnolipid concentration in the fermentation broth reaches a concentration of at least 75 g/L.

22. The method of claim 1 wherein said step of adding one or more additional quantities of a nitrogen source (step B) further comprises continuously supplementing the nitrogen source to provide from 2.5% to 150% by weight of the amount of said nitrogen source used to grow said rhamnolipid producing bacteria every 24 hours.

23. The method of claim 1 wherein said step of adding one or more additional quantities of a nitrogen source (step B)

further comprises periodically supplementing the nitrogen source until the rhamnolipid concentration in the fermentation broth reaches a concentration of at least 75 g/L.

24. A process for producing rhamnolipids by bacterial fermentation comprising: A) preparing a bacterial seed culture comprising at least one rhamnolipid producing bacteria; B) preparing a fermentation medium in a suitable fermentation vessel, said fermentation medium comprising a carbon source, a nitrogen source, and a non-nitrogen source comprising phosphorus, sulfur, potassium, sodium, calcium, magnesium, chloride, iron, manganese, zinc, boron, cobalt, copper, and molybdenum; C) adding the bacterial seed culture comprising rhamnolipid producing bacteria and at least one of air and oxygen to the fermentation medium to form a fermentation broth; D) growing the rhamnolipid producing bacteria in said fermentation broth; E) periodically adding additional quantities of said nitrogen source to allow said rhamnolipid producing bacteria to grow until said non-nitrogen source is substantially consumed, wherein rhamnolipid producing bacteria growth substantially stops and rhamnolipids are produced; F) periodically supplementing said nitrogen source to maintain a substantially non-decreasing rate of rhamnolipids production until the rhamnolipid concentration in the fermentation broth reaches a concentration of from 50 g/L to 200 g/L; and G) removing some or all of the fermentation broth and harvesting the rhamnolipids contained therein.

25. The process for producing rhamnolipids by bacterial fermentation of claim 24 wherein the step of removing (Step G) comprises removing from 20% to 95% of the volume of the fermentation broth and harvesting the rhamnolipids contained therein, the method further comprising:
  1) replacing the volume of the fermentation broth removed in the step of removing with a volume of said fermentation medium;
  2) repeating steps D, E, F, G and H; and
  3) harvesting the rhamnolipids contained in the resulting fermentation broth.

26. The process for producing rhamnolipids by bacterial fermentation of claim 25 wherein the step of repeating (Step 2) is repeated from 1 to 100 times.

27. The process for producing rhamnolipids by bacterial fermentation of claim 24 wherein the rhamnolipid producing bacteria is *Pseudomonas aeruginosa*.

28. The process for producing rhamnolipids by bacterial fermentation of claim 24 further comprising controlling foam production in the step of periodically adding additional quantities of said nitrogen source (Step E) by varying the rate at which the additional quantities of said nitrogen source are added to the fermentation broth.

29. The process for producing rhamnolipids by bacterial fermentation of claim 24 wherein the nitrogen source in the step of periodically supplementing said nitrogen source to maintain a substantially non-decreasing rate of rhamnolipids production (step F) is supplemented in batches at a rate of from 5% to 75% by weight of the amount of said nitrogen source used to grow said rhamnolipid producing bacteria every 12 to 48 hours.

30. The process for producing rhamnolipids by bacterial fermentation of claim 29 wherein the nitrogen source is supplemented in batches at a rate of from 5% to 75% by weight of the amount of said nitrogen source used to grow said rhamnolipid producing bacteria every 12 to 48 hours for from about 24 hours to 600 hours until the rhamnolipid concentration in the fermentation broth reaches a concentration of at least 75 g/L.

31. The process for producing rhamnolipids by bacterial fermentation of claim 24 wherein the nitrogen source in the step of periodically supplementing said nitrogen source to prolong rhamnolipids production (step F) is continuously supplemented to provide from 2.5% to 150% by weight of the amount of said nitrogen source used to grow said rhamnolipid producing bacteria every 24 hours.

32. The process for producing rhamnolipids by bacterial fermentation of claim 24 wherein the nitrogen source in the step of periodically supplementing said nitrogen source to prolong rhamnolipids production (step F) are periodically supplemented until the rhamnolipid concentration in the fermentation broth reaches a concentration of at least 75 g/L.

33. The process for producing rhamnolipids by bacterial fermentation of claim 24 wherein from 50% to 90% by weight of said carbon source is converted into rhamnolipids.

* * * * *